1## United States Patent
Wilcox et al.

(10) Patent No.: US 9,982,034 B2
(45) Date of Patent: May 29, 2018

(54) PLATELET TARGETED TREATMENT

(71) Applicant: PLATELET TARGETED THERAPEUTICS, LLC, Brookfield, WI (US)

(72) Inventors: David A. Wilcox, Brookfield, WI (US); Sandra L. Haberichter, Greenfield, WI (US)

(73) Assignee: PLATELET TARGETED THERAPEUTICS, LLC, Brookfield, WI (US)

( * ) Notice: Subject to any disclaimer, the term of this patent is extended or adjusted under 35 U.S.C. 154(b) by 105 days.

(21) Appl. No.: 14/437,457

(22) PCT Filed: Oct. 24, 2013

(86) PCT No.: PCT/US2013/066651
§ 371 (c)(1),
(2) Date: Apr. 21, 2015

(87) PCT Pub. No.: WO2014/066663
PCT Pub. Date: May 1, 2014

(65) Prior Publication Data
US 2015/0344541 A1    Dec. 3, 2015

Related U.S. Application Data

(60) Provisional application No. 61/717,951, filed on Oct. 24, 2012.

(51) Int. Cl.
| | |
|---|---|
| C12N 15/85 | (2006.01) |
| C07K 14/755 | (2006.01) |
| A61K 35/28 | (2015.01) |
| C07K 14/705 | (2006.01) |
| A61K 48/00 | (2006.01) |
| A61K 35/12 | (2015.01) |

(52) U.S. Cl.
CPC ............ *C07K 14/755* (2013.01); *A61K 35/28* (2013.01); *A61K 48/0058* (2013.01); *C07K 14/7055* (2013.01); *A61K 2035/124* (2013.01)

(58) Field of Classification Search
None
See application file for complete search history.

(56) References Cited

U.S. PATENT DOCUMENTS

| | | | |
|---|---|---|---|
| 7,417,026 B2 | 8/2008 | Williams et al. | |
| 7,629,153 B2 | 12/2009 | Trono et al. | |
| 2004/0192599 A1 | 9/2004 | Schuh et al. | |
| 2006/0134663 A1 | 6/2006 | Harkin et al. | |
| 2010/0183556 A1 | 7/2010 | Choi et al. | |
| 2012/0225028 A1 | 9/2012 | Cohen et al. | |

FOREIGN PATENT DOCUMENTS

| | | |
|---|---|---|
| WO | 2010075303 A1 | 7/2010 |
| WO | 2011060242 A2 | 5/2011 |

OTHER PUBLICATIONS

Sarkar et al (Expert Opinion on Biological Therapy, 2007, vol. 7, No. 5, pp. 577-586).*
Wilcox et al. (Blood, 2000, vol. 95, No. 12, pp. 3645-3652).*
Haberichter et al (Arterioscler Thromb Vasc Biol., 2002. vol. 22, pp. 921-926).*
Prandini et al (The Journal of Biological Chemistry, vol. 267, No. 15, pp. 10370-10374).*
Sutter, "Dog star rising: the canine genetic system." Nat Rev Genet. Dec. 2004;5(12):900-10.
Wilcox Da, et al., "Gene therapy for platelet disorders",Platelets (Second Edition), Chapter 71,2007, pp. 1313-1325.
Wilcox Da, et al., "Induction of megakaryocytes to synthesize and store a releasable pool of human factor VIII." J Thromb Haemost. Dec. 2003;1(12):2477-89.
Wilcox Da, et al., "Integrin alphaIIb promoter-targeted expression of gene products in megakaryocytes derived from retrovirus-transduced human hematopoietic cells." Proc Natl Acad Sci U S A. Aug. 17, 1999;96(17):9654-9.
Wilcox Da, et al., "Megakaryocyte-targeted synthesis of the integrin beta(3)-subunit results in the phenotypic correction of Glanzmann thrombasthenia." Blood. Jun. 15, 2000;95(12):3645-52.
Wlcox Da, et al., "Gene therapy for platelet disorders: studies with Glanzmann's thrombasthenia." J Thromb Haemost. Nov. 2003;1(11):2300-11.
Yarovoi, et al., "Intracellular interaction of von Willebrand factor and factor VIII depends on cellular context: lessons from platelet-expressed factor VIII." Blood. Jun. 15, 2005;105(12):4674-6.
Gould, "Gene therapy: Genie in a vector." Nature. Nov. 27, 2014;515(7528):S160-1.
Kaufman, et al., "Good things come in small packages for hemophilia." J Thromb Haemost. Dec. 2003;1(12):2472-3.
Fang et al., "Platelets Engineered to Store Interleukin-24 Inhibited Melanoma Growth in Mice" presented at ISTH 2015 Congress, Toronto Jun. 20-25, 2015.
Greenberg et al., "Characterization of a new megakaryocytic cell line: the Dami cell." Blood. Dec. 1998;72 (6):1968-77.
Wiznerowicz et al., "Conditional suppression of cellular genes: lentivirus vector-mediated drug-inducible RNA interference." J Virol. Aug. 2003;77(16):8957-61.
International Search Report dated Jan. 22, 2014, of International Application No. PCT/US2013/066651, Filed Oct. 24, 2013. 18 Pages.
Adams, et al., Transduction of primary human hepatocytes with amphotropic and xenotropic retroviral vectors. "Transduction of primary human hepatocytes with amphotropic and xenotropic retroviral vectors." Proc Natl Acad Sci U S A. Oct. 1, 1992;89(19):8981-5.

(Continued)

*Primary Examiner* — Celine Qian
(74) *Attorney, Agent, or Firm* — Casimir Jones, S.C.

(57) ABSTRACT

The present disclosure relates to compositions and methods for targeting expression of exogenous genes to platelets. In particular, the present disclosure relates to treatment of hemophilia and other diseases and conditions by targeting expression of exogenous agents (e.g., clotting factors) to platelets.

7 Claims, 16 Drawing Sheets

(56) References Cited

OTHER PUBLICATIONS

Aiuti, et al., "Lentiviral Hematopoietic Stem Cell Gene Therapy in Patients with Wiskott-Aldrich Syndrome" Science, 341:865.
Bauer, et al., "Successful treatment of canine leukocyte adhesion deficiency by foamy virus vectors." Nat Med. Jan. 2008;14(1):93-7.
Biffi, et al. "Lentiviral vector common integration sites in preclinical models and a clinical trial reflect a benign integration bias and not oncogenic selection." Blood. May 19, 2011;117(20):5332-9.
Block, et al., "An Ets/Sp1 interaction in the 5'-flanking region of the megakaryocyte-specific alpha IIb gene appears to stabilize Sp1 binding and is essential for expression of this TATA-less gene." Blood. Sep. 15, 1996;88(6):2071-80.
Block, et al., "Characterization of regulatory elements in the 5'-flanking region of the rat GPIIb gene by studies in a primary rat marrow culture system." Blood. Nov. 15, 1994;84(10):3385-93.
Bray, et al., "Platelet glycoprotein IIb. Chromosomal localization and tissue expression." J Clin Invest. Dec. 1987;80(6):1812-7.
Burns, et al., "Vesicular stomatitis virus G glycoprotein pseudotyped retroviral vectors: concentration to very high titer and efficient gene transfer into mammalian and nonmammalian cells." Proc Natl Acad Sci U S A. Sep. 1, 1993;90(17):8033-7.
Choi, et al., Identification and characterization of nonapeptide targeting a human B cell lymphoma, Raji. Int Immunopharmacol. Jun. 2008;8(6):852-8.
Denarier, et al., "PCR cloning and sequence of the murine GPIIb gene promoter." Biochem Biophys Res Commun. Sep. 30, 1993;195(3):1360-4.
Doubeikovski, et al., "Thrombopoietin-induced expression of the glycoprotein IIb gene involves the transcription factor PU.1/Spi-1 in UT7-Mpl cells." J Biol Chem. Sep. 26, 1997;272(39):24300-7.
Enssle, et al., "Stable marking and transgene expression without progression to monoclonality in canine long-term hematopoietic repopulating cells transduced with lentiviral vectors." Hum Gene Ther. Apr. 2010;21(4):397-403.
Eustice, et al., "A sensitive method for the detection of beta-galactosidase in transfected mammalian cells." Biotechniques. Dec. 1991;11(6):739-40, 742-3.
Fang, et al., "Platelet gene therapy improves hemostatic function for integrin alphaIIbbeta3-deficient dogs." Proc Natl Acad Sci U S A. Jun. 7, 2011;108(23):9583-8.
Fang, et al., "Therapeutic expression of the platelet-specific integrin, alphaIIbbeta3, in a murine model for Glanzmann thrombasthenia." Blood. Oct. 15, 2005;106(8):2671-9.
Fu, et al., "Mobilization of hematopoietic stem cells." Blood Rev. Dec. 2000;14(4):205-18.
Gauwerky, et. al., "Hormonal effects on cell proliferation in a human erythroleukemia cell line (K562)." Blood. Nov. 1980;56(5):886-91.
Genbank M33319.1, Nov. 10, 2010, [retrieved on Jan. 4, 2014], retrieved from the internet: <URL:http//www.ncbi/nlm.nih.gov/nuccore/M33319.
Goldstein, et al., "In vitro studies with HeLa cell line sensitive and resistant to actinomycin D." Ann N Y Acad Sci. Oct. 5, 1960;89:474-83.
Griffin, et al., "Epsilon-aminocaproic acid (EACA)." Semin Thromb Hemost. 1978 Summer;5(1):27-40.
Haberichter et. al., "Critical independent regions in the VWF propeptide and mature VWF that enable normal VWF storage." Blood. Feb. 15, 2003;101(4):1384-91. Epub Oct. 10, 2002.
Haberichter, et. al., "The von Willebrand factor propeptide (VWFpp) traffics an unrelated protein to storage." Arterioscler Thromb Vasc Biol. Jun. 1, 2002;22(6):921-6.
Kuether, et al., "Lentivirus-mediated platelet gene therapy of murine hemophilia A with pre-existing anti-factor VIII immunity." J Thromb Haemost. Aug. 2012;10(8):1570-80.
Langdell, et al., "Effect of antihemophilic factor on one-stage clotting tests; a presumptive test for hemophilia and a simple one-stage antihemophilic factor assy procedure." J Lab Clin Med. Apr. 1953;41(4):637-47.

Lemarchandel, et al., "GATA and Ets cis-acting sequences mediate megakaryocyte-specific expression." Mol Cell Biol. Jan. 1993;13(1):668-76.
Leslie, "Cell biology. Beyond clotting: the powers of platelets." Science. Apr. 30, 2010;328(5978):562-4.
Lizee, et al., "Real-time quantitative reverse transcriptase-polymerase chain reaction as a method for determining lentiviral vector titers and measuring transgene expression." Hum Gene Ther. Apr. 10, 2003;14(6):497-507.
Lozier, et al., "The Chapel Hill hemophilia A dog colony exhibits a factor VIII gene inversion." Proc Natl Acad Sci U S A. Oct. 1, 2002;99(20):12991-6.
Markowitz, et al., "A safe packaging line for gene transfer: separating viral genes on two different plasmids." J Virol. Apr. 1988;62(4):1120-4.
Martin, et al., "The transcription factor GATA-1 regulates the promoter activity of the platelet glycoprotein IIb gene." J Biol Chem. Oct. 15, 1993;268(29):21606-12.
Mastromarino, et al., "Characterization of membrane components of the erythrocyte involved in vesicular stomatitis virus attachment and fusion at acidic pH." J Gen Virol. Sep. 1987;68 ( Pt 9):2359-69.
Matrai, et al., "Hepatocyte-targeted expression by integrase-defective lentiviral vectors induces antigen-specific tolerance in mice with low genotoxic risk." Hepatology. May 2011;53(5):1696-707.
McSweeney, et al., "Characterization of monoclonal antibodies that recognize canine CD34." Blood. Mar. 15, 1998;91 (6):1977-86.
Miller, "Human gene therapy comes of age." Nature. Jun. 11, 1992;357(6378):455-60.
Miller, et al., "Improved retroviral vectors for gene transfer and expression." Biotechniques. Oct. 1989;7(9):980-90.
Miller, et al., "Redesign of retrovirus packaging cell lines to avoid recombination leading to helper virus production." Mol Cell Biol. Aug. 1986;6(8):2895-902.
Miller, et al. "Gene transfer by retrovirus vectors occurs only in cells that are actively replicating at the time of infection." Mol Cell Biol. Aug. 1990;10(8):4239-42.
Naldini, et al., "In vivo gene delivery and stable transduction of nondividing cells by a lentiviral vector." Science. Apr. 12, 1996;272(5259):263-7.
Nichols, et al., "Sensitivity of whole blood clotting time and activated partial thromboplastin time for factor IX: relevance to gene therapy and determination of post-transfusion elimination time of canine factor IX in hemophilia B dogs." J Thromb Haemost. Mar. 2012;10(3):474-6.
Nichols, et al., "The roles of von Willebrand factor and factor VIII in arterial thrombosis: studies in canine von Willebrand disease and hemophilia A." Blood. May 15, 1993;81(10):2644-51.
Niemeyer, et a., "Correction of a large animal model of type I Glanzmann's thrombasthenia by nonmyeloablative bone marrow transplantation." Exp Hematol. Dec. 2003;31(12):1357-62.
Okamoto, et al., "Activation of a novel Kpnl transcript by downstream integration of a human T-lymphotropic virus type I provirus." J Biol Chem. Apr. 5, 1986;261(10):4615-9.
Prandini, et al., "Isolation of the human platelet glycoprotein IIb gene and characterization of the 5' flanking region." Biochem Biophys Res Commun. Oct. 14, 1988;156(1):595-601.
Prandini, et al., "The tissue-specific transcriptional regulation of the megakaryocytic glycoprotein IIb gene is controlled by interactions between a repressor and positive cis-acting elements." Blood. Sep. 15, 1996;88(6):2062-70.
Roe, et al., "Integration of murine leukemia virus DNA depends on mitosis." EMBO J. May 1993;12(5):2099-108.
Rosenberg, et al., "Intracellular trafficking of factor VIII to von Willebrand factor storage granules." J Clin Invest. Feb. 1, 1998;101(3):613-24.
Sahud, "Factor VIII inhibitors. Laboratory diagnosis of inhibitors." Semin Thromb Hemost. 2000;26(2):195-203.
Shi, et al., "Expression of human factor VIII under control of the platelet-specific alphaIIb promoter in megakaryocytic cell line as well as storage together with VWF." Mol Genet Metab. May 2003;79(1):25-33.

(56) References Cited

OTHER PUBLICATIONS

Shi, et al., "Factor VIII ectopically targeted to platelets is therapeutic in hemophilia A with high-titer inhibitory antibodies." J Clin Invest. Jul. 2006;116(7):1974-82.

Shi, et al., "Lentivirus-mediated platelet-derived factor VIII gene therapy in murine haemophilia A." J Thromb Haemost. Feb. 2007;5(2):352-61.

Kaufman, et la., "Effect of von Willebrand factor coexpression on the synthesis and secretion of factor VIII in Chinese iamster ovary cells." Mol Cell Biol. Mar. 1989;9(3):1233-42.

Shi, et al., "Syngeneic transplantation of hematopoietic stem cells that are genetically modified to express factor VIII in platelets restores hemostasis to hemophilia A mice with preexisting FVIII immunity." Blood. Oct. 1, 2008;112(7):2713-21.

\* cited by examiner

Fig 7

ITGA2B GENE Promoter(-671 to +30)>>>

```
-671 ATCGATATCTCCTTGCCACCTAGACCAAGGTCCATTCACCACCCTGTCCCCAGCACTGAC-618
     TAGCTATAGAGGAACGGTGGATCTGGTTCCAGGTAAGTGGTGGGACAGGGTCGTGACTG

-617 TGCACTGCTGTGGCCACACTAAAGCTTGGCTCAAGACGGAGGAGGAGTGAGGAAGCTGCT-558
     ACGTGACGACACCGGTGTGATTTCGAACCGAGTTCTGCCTCCTCCTCACTCCTTCGACGA
                               Ets
-557 GCACCAATATGGCTGGTTGAGGCCGCCCAAGGTCCTAGAAGG       GGGTAAATGCC-498
     CGTGGTTATACCGACCAACTCCGGCGGGTTCCAGGATCTTCC       CCCATTTACGG
                    GATA
-497 ATATCCAAAAAGATACAGAAGCCTCAGGTTTTATCGGGGGCAGCAGCTTCCTTCTCCTTC-438
     TATAGGTTTTTCTATGTCTTCGGAGTCCAAAATAGCCCCCGTCGTCGAAGGAAGAGGAAG

-437 CCCGACCTGTGGCCAAGTCACAAAGCACCACAGCTGTACAGCCAGATGGGGAAGGGAGG-378
     GGGCTGGACACCGGTTCAGTGTTTCGTGGTGTCGACATGTCGGTCTACCCCCTTCCCTCC
     GATA
-377 AGATTAGAACTGTAGGCTAGAGTAGACAAGTATGGACCAGTTCACAATCACGCTATCCCA-318
     TCTAATCTTGACATCCGATCTCATCTGTTCATACCTGGTCAAGTGTTAGTGCGATAGGGT

-317 AGCAGAAAGTGATGGTGGCTTGGACTAGCACGGTGGTAGTAGAGATGGGGTAAAGATTCA-258
     TCGTCTTTCACTACCACCGAACCTGATCGTGCCACCATCATCTCTACCCCATTTCTAAGT
         GATA
-257 AGAGACATCATTGATAGGCAGAACCAATAGGACATGGTAATAAACTATTCTCAGGAAAGG-198
     TCTCTGTAGTAACTATCCGTCTTGGTTATCCTGTACCATTATTTGATAAGAGTCCTTTCC
       Ets
-197 GG    CATGGCTTTCAGCCATGAGCATCCACCCTCTGGGTGGCCTCACCCACTTC -138
     CC    GTACCGAAAGTCGGTACTCGTAGGTGGGAGACCCACCGGAGTGGGTGAAG
     Repressor Start -139 to -63
-137                                                           -78

Repressor End      GATA           Ets
-77                 CCAGTTTGATAAGAAAAG     GTGGAGGAATCTGAAGGGAA -18
     TTCAATGAACCCCAAGGTCAAACTATTCTTTTC     CACCTCCTTAGACTTCCCTT ITGA2 Transcript start        VWFsp(+33 to +98)
          Sp1        +1                      +30|
 -17  G      CTGGCCCTTCCTGCCTGGGAGGTTGTGGAAGAAGC CA           44
      C      GACCGGGAAGGACGGACCCTCCAACACCTTCTTCC CG
                                    |VWFD2
  45                                                     G     104

```
 465  ...                                                         524
 525  ...                                                         584
 585  ...                                                         644
                  /Thrombin CLEAVAGE SITE
 645  ...                                                         704
 705  ...                                                         764
 765  ...                                                         824
 825  ...                                                         884
 885  ...                                                         944
      ACTCGACTTGACGGGCTTTCCGGTCCACATGGACGTCACGCCCTGGGGACGTTGGACTG
 945  ...                                                        1004
1005  ...                                                        1064
1065  ...                                                        1124
1125  ...                                                        1184
      CACGATGACACTCCTACCGAAGTACGTGACATGGTACTCACCTCAGGGGCCTTCGAACGA
         Furin Cleavage Site Abolished    End D2 Start FVIII(1232)
                         I                        ||
1185  ...                                                        1244
```

Figure 9

SEQ ID NO:25

TTGGAAGGGCTAATTCACTCCCAAAGAAGACAAGATATCCTTGATCTGTGGATCTACCACACACAAGGCTACT
TCCCTGATTAGCAGAACTACACACCAGGGCCAGGGGTCAGATATCCACTGACCTTTGGATGGTGCTACAAGCT
AGTACCAGTTGAGCCAGATAAGGTAGAAGAGGCCAATAAAGGAGAGAACACCAGCTTGTTACACCCTGTGAG
CCTGCATGGGATGGATGACCCGGAGAGAGAAGTGTTAGAGTGGAGGTTTGACAGCCGCCTAGCATTTCATCA
CGTGGCCCGAGAGCTGCATCCGGAGTACTTCAAGAACTGCTGATATCGAGCTTGCTACAAGGGACTTTCCGCT
GGGGACTTTCCAGGGAGGCGTGGCCTGGGCGGGACTGGGGAGTGGCGAGCCCTCAGATCCTGCATATAAGC
AGCTGCTTTTTGCCTGTACTGGGTCTCTCTGGTTAGACCAGATCTGAGCCTGGGAGCTCTCTGGCTAACTAGG
GAACCCACTGCTTAAGCCTCAATAAAGCTTGCCTTGAGTGCTTCAAGTAGTGTGTGCCCGTCTGTTGTGTGACT
CTGGTAACTAGAGATCCCTCAGACCCTTTTAGTCAGTGTGGAAAATCTCTAGCAGTGGCGCCCGAACAGGGAC
TTGAAAGCGAAAGGGAAACCAGAGGAGCTCTCTCGACGCAGGACTCGGCTTGCTGAAGCGCGCACGGCAAG
AGGCGAGGGGCGGCGACTGGTGAGTACGCCAAAAATTTTGACTAGCGGAGGCTAGAAGGAGAGAGATGGG
TGCGAGAGCGTCAGTATTAAGCGGGGGAGAATTAGATCGCGATGGGAAAAAATTCGGTTAAGGCCAGGGGG
AAAGAAAAAATATAAATTAAAACATATAGTATGGGCAAGCAGGGAGCTAGAACGATTCGCAGTTAATCCTGG
CCTGTTAGAAACATCAGAAGGCTGTAGACAAATACTGGGACAGCTACAACCATCCCTTCAGACAGGATCAGAA
GAACTTAGATCATTATATAATACAGTAGCAACCCTCTATTGTGTGCATCAAAGGATAGAGATAAAAGACACCA
AGGAAGCTTTAGACAAGATAGAGGAAGAGCAAAACAAAAGTAAGACCACCGCACAGCAAGCGGCCGGCCGC
TGATCTTCAGACCTGGAGGAGGAGATATGAGGGACAATTGGAGAAGTGAATTATATAAATATAAAGTAGTAA
AAATTGAACCATTAGGAGTAGCACCCACCAAGGCAAAGAGAAGAGTGGTGCAGAGAGAAAAAAGAGCAGTG
GGAATAGGAGCTTTGTTCCTTGGGTTCTTGGGAGCAGCAGGAAGCACTATGGGCGCAGCGTCAATGACGCTG
ACGGTACAGGCCAGACAATTATTGTCTGGTATAGTGCAGCAGCAGAACAATTTGCTGAGGGCTATTGAGGCG
CAACAGCATCTGTTGCAACTCACAGTCTGGGGCATCAAGCAGCTCCAGGCAAGAATCCTGGCTGTGGAAAGA
TACCTAAAGGATCAACAGCTCCTGGGGATTTGGGGTTGCTCTGGAAAACTCATTTGCACCACTGCTGTGCCTT
GGAATGCTAGTTGGAGTAATAAATCTCTGGAACAGATTTGGAATCACACGACCTGGATGGAGTGGGACAGAG
AAAATTAACAATTACACAAGCTTAATACACTCCTTAATTGAAGAATCGCAAAACCAGCAAGAAAAGAATGAACA
AGAATTATTGGAATTAGATAAATGGGCAAGTTTGTGGAATTGGTTTAACATAACAAATTGGCTGTGGTATATA
AAATTATTCATAATGATAGTAGGAGGCTTGGTAGGTTTAAGAATAGTTTTTGCTGTACTTTCTATAGTGAATAG
AGTTAGGCAGGGATATTCACCATTATCGTTTCAGACCCACCTCCCAACCCCGAGGGGACCCGACAGGCCCGAA
GGAATAGAAGAAGAAGGTGGAGAGAGAGACAGAGACAGATCCATTCGATTAGTGAACGGATCTCGACGGTA
TCGGTTAACTTTTAAAAGAAAAGGGGGGATTGGGGGGTACAGTGCAGGGGAAAGAATAGTAGACATAATAG
CAACAGACATACAAACTAAAGAATTACAAAAACAAATTACAAAAATTCAAAATTTTATCGATCACGAGACTAG
CCTCGAGAAGCTTGATCGATGGCTCCGGTGCCCGTCAGTGGGCAGAGCGCACATCGCCCACAGTCCCCGAGA
AGTTGGGGGGAGGGGTCGGCAATTGAACCGGTGCCTAGAGAAGGTGGCGCGGGGTAAACTGGGAAAGTGA
TGTCGTGTACTGGCTCCGCCTTTTTCCCGAGGGTGGGGGAGAACCGTATATAAGTGCAGTAGTCGCCGTGAAC
GTTCTTTTTCGCAACGGGTTTGCCGCCAGAACACAGGTGTCGTGACGCGGATCCAGGCCTAAGCTTACGATAT
CTCCTTGCCACCTAGACCAAGGTCCATTCACCACCCTGTCCCCAGCACTGACTGCACTGCTGTGGCCACACTAA
AGCTTGGCTCAAGACGGAGGAGGAGTGAGGAAGCTGCTGCACCAATATGGCTGGTTGAGGCCGCCCAAGGT
CCTAGAAGGAGGAAGTGGGTAAATGCCATATCCAAAAAGATACAGAAGCCTCAGGTTTTATCGGGGGCAGCA
GCTTCCTTCTCCTTCCCCGACCTGTGGCCAAGTCACAAAGCACCACAGCTGTACAGCCAGATGGGGGAAGGGA
GGAGATTAGAACTGTAGGCTAGAGTAGACAAGTATGGACCAGTTCACAATCACGCTATCCCAAGCAGAAAGT
GATGGTGGCTTGGACTAGCACGGTGGTAGTAGAGATGGGGTAAAGATTCAAGAGACATCATTGATAGGCAG
AACCAATAGGACATGGTAATAAACTATTCTCAGGAAAGGGGAGGAGTCATGGCTTTCAGCCATGAGCATCCA
CCCTCTGGGTGGCCTCACCCACTTCCTGGCAATTCTAGCCACCATGAGTCCAGGGGCTATAGCCCTTTGCTCTG

Figure 9 Cont.

```
CCCGTTGCTCAGCAAGTTACTTGGGGTTCCAGTTTGATAAGAAAAGACTTCCTGTGGAGGAATCTGAAGGGAA
GGAGGAGGAGCTGGCCCATTCCTGCCTGGGAGGTTGTGGAAGAAGGACCATGATTCCTGCCAGATTTGCCGG
GGTGCTGCTTGCTCTGGCCCTCATTTTGCCAGGGACCCTTTGCGAGTGCCTTGTCACAGGTCAATCACACTTCA
AGAGCTTTGACAACAGATACTTCACCTTCAGTGGGATCTGCCAGTACCTGCTGGCCCGGGATTGCCAGGACCA
CTCCTTCTCCATTGTCATTGAGACTGTCCAGTGTGCTGATGACCGCGACGCTGTGTGCACCCGCTCCGTCACCG
TCCGGCTGCCTGGCCTGCACAACAGCCTTGTGAAACTGAAGCATGGGGCAGGAGTTGCCATGGATGGCCAGG
ACGTCCAGCTCCCCCTCCTGAAAGGTGACCTCCGCATCCAGCGTACAGTGACGGCCTCCGTGCGCCTCAGCTA
CGGGGAGGACCTGCAGATGGACTGGGATGGCCGCGGGAGGCTGCTGGTGAAGCTGTCCCCCGTCTATGCCG
GGAAGACCTGCGGCCTGTGTGGGAATTACAATGGCAACCAGGGCGACGACTTCCTTACCCCCTCTGGGCTGG
CGGAGCCCCGGGTGGAGGACTTCGGGAACGCCTGGAAGCTGCACGGGGACTGCCAGGACCTGCAGAAGCA
GCACAGCGATCCCTGCGCCCTCAACCCGCGCATGACCAGGTTCTCCGAGGAGGCGTGCGCGGTCCTGACGTC
CCCCACATTCGAGGCCTGCCATCGTGCCGTCAGCCCGCTGCCCTACCTGCGGAACTGCCGCTACGACGTGTGC
TCCTGCTCGGACGGCCGCGAGTGCCTGTGCGGCGCCCTGGCCAGCTATGCCGCGGCCTGCGCGGGGAGAGG
CGTGCGCGTCGCGTGGCGCGAGCCAGGCCGCTGTGAGCTGAACTGCCCGAAAGGCCAGGTGTACCTGCAGT
GCGGGACCCCCTGCAACCTGACCTGCCGCTCTCTCTCTTACCCGGATGAGGAATGCAATGAGGCCTGCCTGGA
GGGCTGCTTCTGCCCCCCAGGGCTCTACATGGATGAGAGGGGGGACTGCGTGCCCAAGGCCCAGTGCCCCTG
TTACTATGACGGTGAGATCTTCCAGCCAGAAGACATCTTCTCAGACCATCACACCATGTGCTACTGTGAGGAT
GGCTTCATGCACTGTACCATGAGTGGAGTCCCCGGAAGCTTGCTGCCTGACGCTGTCCTCAGCAGTCCCCTGT
CTCATGGCAGCAAAAGGGCCACCAGAAGATACTACCTGGGTGCAGTGGAACTGTCATGGGACTATATGCAAA
GTGATCTCGGTGAGCTGCCTGTGGACGCAAGATTTCCTCCTAGAGTGCCAAAATCTTTTCCATTCAACACCTCA
GTCGTGTACAAAAAGACTCTGTTTGTAGAATTCACGGATCACCTTTTCAACATCGCTAAGCCAAGGCCACCCTG
GATGGGTCTGCTAGGTCCTACCATCCAGGCTGAGGTTTATGATACAGTGGTCATTACACTTAAGAACATGGCT
TCCCATCCTGTCAGTCTTCATGCTGTTGGTGTATCCTACTGGAAAGCTTCTGAGGGAGCTGAATATGATGATCA
GACCAGTCAAAGGGAGAAAGAAGATGATAAAGTCTTCCCTGGTGGAAGCCATACATATGTCTGGCAGGTCCT
GAAAGAGAATGGTCCAATGGCCTCTGACCCACTGTGCCTTACCTACTCATATCTTTCTCATGTGGACCTGGTAA
AAGACTTGAATTCAGGCCTCATTGGAGCCCTACTAGTATGTAGAGAAGGGAGTCTGGCCAAGGAAAAGACAC
AGACCTTGCACAAATTTATACTACTTTTTGCTGTATTTGATGAAGGGAAAAGTTGGCACTCAGAAACAAAGAA
CTCCTTGATGCAGGATAGGGATGCTGCATCTGCTCGGGCCTGGCCTAAAATGCACACAGTCAATGGTTATGTA
AACAGGTCTCTGCCAGGTCTGATTGGATGCCACAGGAAATCAGTCTATTGGCATGTGATTGGAATGGGCACCA
CTCCTGAAGTGCACTCAATATTCCTCGAAGGTCACACATTTCTTGTGAGGAACCATCGCCAGGCGTCCTTGGAA
ATCTCGCCAATAACTTTCCTTACTGCTCAAACACTCTTGATGGACCTTGGACAGTTTCTACTGTTTTGTCATATCT
CTTCCCACCAACATGATGGCATGGAAGCTTATGTCAAAGTAGACAGCTGTCCAGAGGAACCCCAACTACGAAT
GAAAAATAATGAAGAAGCGGAAGACTATGATGATGATCTTACTGATTCTGAAATGGATGTGGTCAGGTTTGA
TGATGACAACTCTCCTTCCTTTATCCAAATTCGCTCAGTTGCCAAGAAGCATCCTAAAACTTGGGTACATTACAT
TGCTGCTGAAGAGGAGGACTGGGACTATGCTCCCTTAGTCCTCGCCCCCGATGACAGAAGTTATAAAAGTCAA
TATTTGAACAATGGCCCTCAGCGGATTGGTAGGAAGTACAAAAAAGTCCGATTTATGGCATACACAGATGAAA
CCTTTAAGACTCGTGAAGCTATTCAGCATGAATCAGGAATCTTGGGACCTTTACTTTATGGGGAAGTTGGAGA
CACACTGTTGATTATATTTAAGAATCAAGCAAGCAGACCATATAACATCTACCCTCACGGAATCACTGATGTCC
GTCCTTTGTATTCAAGGAGATTACCAAAAGGTGTAAAACATTTGAAGGATTTTCCAATTCTGCCAGGAGAAAT
ATTCAAATATAAATGGACAGTGACTGTAGAAGATGGGCCAACTAAATCAGATCCTCGGTGCCTGACCCGCTAT
TACTCTAGTTTCGTTAATATGGAGAGAGATCTAGCTTCAGGACTCATTGGCCCTCTCCTCATCTGCTACAAAGA
ATCTGTAGATCAAAGAGGAAACCAGATAATGTCAGACAAGAGGAATGTCATCCTGTTTTCTGTATTTGATGAG
AACCGAAGCTGGTACCTCACAGAGAATATACAACGCTTTCTCCCCAATCCAGCTGGAGTGCAGCTTGAGGATC
```

Figure 9 Cont.

CAGAGTTCCAAGCCTCCAACATCATGCACAGCATCAATGGCTATGTTTTTGATAGTTTGCAGTTGTCAGTTTGT
TTGCATGAGGTGGCATACTGGTACATTCTAAGCATTGGAGCACAGACTGACTTCCTTTCTGTCTTCTTCTCTGG
ATATACCTTCAAACACAAAATGGTCTATGAAGACACACTCACCCTATTCCCATTCTCAGGAGAAACTGTCTTCA
TGTCGATGGAAAACCCAGGTCTATGGATTCTGGGGTGCCACAACTCAGACTTTCGGAACAGAGGCATGACCG
CCTTACTGAAGGTTTCTAGTTGTGACAAGAACACTGGTGATTATTACGAGGACAGTTATGAAGATATTTCAGC
ATACTTGCTGAGTAAAAACAATGCCATTGAACCAAGAGAAATAACTCGTACTACTCTTCAGTCAGATCAAGAG
GAAATTGACTATGATGATACCATATCAGTTGAAATGAAGAAGGAAGATTTTGACATTTATGATGAGGATGAAA
ATCAGAGCCCCCGCAGCTTTCAAAAGAAAACACGACACTATTTTATTGCTGCAGTGGAGAGGCTCTGGGATTA
TGGGATGAGTAGCTCCCCACATGTTCTAAGAAACAGGGCTCAGAGTGGCAGTGTCCCTCAGTTCAAGAAAGTT
GTTTTCCAGGAATTTACTGATGGCTCCTTTACTCAGCCCTTATACCGTGGAGAACTAAATGAACATTTGGGACT
CCTGGGGCCATATATAAGAGCAGAAGTTGAAGATAATATCATGGTAACTTTCAGAAATCAGGCCTCTCGTCCC
TATTCCTTCTATTCTAGCCTTATTTCTTATGAGGAAGATCAGAGGCAAGGAGCAGAACCTAGAAAAAACTTTGT
CAAGCCTAATGAAACCAAAACTTACTTTTGGAAAGTGCAACATCATATGGCACCCACTAAAGATGAGTTTGAC
TGCAAAGCCTGGGCTTATTTCTCTGATGTTGACCTGGAAAAAGATGTGCACTCAGGCCTGATTGGACCCCTTCT
GGTCTGCCACACTAACACACTGAACCCTGCTCATGGGAGACAAGTGACAGTACAGGAATTTGCTCTGTTTTTC
ACCATCTTTGATGAGACCAAAAGCTGGTACTTCACTGAAAATATGGAAAGAAACTGCAGGGCTCCCTGCAATA
TCCAGATGGAAGATCCCACTTTTAAAGAGAATTATCGCTTCCATGCAATCAATGGCTACATAATGGATACACTA
CCTGGCTTAGTAATGGCTCAGGATCAAAGGATTCGATGGTATCTGCTCAGCATGGGCAGCAATGAAAACATCC
ATTCTATTCATTTCAGTGGACATGTGTTCACTGTACGAAAAAAAGAGGAGTATAAAATGGCACTGTACAATCTC
TATCCAGGTGTTTTTGAGACAGTGGAAATGTTACCATCCAAAGCTGGAATTTGGCGGGTGGAATGCCTTATTG
GCGAGCATCTACATGCTGGGATGAGCACACTTTTTCTGGTGTACAGCAATAAGTGTCAGACTCCCCTGGGAAT
GGCTTCTGGACACATTAGAGATTTTCAGATTACAGCTTCAGGACAATATGGACAGTGGGCCCCAAAGCTGGCC
AGACTTCATTATTCCGGATCAATCAATGCCTGGAGCACCAAGGAGCCCTTTTCTTGGATCAAGGTGGATCTGTT
GGCACCAATGATTATTCACGGCATCAAGACCCAGGGTGCCCGTCAGAAGTTCTCCAGCCTCTACATCTCTCAGT
TTATCATCATGTATAGTCTTGATGGGAAGAAGTGGCAGACTTATCGAGGAAATTCCACTGGAACCTTAATGGT
CTTCTTTGGCAATGTGGATTCATCTGGGATAAAACACAATATTTTTAACCCTCCAATTATTGCTCGATACATCCG
TTTGCACCCAACTCATTATAGCATTCGCAGCACTCTTCGCATGGAGTTGATGGGCTGTGATTTAAATAGTTGCA
GCATGCCATTGGGAATGGAGAGTAAAGCAATATCAGATGCACAGATTACTGCTTCATCCTACTTTACCAATAT
GTTTGCCACCTGGTCTCCTTCAAAAGCTCGACTTCACCTCCAAGGGAGGAGTAATGCCTGGAGACCTCAGGTG
AATAATCCAAAAGAGTGGCTGCAAGTGGACTTCCAGAAGACAATGAAAGTCACAGGAGTAACTACTCAGGGA
GTAAAATCTCTGCTTACCAGCATGTATGTGAAGGAGTTCCTCATCTCCAGCAGTCAAGATGGCCATCAGTGGA
CTCTCTTTTTTCAGAATGGCAAAGTAAAGGTTTTTCAGGGAAATCAAGACTCCTTCACACCTGTGGTGAACTCT
CTAGACCCACCGTTACTGACTCGCTACCTTCGAATTCACCCCCAGAGTTGGGTGCACCAGATTGCCCTGAGGAT
GGAGGTTCTGGGCTGCGAGGCACAGGACCTCTACTGAGGGTGGCCACTGCAGCACCTGCCACTGCCGTCACC
TCTCCCTCCTCAGCTCCAGGGCAGTGTCCCTCCCTGGCTTGCCTTCTACCTTTGTGCTAAATCCTAGCAGACACT
GCCTTGAAGCCTCCTGAATTAACTATCATCAGTCCTGCATTTCTTTGGTGGGGGCCAGGAGGGTGCATCCAA
TTTAACTTAACTCTTACCTATTTTCTGCAGGGGGATCCTCTACTAGAGTCGACCTCGAGGGAATTCCGATAATC
AACCTCTGGATTACAAAATTTGTGAAAGATTGACTGGTATTCTTAACTATGTTGCTCCTTTTACGCTATGTGGAT
ACGCTGCTTTAATGCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCACTGTGTTTGCTGAC
GCAACCCCCACTGGTTGGGGCATTGCCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGCTCGGCTGTTGGGCACTGACAAT
TCCGTGGTGTTGTCGGGGAAGCTGACGTCCTTTCCATGGCTGCTCGCCTGTGTTGCCACCTGGATTCTGCGCG

Figure 9 Cont.

```
GGACGTCCTTCTGCTACGTCCCTTCGGCCCTCAATCCAGCGGACCTTCCTTCCCGCGGCCTGCTGCCGGCTCTG
CGGCCTCTTCCGCGTCTTCGCCTTCGCCCTCAGACGAGTCGGATCTCCCTTTGGGCCGCCTCCCCGCATCGGGA
ATTCGAGCTCGGTACCTTTAAGACCAATGACTTACAAGGCAGCTGTAGATCTTAGCCACTTTTTAAAAGAAAA
GGGGGGACTGGAAGGGCTAATTCACTCCCAACGAAGACAAGATGGGATCAATTCACCATGGGAATAACTTCG
TATAGCATACATTATACGAAGTTATGCTGCTTTTTGCTTGTACTGGGTCTCTCTGGTTAGACCAGATCTGAGCCT
GGGAGCTCTCTGGCTAACTAGGGAACCCACTGCTTAAGCCTCAATAAAGCTTGCCTTGAGTGCTTCAAGTAGT
GTGTGCCCGTCTGTTGTGTGACTCTGGTAACTAGAGATCCCTCAGACCCTTTTAGTCAGTGTGGAAAATCTCTA
GCAGCATCTAGAATTAATTCCGTGTATTCTATAGTGTCACCTAAATCGTATGTGTATGATACATAAGGTTATGT
ATTAATTGTAGCCGCGTTCTAACGACAATATGTACAAGCCTAATTGTGTAGCATCTGGCTTACTGAAGCAGACC
CTATCATCTCTCTCGTAAACTGCCGTCAGAGTCGGTTTGGTTGGACGAACCTTCTGAGTTTCTGGTAACGCCGT
CCCGCACCCGGAAATGGTCAGCGAACCAATCAGCAGGGTCATCGCTAGCCAGATCCTCTACGCCGGACGCAT
CGTGGCCGGCATCACCGGCGCCACAGGTGCGGTTGCTGGCGCCTATATCGCCGACATCACCGATGGGGAAGA
TCGGGCTCGCCACTTCGGGCTCATGAGCGCTTGTTTCGGCGTGGGTATGGTGGCAGGCCCCGTGGCCGGGGG
ACTGTTGGGCGCCATCTCCTTGCATGCACCATTCCTTGCGGCGGCGGTGCTCAACGGCCTCAACCTACTACTGG
GCTGCTTCCTAATGCAGGAGTCGCATAAGGGAGAGCGTCGAATGGTGCACTCTCAGTACAATCTGCTCTGATG
CCGCATAGTTAAGCCAGCCCCGACACCCGCCAACACCCGCTGACGCGCCCTGACGGGCTTGTCTGCTCCCGGC
ATCCGCTTACAGACAAGCTGTGACCGTCTCCGGGAGCTGCATGTGTCAGAGGTTTTCACCGTCATCACCGAAA
CGCGCGAGACGAAAGGGCCTCGTGATACGCCTATTTTTATAGGTTAATGTCATGATAATAATGGTTTCTTAGA
CGTCAGGTGGCACTTTTCGGGGAAATGTGCGCGGAACCCCTATTTGTTTATTTTTCTAAATACATTCAAATATG
TATCCGCTCATGAGACAATAACCCTGATAAATGCTTCAATAATATTGAAAAAGGAAGAGTATGAGTATTCAAC
ATTTCCGTGTCGCCCTTATTCCCTTTTTTGCGGCATTTTGCCTTCCTGTTTTTGCTCACCCAGAAACGCTGGTGAA
AGTAAAAGATGCTGAAGATCAGTTGGGTGCACGAGTGGGTTACATCGAACTGGATCTCAACAGCGGTAAGAT
CCTTGAGAGTTTTCGCCCCGAAGAACGTTTTCCAATGATGAGCACTTTTAAAGTTCTGCTATGTGGCGCGGTAT
TATCCCGTATTGACGCCGGGCAAGAGCAACTCGGTCGCCGCATACACTATTCTCAGAATGACTTGGTTGAGTA
CTCACCAGTCACAGAAAAGCATCTTACGGATGGCATGACAGTAAGAGAATTATGCAGTGCTGCCATAACCATG
AGTGATAACACTGCGGCCAACTTACTTCTGACAACGATCGGAGGACCGAAGGAGCTAACCGCTTTTTTGCACA
ACATGGGGGATCATGTAACTCGCCTTGATCGTTGGGAACCGGAGCTGAATGAAGCCATACCAAACGACGAGC
GTGACACCACGATGCCTGTAGCAATGGCAACAACGTTGCGCAAACTATTAACTGGCGAACTACTTACTCTAGC
TTCCCGGCAACAATTAATAGACTGGATGGAGGCGGATAAAGTTGCAGGACCACTTCTGCGCTCGGCCCTTCCG
GCTGGCTGGTTTATTGCTGATAAATCTGGAGCCGGTGAGCGTGGGTCTCGCGGTATCATTGCAGCACTGGGG
CCAGATGGTAAGCCCTCCCGTATCGTAGTTATCTACACGACGGGAGTCAGGCAACTATGGATGAACGAAAT
AGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAA
AATCCCTTAACGTGAGTTTTCGTTCCACTGAGCGTCAGACCCCGTAGAAAAGATCAAAGGATCTTCTTGAGATC
CTTTTTTTCTGCGCGTAATCTGCTGCTTGCAAACAAAAAAACCACCGCTACCAGCGGTGGTTTGTTTGCCGGAT
CAAGAGCTACCAACTCTTTTTCCGAAGGTAACTGGCTTCAGCAGAGCGCAGATACCAAATACTGTCCTTCTAGT
GTAGCCGTAGTTAGGCCACCACTTCAAGAACTCTGTAGCACCGCCTACATACCTCGCTCTGCTAATCCTGTTAC
CAGTGGCTGCTGCCAGTGGCGATAAGTCGTGTCTTACCGGGTTGGACTCAAGACGATAGTTACCGGATAAGG
CGCAGCGGTCGGGCTGAACGGGGGGTTCGTGCACACAGCCCAGCTTGGAGCGAACGACCTACACCGAACTG
AGATACCTACAGCGTGAGCATTGAGAAAGCGCCACGCTTCCCGAAGGGAGAAAGGCGGACAGGTATCCGGT
AAGCGGCAGGGTCGGAACAGGAGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCGTCAGGGGGGCGGAGCCTATGGAA
AAACGCCAGCAACGCGGCCTTTTTACGGTTCCTGGCCTTTTGCTGGCCTTTTGCTCACATGTTCTTTCCTGCGTT
```

Figure 9 Cont.

ATCCCCTGATTCTGTGGATAACCGTATTACCGCCTTTGAGTGAGCTGATACCGCTCGCCGCAGCCGAACGACC
GAGCGCAGCGAGTCAGTGAGCGAGGAAGCGGAAGAGCGCCCAATACGCAAACCGCCTCTCCCCGCGCGTTG
GCCGATTCATTAATGCAGCTGTGGAATGTGTGTCAGTTAGGGTGTGGAAAGTCCCCAGGCTCCCCAGCAGGC
AGAAGTATGCAAAGCATGCATCTCAATTAGTCAGCAACCAGGTGTGGAAAGTCCCCAGGCTCCCCAGCAGGC
AGAAGTATGCAAAGCATGCATCTCAATTAGTCAGCAACCATAGTCCCGCCCCTAACTCCGCCCATCCCGCCCCT
AACTCCGCCCAGTTCCGCCCATTCTCCGCCCCATGGCTGACTAATTTTTTTTATTTATGCAGAGGCCGAGGCCG
CCTCGGCCTCTGAGCTATTCCAGAAGTAGTGAGGAGGCTTTTTTGGAGGCCTAGGCTTTTGCAAAAAGCTTGG
ACACAAGACAGGCTTGCGAGATATGTTTGAGAATACCACTTTATCCCGCGTCAGGGAGAGGCAGTGCGTAAA
AAGACGCGGACTCATGTGAAATACTGGTTTTTAGTGCGCCAGATCTCTATAATCTCGCGCAACCTATTTTCCCC
TCGAACACTTTTTAAGCCGTAGATAAACAGGCTGGGACACTTCACATGAGCGAAAAATACATCGTCACCTGGG
ACATGTTGCAGATCCATGCACGTAAACTCGCAAGCCGACTGATGCCTTCTGAACAATGGAAAGGCATTATTGC
CGTAAGCCGTGGCGGTCTGTACCGGGTGCGTTACTGGCGCGTGAACTGGGTATTCGTCATGTCGATACCGTTT
GTATTTCCAGCTACGATCACGACAACCAGCGCGAGCTTAAAGTGCTGAAACGCGCAGAAGGCGATGGCGAAG
GCTTCATCGTTATTGATGACCTGGTGGATACCGGTGGTACTGCGGTTGCGATTCGTGAAATGTATCCAAAAGC
GCACTTTGTCACCATCTTCGCAAAACCGGCTGGTCGTCCGCTGGTTGATGACTATGTTGTTGATATCCCGCAAG
ATACCTGGATTGAACAGCCGTGGGATATGGGCGTCGTATTCGTCCCGCCAATCTCCGGTCGCTAATCTTTTCAA
CGCCTGGCACTGCCGGGCGTTGTTCTTTTTAACTTCAGGCGGGTTACAATAGTTTCCAGTAAGTATTCTGGAGG
CTGCATCCATGACACAGGCAAACCTGAGCGAAACCCTGTTCAAACCCCGCTTTAAACATCCTGAAACCTCGAC
GCTAGTCCGCCGCTTTAATCACGGCGCACAACCGCCTGTGCAGTCGGCCCTTGATGGTAAAACCATCCCTCACT
GGTATCGCATGATTAACCGTCTGATGTGGATCTGGCGCGGCATTGACCCACGCGAAATCCTCGACGTCCAGGC
ACGTATTGTGATGAGCGATGCCGAACGTACCGACGATGATTTATACGATACGGTGATTGGCTACCGTGGCGG
CAACTGGATTTATGAGTGGGCCCCGGATCTTTGTGAAGGAACCTTACTTCTGTGGTGTGACATAATTGGACAA
ACTACCTACAGAGATTTAAAGCTCTAAGGTAAATATAAAATTTTTAAGTGTATAATGTGTTAAACTACTGATTC
TAATTGTTTGTGTATTTTAGATTCCAACCTATGGAACTGATGAATGGGAGCAGTGGTGGAATGCCTTTAATGA
GGAAAACCTGTTTTGCTCAGAAGAAATGCCATCTAGTGATGATGAGGCTACTGCTGACTCTCAACATTCTACTC
CTCCAAAAAAGAAGAGAAAGGTAGAAGACCCCAAGGACTTTCCTTCAGAATTGCTAAGTTTTTTGAGTCATGC
TGTGTTTAGTAATAGAACTCTTGCTTGCTTTGCTATTTACACCACAAAGGAAAAAGCTGCACTGCTATACAAGA
AAATTATGGAAAAATATTCTGTAACCTTTATAAGTAGGCATAACAGTTATAATCATAACATACTGTTTTTTCTTA
CTCCACACAGGCATAGAGTGTCTGCTATTAATAACTATGCTCAAAAATTGTGTACCTTTAGCTTTTTAATTTGTA
AAGGGGTTAATAAGGAATATTTGATGTATAGTGCCTTGACTAGAGATCATAATCAGCCATACCACATTTGTAG
AGGTTTTACTTGCTTTAAAAAACCTCCCACACCTCCCCCTGAACCTGAAACATAAAATGAATGCAATTGTTGTT
GTTAACTTGTTTATTGCAGCTTATAATGGTTACAAATAAAGCAATAGCATCACAAATTTCACAAATAAAGCATT
TTTTTCACTGCATTCTAGTTGTGGTTTGTCCAAACTCATCAATGTATCTTATCATGTCTGGATCAACTGGATAAC
TCAAGCTAACCAAAATCATCCCAAACTTCCCACCCCATACCCTATTACCACTGCCAATTACCTAGTGGTTTCATT
TACTCTAAACCTGTGATTCCTCTGAATTATTTTCATTTTAAAGAAATTGTATTTGTTAAATATGTACTACAAACTT
AGTAG

Figure 10

A  -SalI BgIII -1218 Human αIIb Gene NcoI Promoter for Luciferase

TTACGCGTCGACAGATCTAAATGTGGCTATGGTTACCCCTAGCGGACCTCTTAAAT
CTTCCTGAGAACCTGCTTTTTTGGGAAGGCATGAGTGCCAGTAAGACTTGGCACTCCTCCTCTTCCGCTT
ACCGAGAGAAAATGACTTTGCCTTTCTGCTCAAAACTCATCCCTTCACTTTGTCACCCTATGTTTGCATC
TTCCATCCTTAGTGTGTGTTTCCATCCATCCAGTCTCTTTCAGCAATACACGTACTACACATTGGACTCTTG
GGTAGTCTCTAGGGCTGTAGCAAGGAGCCTTGCTCCCAAGGGACTCATTTACACAATCCTGTGAACGGAC
CAAGAGTAAACAGTGTGCTCAATGCTGTGCCTACGTGTGTTAGCCCACGCGGGCCAGCCTGAGGAGTCAGG
GAAGGCTCCCCTAGGCAAAGCCCCCAACCAGAATCAAGTCTTAATGGTTAAAGAGCTCCATCACCCAAAA
AGGATTGAGGGCCTACCTTCAACTGAACAGCTAATGCATAATCTCAGAAACTGTGAGTCAAAATTCCCTG
GAATAACTCCACTTTATCCCCAATCTCCTTGCCACCTAGACCAAGGTCCATTCACCACCCTGTCCCCAGC
ACTGACTGCACTGCTGTGGCCACACTAAAGCTTGGCTCAAGACGGAGGAGGAGTGAGGAAGCTGCTGCAC
CAATATGGCTGGTTGAGGCCGCCCAAGGTCCTAGAAGGAGGAAGTGGGTAAATGCCATATCCAAAAAGAT
ACAGAAGCCTCAGGTTTTATCGGGGGCAGCAGCTTCCTTCTCCTTCCCCGACCTGTGGCCAAGTCACAAA
GCACCACAGCTGTACAGCCAGATGGGGGAAGGGGAGGAGATTAGAACTGTAGGCTAGAGTAGACAAGTATG
GACCAGTTCACAATCACGCTATCCCAAGCAGAAAGTGATGGTGGCTTGGACTAGCACGGTGGTAGTAGAG
ATGGGGTAAAGATTCAAGAGACATCATTGATAGGCAGAACCAATAGGACATGGTAATAAACTATTCTCAG
GAAAGGGGAGGAGTCATGGCTTTCAGCCATGAGCATCCACCCTCTGGGTGGCCTCACCCACTTCCTGGCA
ATTCTAGCCACCATGAGTCCAGGGGCTATAGCCCTTTGCTCTGCCCGTTGCTCAGCAAGTTACTTGGGGT
TCCAGTTTGATAAGAAAAGACTTCCTGTGGAGGAATCTGAAGGGAAGGAGGAGGAGCTGGCCCATTCCTG
CCTGGGAGGTTGTGGAAGAAGGACCATG

B  -SalI BgIII -889 Human αIIb Gene NcoI Promoter for Luc & FVIII

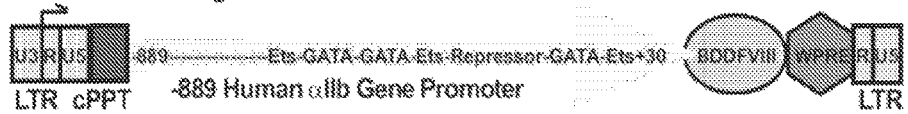

TTACGCGTCGACAGATCTGTGCTCAATGCTGTGCCTACGTGTGTTAGCCCACGCGGGCCAGCCTGAGGAGTCAGG
GAAGGCTCCCCTAGGCAAAGCCCCCAACCAGAATCAAGTCTTAATGGTTAAAGAGCTCCATCACCCAAAA
AGGATTGAGGGCCTACCTTCAACTGAACAGCTAATGCATAATCTCAGAAACTGTGAGTCAAAATTCCCTG
GAATAACTCCACTTTATCCCCAATCTCCTTGCCACCTAGACCAAGGTCCATTCACCACCCTGTCCCCAGC
ACTGACTGCACTGCTGTGGCCACACTAAAGCTTGGCTCAAGACGGAGGAGGAGTGAGGAAGCTGCTGCAC
CAATATGGCTGGTTGAGGGCCGCCCAAGGTCCTAGAAGGAGGAAGTGGGTAAATGCCATATCCAAAAAGAT
ACAGAAGCCTCAGGTTTTATCGGGGGCAGCAGCTTCCTTCTCCTTCCCCGACCTGTGGCCAAGTCACAAA
GCACCACAGCTGTACAGCCAGATGGGGGAAGGGGAGGAGATTAGAACTGTAGGCTAGAGTAGACAAGTATG
GACCAGTTCACAATCACGCTATCCCAAGCAGAAAGTGATGGTGGCTTGGACTAGCACGGTGGTAGTAGAG
ATGGGGTAAAGATTCAAGAGACATCATTGATAGGCAGAACCAATAGGACATGGTAATAAACTATTCTCAG
GAAAGGGGAGGAGTCATGGCTTTCAGCCATGAGCATCCACCCTCTGGGTGGCCTCACCCACTTCCTGGCA
ATTCTAGCCACCATGAGTCCAGGGGCTATAGCCCTTTGCTCTGCCCGTTGCTCAGCAAGTTACTTGGGGT
TCCAGTTTGATAAGAAAAGACTTCCTGTGGAGGAATCTGAAGGGAAGGAGGAGGAGCTGGCCCATTCCTG
CCTGGGAGGTTGTGGAAGAAGGACCATG

C  -SalI BgIII -673 Human αIIb Gene NcoI Promoter for Luc & FVIII

TTACGCGTCGACAGATCTCCTTGCCCACCTAGACCAAGGTCCATTCACCACCCTGTCCCCAGC
ACTGACTGCACTGCTGTGGCCACACTAAAGCTTGGCTCAAGACGGAGGAGGAGTGAGGAAGCTGCTGCAC
CAATATGGCTGGTTGAGGCCGCCCAAGGTCCTAGAAGGAGGAAGTGGGTAAATGCCATATCCAAAAAGAT
ACAGAAGCCTCAGGTTTTATCGGGGGCAGCAGCTTCCTTCTCCTTCCCCGACCTGTGGCCAAGTCACAAA
GCACCACAGCTGTACAGCCAGATGGGGGAAGGGGAGGAGATTAGAACTGTAGGCTAGAGTAGACAAGTATG
GACCAGTTCACAATCACGCTATCCCAAGCAGAAAGTGATGGTGGCTTGGACTAGCACGGTGGTAGTAGAG
ATGGGGTAAAGATTCAAGAGACATCATTGATAGGCAGAACCAATAGGACATGGTAATAAACTATTCTCAG
GAAAGGGGAGGAGTCATGGCTTTCAGCCATGAGCATCCACCCTCTGGGTGGCCTCACCCACTTCCTGGCA
ATTCTAGCCACCATGAGTCCAGGGGCTATAGCCCTTTGCTCTGCCCGTTGCTCAGCAAGTTACTTGGGGT
TCCAGTTTGATAAGAAAAGACTTCCTGTGGAGGAATCTGAAGGGAAGGAGGAGGAGCTGGCCCATTCCTG
CCTGGGAGGTTGTGGAAGAAGGACCATG

PLATELET TARGETED TREATMENT

This application is a national phase application under 35 U.S.C. § 371 of PCT International Application No. PCT/US2013/066651 filed Oct. 24, 2013, which claims priority to U.S. Provisional Application No. 61/717,951 filed Oct. 24, 2012, each of which are herein incorporated by reference in its entirety.

STATEMENT REGARDING FEDERALLY SPONSORED RESEARCH OR DEVELOPMENT

This invention was made with government support under Grant No. R01 HL068138 awarded by the National Institutes of Health. The government has certain rights in the invention.

FIELD OF THE INVENTION

The present disclosure relates to compositions and methods for targeting expression of exogenous genes to platelets. In particular, the present disclosure relates to treatment of hemophilia and other diseases and conditions by targeting expression of exogenous agents (e.g., clotting factors) to platelets.

BACKGROUND OF THE INVENTION

Hemophilia is a common bleeding disorder (occurring in approximately 1:10,000 males) in which causes severe internal bleeding that often leads to death because the patient's blood doesn't clot normally. Hemophilia usually is inherited with patients displaying severe uncontrollable bleeding events beginning at birth and re-occurring throughout the individual's life. Although there are several types of clotting factors that work together with platelets to help the blood coagulate, people with hemophilia usually have quantitative or qualitative defects in the proteins that encode coagulation factor VIII (hemophilia A) or factor IX (hemophilia B) that prevent normal hemostasis.

Hematopoietic stem cells differentiate in the bone marrow to form megakaryocytes that mature and break-up into several thousand small fragments known as platelets, which in normal conditions circulate quietly (not interacting with the other blood cells or the vessel wall) in the blood stream for approximately 10 days with the main job to become activated, change shape and stick to damaged blood vessel to repair the injury. When blood vessels are injured, clotting factors help platelets stick together to plug cuts and close breaks on the vessels to stop bleeding.

People with hemophilia A are missing or have low levels of clotting factor VIII. About 9 out of 10 people who have hemophilia have type A. People with hemophilia B are missing or have low levels of clotting factor IX. Both clotting factors are normally synthesized in the liver although there are reports that other cell types can be induced to synthesize fully functional forms of recombinant FVIII and FIX proteins.

Hemophilia can be mild, moderate, or severe, depending on how much normal functional clotting factor is present in the blood. About 7 out of 10 people who have hemophilia A have the severe form of the disorder.

Hemophilia usually occurs in males because Factors VIII and IX are located on the X chromosome (although with rare exceptions females who inherit a defective X chromosome each from an affected father and mother who is a carrier for the disease). About 1 in 10,000 individuals are born with hemophilia each year all over the world.

The main treatment for hemophilia is protein replacement therapy. Concentrates of clotting factor VIII (for hemophilia A) or clotting factor IX (for hemophilia B) can be isolated from pools of donor blood or recombinant protein that has been prepared from tissue culture cell lines transformed with the normal genes encoding FVIII or FIX that are slowly dripped or injected into a vein at the onset of a serious bleeding event. These infusions help replace the clotting factor that's missing or low.

Complications of replacement therapy include developing antibodies response to the normal therapeutic protein that is foreign to the patient's immune system (known as inhibitor formation), which ultimately leads to inactivation or destruction of the clotting factor and uncontrolled bleeding in about 30% of patients, developing viral infections from human clotting factors (from blood contaminated with HIV or Hepatitis from infected blood donors especially in third world countries), very expensive costs of the replacement protein which has a very short half-life (days) which requires frequent re-administration to subside a severe vascular injury and damage to joints, muscles, or other parts of the body resulting from delays in treatment.

Thus, new treatments for hemophilia that overcome these complications are needed.

SUMMARY OF THE INVENTION

The present disclosure relates to compositions and methods for targeting expression of exogenous genes to platelets. In particular, the present disclosure relates to treatment of hemophilia and other diseases and conditions by targeting expression of exogenous agents (e.g., clotting factors) to platelets. In some embodiments, the present disclosure relates to compositions and clinically relevant methods for hematopoietic stem cell gene therapy where targeting expression of exogenous genes within bone marrow megakaryocytes leads to expression and/or storage of recombinant therapeutic proteins within human platelets.

For example, in some embodiments, the present invention provides a composition comprising an expression vector comprising a) an expression cassette comprising a fragment of the integrin αIIb gene (ITGA2B) promoter; and an exogenous gene of interest operably linked to the expression cassette. In some embodiments, the expression cassette comprises, consists essentially of, or consists of a nucleic acid sequence selected from, for example, SEQ ID NOs: 21, 22, or 23, or sequences larger or smaller than SEQ ID NOs:21, 22, 23, or 25 (e.g., 1, 2, 3, 4, 5, 6, 7, 8, 9, 10, 20, 30, 40, 50, 60, 75, 100, 150, 200, 300, 400, 500, 600 or more nucleotides larger or smaller than SEQ ID NOs: 21, 22, 23, and 25) or fragments thereof. In some embodiments, the expression vector further comprises targeting factor (e.g., a fragment of the human Von Willebrand Factor propeptide (VWFpp) operably linked to a D2 domain) (e.g., as described by SEQ ID NO:24 or sequences 1, 2, 3, 4, 5, 6, 7, 8, 9, 10, 20, 30, 40, 50, 60, 75, 100, 150, 200, 300, 400, 500, 600 or more nucleotides larger or smaller than SEQ ID NO: 24 or fragment of SEQ ID NO:24). The present invention is not limited to a particular exogenous gene. Examples include, but are not limited to, a human FVIII or FIX gene. In some embodiments, the vector is a self-inactivating vector, for example, a retroviral vector (e.g., a lentiviral vector).

Further embodiments provide a hematopoietic stem cell comprising the expression vectors described herein (e.g., an ex vivo stem cell).

In yet other embodiments, the present invention provides the use of such stem cells to treat diseases and conditions (e.g., hemophilia) in an animal (e.g., a human).

The present invention also provides a method, comprising: contacting a hematopoietic stem cell with a vector as described herein to generate a modified stem cell under conditions such that a gene (e.g., Factor VIII gene) is expressed in the modified stem cell. In some embodiments, the method further comprises the step of transferring said modified stem cell into an animal (e.g., human). In some embodiments, the animal has been diagnosed with hemophilia and the transferring treats or prevents excessive bleeding in the animal. In some embodiments, the contacting occurs ex vivo. In some embodiments, the stem cells are mobilized from the animal (e.g., by administration of cytokines, mobilization into peripheral blood, contacting apheresis collection, immune magnetic bead isolation). In some embodiments, the animal expresses said Factor VIII in platelets. In some embodiments, the method is repeated (e.g., at regular intervals or when needed).

Additional embodiments are described herein.

DESCRIPTION OF THE FIGURES

FIG. 7 shows structural regions of the ITGA2B gene promoter and VWFspD2. Arrows show serious bleeding events before and after platelet targeted treatment. Dogs I42 and M64 show complete correction of hemostasis

FIG. 9 shows the sequence (SEQ ID NO:25) of the vector of FIG. 8.

FIG. 10 shows a diagram and nucleotide sequence for integrin αIIb promoter fragments used in recombinant lentivirus gene transfer constructs. (A) Nucleotide sequence for −Sal I Bgl II −1218 to +30 of human αIIb-gene promoter Nco I used for Megakaryocyte-Specific Luciferase reporter studies (SEQ ID NO:21). (B) Nucleotide sequence for −Sal I Bgl II −889 to +30 of human αIIb-gene promoter Nco I used for Megakaryocyte-Specific Luciferase reporter studies (SEQ ID NO:22). (C) Nucleotide sequence for −Sal I Bgl II −673 to +30 of human αIIb-gene promoter Nco I used for Megakaryocyte-Specific Luciferase reporter studies (SEQ ID NO:23). Numbering is based on Prandini, et al (Biochem Biophys Res Commun 156(1) 595-601, 1988).

DEFINITIONS

Figure 1:
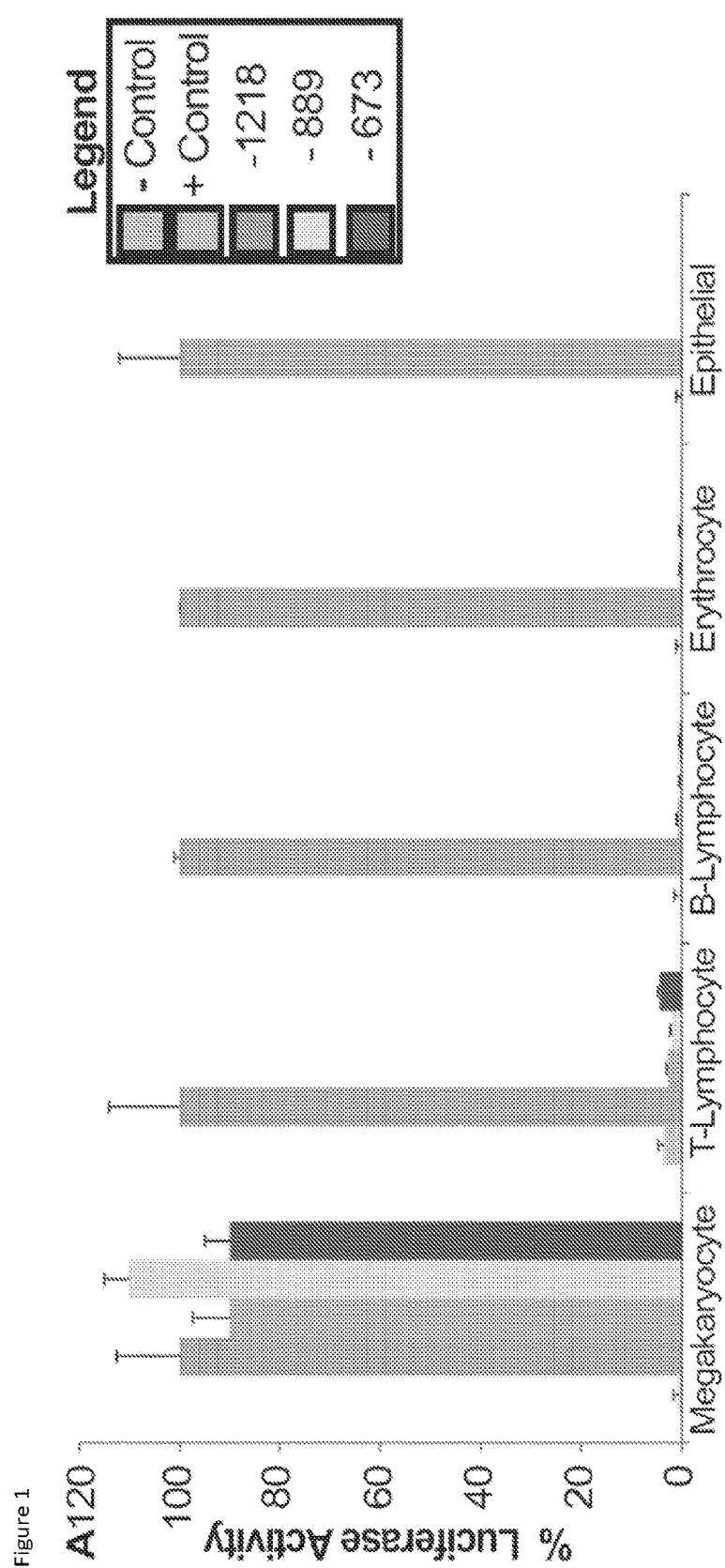
FIG. 1 shows platelet-targeted lentiviral vector design. (A) ITGA2B gene promoter fragments direct megakaryocyte-specific expression in luciferase. (B) −889ITGA2B-BDDFVIII-WPTS lentiviral vector diagram. (C) −673ITGA2B-VWFSPD2-BDDFVIII-WPTS lentiviral vector diagram.
Figure 1:
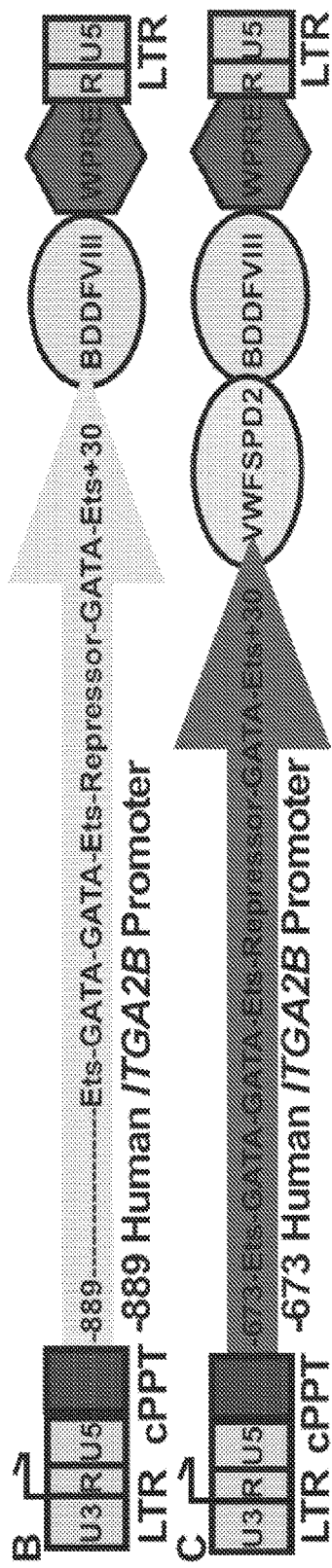

To facilitate an understanding of the present invention, a number of terms and phrases are defined below:

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, human artificial chromosomes, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

Promoter/enhancer," as used herein, denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter. Regulatory elements may be tissue specific or cell specific. The term "tissue specific" as it applies to a regulatory element refers to a regulatory element that is capable of directing selective expression of a nucleotide sequence of interest to a specific type of tissue (e.g., mammary gland) in the relative absence of expression of the same nucleotide sequence(s) of interest in a different type of tissue (e.g., liver). Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

As used herein the term "portion" or "fragment" when in reference to a nucleotide sequence (as in "a portion or fragment of a given nucleotide sequence") refers to fragments of that sequence. The fragments may range in size from four nucleotides to the entire nucleotide sequence minus one nucleotide (10 nucleotides, 20, 30, 40, 50, 100, 200, etc.). In some embodiments, fragments comprise a nucleotide sequence (e.g., promoter) that are 1, 2, 3, 4, 5, 6, 7, 8, 9, 10, 11, 12, 13, 14, 15, 16, 17, 18, 19, 20, 30, 40, 50, 100, 150, or 200 nucleotides less than the sequence or subsets thereof (e.g., 31, 32, 33, 34, 35, 35, 36, 37, 38, 39 nucleotides shorter and the like).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by bacterial infection.

DETAILED DESCRIPTION OF THE INVENTION

The present disclosure relates to compositions and methods for targeting expression of exogenous genes to platelets. In particular, the present disclosure relates to treatment of hemophilia and other diseases and conditions by targeting expression of exogenous agents (e.g., clotting factors) to platelets.

Embodiments of the present invention provide compositions and method for directing expression of a heterologous gene to a specific cell type using a cell-specific promoter. For example, in some embodiments, expression of heterologous or exogenous genes is targeted to a stem cell (e.g., cancer stem cell or hematopoietic stem cell) that in turn expresses the gene of interest in progenitor cells (e.g., platelets). The compositions and methods find use in the treatment of a variety of disease (e.g., platelet mediated diseases such as hemophilia). Certain embodiments of the present invention are illustrated based on treatment of hemophilia with exogenous or heterologous clotting factors, although the present invention is not limited to the treatment of hemophilia or platelet disorders.

In some embodiments, the present disclosure relates to treatment of hemophilia and rare and common inherited bleeding disorders as well as other diseases states that involve platelets (e.g. thrombosis of veins and arteries, immune response, and cancer) and conditions by employing hematopoietic stem cell gene therapy using a fragment of a platelet specific gene promoter to drive expression of proteins only in the platelet lineage and in some circumstances fusion of a signal peptide to the therapeutic molecule to traffic recombinant proteins specifically to platelet α-granules to induce regulated release of the exogenous agents from activated platelets at the site of injury. In summary, this approach allows platelets to be utilized as a vehicle to deliver therapeutic agents to enable wound repair targeting expression of exogenous agents (e.g., normal replacement proteins to restore hemostasis by correcting inherited platelet defects, clotting factors for hemophilia, anti-thrombotic agents for deep vein thrombosis and artery occlusion and anti-neoplastic agents to shrink solid tumors and prevent angiogenesis in cancer) to platelets.

There are several well-characterized inherited genetic defects that affect various aspects of platelet function (activation, adhesion, aggregation, signal transduction, granule storage), which usually manifest themselves clinically as a failure to control bleeding (Leslie, M. Science 328, 562-564 (2010)). Embodiments of the present invention provide autologous transplant of hematopoietic stem cells transduced with genes encoding normal integrin gene promoter driving synthesis of coagulation FVIII within platelets for correction of hemophilia A within humans. De novo synthesis of a biologically normal molecule within megakaryocytes has previous allowed trafficking of the entire protein to allow platelets to participate in wound repair. This is supported by the recent success of using hematopoietic stem cell gene transfer of integrin αIIb gene promoter driving expression of integrin αIIb to generate denovo synthesis of integrin αIIbβ3 receptor complex on platelets for improved platelet function and reduced bleeding times and blood loss for dogs deficient in integrin αIIb affected with canine Glanzmann Thrombasthenia (GT) (Fang, J. et al. Proc Natl Acad Sci USA 108, 9583-9588 (2011)).

Transduction of G-CSF mobilized peripheral blood stem cells (G-PBC) with an oncoretrovirus vector encoding integrin β3 generated de novo synthesis of viable integrin αIIbβ3 complexes on megakaryocytes derived from human GT patients (Wilcox, D. A et al., Blood. 95: 3645-52, 2000; Leslie, M. Science 328, 562-564 (2010)). It has also been shown that platelet function could be corrected within a murine model for GT by transplantation of bone marrow transduced with a lentivirus vector encoding β3 (Fang, J. et al., Blood 106, 2671-2679 (2005)) and that the use of hematopoietic stem cell gene transfer of integrin αIIb to generate αIIbβ3 on platelets can correct Canine Glanzmann Thrombasthenia (GT) (Fang, J. et al. Proc Natl Acad Sci USA 108, 9583-9588 (2011)).

Experiments conducted during the course of development of embodiments of the present invention demonstrate transferring genes into G-PBC show that oncoretrovirus transduced human megakaryocytes and platelets could synthesize and store human coagulation factor VIII and release FVIII upon activation in vitro with physiological agonists of platelet activation (Wilcox, D. A., et al., Journal of Thrombosis and Haemostasis. 1: 2477-89, 2003). It has also been shown that hemostasis could be improved within a murine model for hemophilia A (even in the presence of inhibitory antibodies to FVIII) by transplantation of bone marrow transduced with a lentivirus vector under the transcriptional control of the −889 fragment of the integrin αIIb gene promoter driving expression of human FVIII (Shi, Q. and Wilcox, D. A., et al., Journal of Thrombosis and Haemostasis 5: 352-361, 2007) and (Shi, Q., et al., Blood 112: 2713-21, 2008) and that the use of G-CSF mobilized PBC for hematopoietic stem cell lentivirus mediate gene transfer of integrin αIIb gene promoter fragment with and without VWFSPD2 fused to human FVIII induced expression of fully functional FVIII within platelets and platelet a granules, which corrected platelet function and resulted in improved hemostasis and the reduction and/or absence of any serious bleeding events; thus animals did not require injection with FVIII protein replacement therapy within a large animal "canine" model for hemophilia A for at least 2.5 years after transplant as well as inhibitory antibodies were not generated to the recombinant human FVIII stored within canine platelets Accordingly, in some embodiments the present invention provides compositions and methods for genetic therapies for targeting stem cells (e.g., hematopoietic stem cells). The compositions and methods described herein find use in the treatment of a variety of disease and conditions (e.g., platelet mediated disorders).

Some embodiments of the present invention are illustrated with the treatment of hemophilia and other platelet diseases, although the present invention is not limited to the treatment of hemophilia. In some embodiments, compositions and methods comprise in vivo or ex vivo genetic therapies. For example, in some embodiments, hematopoietic stem cells are mobilized and targeted ex vivo with vectors that target expression of exogenous genes (e.g., clotting factors, platelet proteins pertinent to platelet function, anti-thrombotic agents for thrombotic disorders and anti-angiogenic and anti-neoplastic agents for oncogenic disorders) specifically to platelets following reintroduction of the modified hematopoietic stem cells.

I. Vectors

Figure 8:
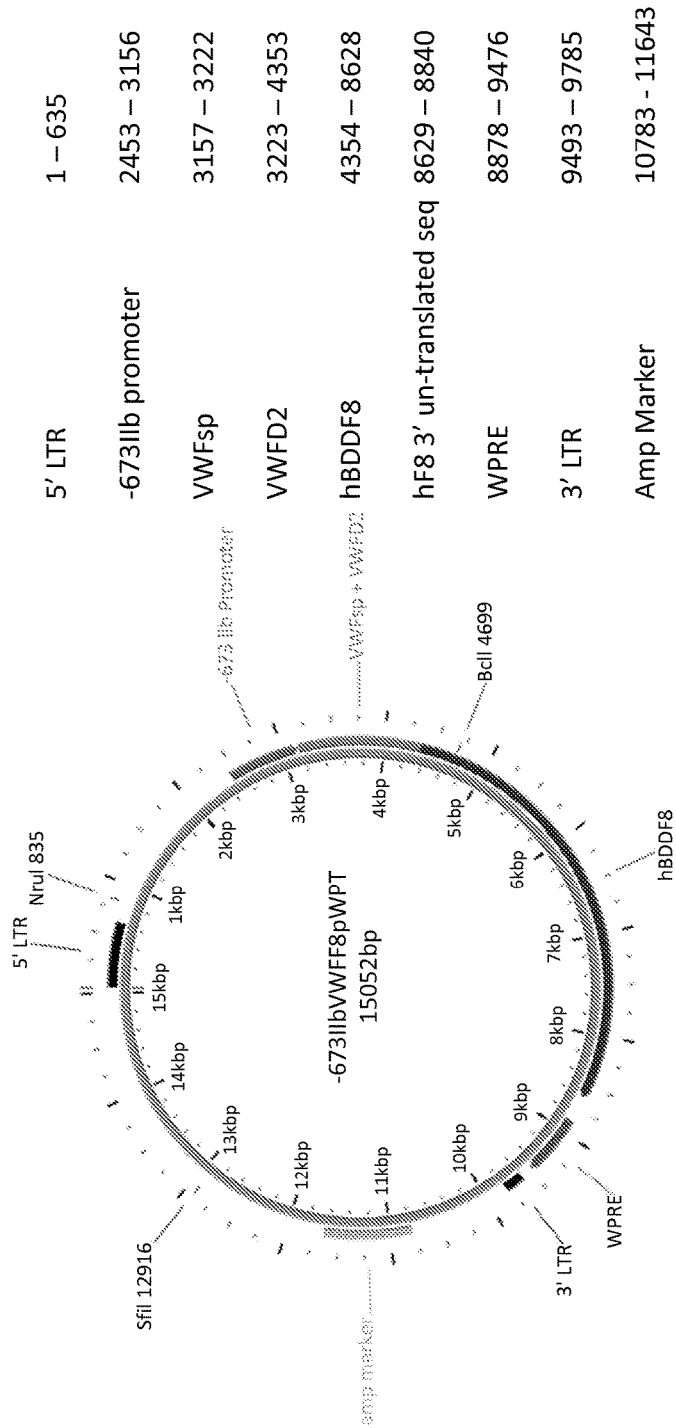
FIG. 8 shows an exemplary lentiviral gene therapy vector of embodiments of the present disclosure.

The present invention is not limited to a particular targeting vector or expression cassette. In some embodiments, expression cassettes comprise an exogenous gene of interest operable linked to a cell (e.g., platelet) specific promoter. In some embodiments, expression cassettes further comprise genes expression targeting or signal molecules, as well as expression enhancers. FIGS. 7, 8, and 10 show exemplary expression cassettes and vectors useful in embodiments of the present invention. Exemplary vector components are described below.

A. Promoters

In some embodiments, vectors comprise promoters that direct gene expression to particular cell type. For example, in some embodiments, promoters are platelet specific promoters. The present invention is not limited to particular platelet specific promoter. In some embodiments, truncated integrin αIIb gene (ITGA2B) promoters are used. Exemplary promoters include, but are not limited to, −1218, −889 and −673 ITGA2B promoters that encode "ETS" and "GATA" elements for high level of gene transcription within megakaryocytes and a Repressor region that inhibits gene transcription within other hematopoietic cell lineages (SEQ ID NOs: 21, 22, 23; and 25; FIGS. 8 and 10).

The nucleotide sequence of the ITGA2B gene promoter was first characterized in 1988 by a group in France headed by Dr. Gerard Marguerie (Prandini M H, Denarier E, Frachet P, Uzan G, Marguerie G. Isolation of the human platelet glycoprotein IIb gene and characterization of the 5' flanking region. Biochem Biophys Res Commun 1988, 156(1): 595-601). FIG. 7 shows structural regions of the ITGA2B promoter. In some embodiments, a fragment (e.g., 1218, −889 and −673) of the promoter is utilized. In some embodiments, the −673 contains all of the essential regulatory elements to drive platelet-specific transgene expression. In 1993, researchers perform gene promoter studies and found that the transcription factor GATA-1 was important for high level gene expression in megakaryocytes with at least three and maybe a fourth region serves as GATA-1 binding site identified in ITGA2B (Martin F, Prandini M H, Thevenon D, Marguerie G, Uzan G. The transcription factor GATA-1 regulates the promoter activity of the platelet glycoprotein IIb gene. J Biol Chem 1993, 268(29): 21606-21612). Next it was discovered that there are three consensus sequences for another transcription factor Ets to bind to ITGA2B that are believed to act together to produce a high level of transgene expression (Lemarchandel V, Ghysdael J, Mignotte V, Rahuel C, Romeo P H. GATA and Ets cis-acting sequences mediate megakaryocyte-specific expression. Mol Cell Biol 1993, 13(1): 668-676). The Murine ITGA2B promoter was cloned and found to have very high nucleotide sequence homology with the human ITGA2B promoter, especially at the regions where transcription factors consensus binding sequences were identified (Denarier E, Martin F, Martineau S, Marguerie G. PCR cloning and sequence of the murine GPIIb gene promoter. Biochem Biophys Res Commun 1993, 195(3): 1360-1364). Further gene promoter analysis showed that a region of ITGA2B from −139 to −63 must be preserved to prevent the gene promoter from driving transgene transcription within other hematopoietic lineages, thus this region is labeled the Repressor (Prandini M H, Martin F, Thevenon D, Uzan G. The tissue-specific transcriptional regulation of the megakaryocytic glycoprotein IIb gene is controlled by interactions between a repressor and positive cis-acting elements. Blood 1996, 88(6): 2062-2070). Finally, a binding site for the Sp1 was identified in ITGA2B that is believed important to work with Ets in conjunction with the other elements when promoter forms a three dimensional structure that is essential for optimal platelet specific gene transcription (Block K L, Shou Y, Poncz M. An Ets/Sp1 interaction in the 5'-flanking region of the megakaryocyte-specific alpha IIb gene appears to stabilize Sp1 binding and is essential for expression of this TATA-less gene. Blood 1996, 88(6): 2071-2080).

The present invention is not limited to the ITGA2B promoters described in SEQ ID NOs: 21-23). Embodiments of the present invention contemplate fragments, portions, and combinations of the fragments described herein. In some embodiments, fragments are shorter than the full length ITGA2B promoter (e.g., 1, 2, 3, 4, 5, 6, 7, 8, 9, 10, 20, 30, 40, 50, 60, 75, 100, 150, 200 or more nucleotides shorter) and maintain desired activity (e.g., the ability to drive cell-specific expression to elicit a desired effect, e.g., reduction in sing or symptoms of a disease or condition).

In some embodiments, promoters comprise the ITGA2B fragments described in SEQ ID NOs: 21, 22, and 23, or sequences that are 1, 2, 3, 4, 5, 6, 7, 8, 9, 10, 20, 30, 40, 50, 60, 75, 100, 150, 200, 300, 400, 500, 600 or more nucleotides larger or smaller than SEQ ID NOs: 21, 22, and 23. For example, in some embodiments, fragments that are 1, 2, 3, 4, 5, 6, 7, 8, 9, 10, 20, 30, 40, 50, 60, 75, 100, 150, 200 or more nucleotides smaller than SEQ ID NO:21 are utilized. In some embodiments, fragments that are 1, 2, 3, 4, 5, 6, 7, 8, 9, 10, 20, 30, 40, 50, 60, 75, 100, 150, 200, 300, 400, 500, 600 or more nucleotides larger than SEQ ID NO:23 are utilized.

In some embodiments, discontinuous fragments of SEQ ID NOs: 21, 22, or 23 that retain promoter activity are utilized. For example in some embodiments, 1, 2, 3, 4, 5, 6, 7, 8, 9, 10, 20, 30, 40, 50, 60, 75, 100, 150, 200, 300, 400, 500, 600 nucleotides of SEQ ID NOs 21, 22, or 23 are utilized.

In some embodiments, promoter fragments comprise one or more elements useful for promoter activity. Examples include, but are not limited to, GATA elements (e.g., GATA54 or GATA454), sP1 elements, Ets35 elements, and the like (See e.g., Block et al., Blood 1994 84: 3385-3393; Prandini et al., Blood 1996 88: 2062-2070; Block et al., Blood 1996 88: 2071-2080; and Doubeikovski et al., J. Biol. Chem. 272: 24300-24307, 1997; each of which is herein incorporated by reference in its entirety).

In some embodiments, the 5' ends of promoters are modified to add restriction endonuclease sites to aid in cloning and constructing expression vectors. For example, in some embodiments, 1, 2, 3, or 4 nucleotides at the 5' end are modified from the wild type sequence or the fragments disclosed herein to add restriction endonuclease sites.

In some embodiments, the fragments comprise, consist essentially of, or consist of promoter sequence found in SEQ ID NOs: 21, 22, or 23.

B. Heterologous Genes

The present invention is not limited to a particular exogenous gene. In embodiments that treat hemophilia, exogenous genes are generally clotting factors (e.g., Factor VIII and/or Factor IX). Human Factor VIII has the accession number NM_000132.3 and Human Factor IX has the accession number NM_000133.3.

Other exogenous genes may be utilized in the treatment of other platelet related conditions. In some embodiments, exogenous genes useful in the treatment of diseases other than platelet related disorders are utilized (e.g., in the treatment of cancer by using platelets to target release of anti-neoplastic agents "i.e. IL-24" to shrink solid tumors and anti-thrombotic agents to be released at the site of blood clots such as cases of deep vein thrombosis).

C. Targeting Factors and Enhancers

In some embodiments, expression cassettes further comprise a targeting factor that targets expression into a particular sub-structure of a platelet. In some embodiments, expression cassettes further comprise the minimal amino acid sequence of a signal sequence peptide that has been found to be able traffic not only VWF but also recombinant proteins fused to the peptide that has the proven ability to store proteins in cellular granule compartments specifically the natural storage sub-structure endothelial cells "Weibel-Palade bodies" and platelet α-granules, both of which can be secreted upon cellular activation. For example, in some embodiments, expression constructs comprise a nucleic acid encoding a Von Willebrand Factor propeptide signal peptide and D2 domain (SPD2) to promote trafficking of molecules directly into the α-granule compartment as shown in Rosenberg J B et al, Intracellular Trafficking of FVIII to von Willebrand Factor storage Granules, J. Clin. Invest. 101, 613-624 (1998); Haberichter S L, Jacobi P, Montgomery R R. Critical independent regions in the VWF propeptide and mature VWF that enable normal VWF storage. Blood 2003, 101(4): 1384-1391 and Haberichter et al, The Von Willebrand Factor Propeptide (VWFpp) Traffics an Unrelated Protein to Storage, Arterioscler Thromb Vas Biol. 22, 921 926 (2002).

An example of an expression cassette comprising a 673 bp fragment of the ITGA2B gene promoter and a VWF/SPD2 gene is shown in FIG. 7 (SEQ ID NO:24). Variants of these sequences that retain its desired activity are specifically contemplated for use in compositions and methods of embodiments of the present invention.

In some embodiments, constructs comprise an expression enhancer (e.g., Woodchuck Hepatitis Virus (WHP) Posttranscriptional Regulatory Element (WPRE)) between the promoter/signaling cassette and the exogenous gene of interest. This element has been utilized by several gene transfer strategies because its structure inhibits degradation of the transcript within the cell and thus allows for more therapeutic protein to be synthesized compared to a gene transfer vector in the absence of WPRE.

D. Vector Backbones

The present invention is not limited to a particular expression vector. In some embodiments, vectors are self-inactivating. In some embodiments, vectors are retroviral vectors (e.g., lentiviral vectors). Table 2 provides a summary of exemplary suitable vectors.

Second, following the construction of the recombinant vector, the vector DNA is introduced into a packaging cell line. Packaging cell lines provide viral proteins required in

TABLE 2

| Virus | Advantages | Disadvantages |
|---|---|---|
| Adenovirus | High titer<br>High gene expression<br>Can infect non-dividing cells<br>Accepts very large cassettes (40 kb) | Immunogenic<br>Does not integrate into genome |
| Adeno-associated virus | Can infect non-dividing cells<br>Relatively safe in humans | Accepts small cassettes (4 kb)<br>Low transduction efficiency in hematopoietic cells |
| Alphavirus (Sindbis) | Can infect non-dividing cells<br>High titer<br>High transduction efficiency<br>High gene expression | Toxic to cells<br>Does not integrate into genome |
| Lentivirus | Stably incorporated into genome<br>Can infect non-dividing cells | New to field<br>Safety uncertain in humans |
| Retrovirus | Stably incorporated into genome<br>Relatively safe in humans<br>High titer<br>Accepts large cassettes (8 kb) | Infects only dividing cells |

Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (e.g., surrounded by a host cell-derived lipid bilayer membrane) single-stranded RNA viruses that infect animal cells. When a retrovirus infects a cell, its RNA genome is converted into a double-stranded linear DNA form (e.g., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses has allowed the adaptation of the retroviral genome to produce retroviral vectors. The production of a recombinant retroviral vector carrying a gene of interest is typically achieved in two stages. First, the gene of interest is inserted into a retroviral vector which contains the sequences necessary for the efficient expression of the gene of interest (including promoter and/or enhancer elements which may be provided by the viral long terminal repeats [LTRs] or by an internal promoter/enhancer and relevant splicing signals), sequences required for the efficient packaging of the viral RNA into infectious virions (e.g., the packaging signal [Psi], the tRNA primer binding site [−PBS], the 3' regulatory sequences required for reverse transcription [+PBS] and the viral LTRs). The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); the resulting virus is said to be replication defective.

trans for the packaging of the viral genomic RNA into viral particles having the desired host range (e.g., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus [VSV]). The transfected packaging cell will then produce viral particles that contain the membrane-associated protein expressed by the transfected packaging cell line; these viral particles, which contain viral genomic RNA derived from one virus encapsidated by the envelope proteins of another virus are said to be pseudotyped virus particles.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

Commonly used recombinant retroviral vectors are derived from the amphotropic Moloney murine leukemia virus (MoMLV) (Miller and Baltimore, Mol. Cell. Biol., 6:2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the viral proteins required for particle assembly (Markowitz et al., J. Virol., 62:1120 [1988]).

Despite these advantages, existing retroviral vectors based upon MoMLV are limited by several intrinsic problems: 1) they do not infect non-dividing cells (Miller et al., Mol. Cell. Biol., 10:4239 [1992]), 2) they produce low titers of the recombinant virus (Miller and Rosman, BioTechn., 7: 980 [1989]; and Miller, Nature 357: 455 [1992]) and 3) they infect certain cell types (e.g., human lymphocytes) with low efficiency (Adams et al., Proc. Natl. Acad. Sci. USA 89:8981 [1992]). The low titers associated with MoMLV-based vectors has been attributed, at least in part, to the instability of the virus-encoded envelope protein. Concentration of retrovirus stocks by physical means (e.g., ultracentrifugation and ultrafiltration) leads to a severe loss of infectious virus.

Other commonly used retrovectors are derived from lentiviruses including, but not limited to, human immunodeficiency virus (HIV) or feline immunodeficiency virus (FIV). Lentivirus vectors have the advantage of being able to infect non replicating cells.

The low titer and inefficient infection of certain cell types by retro vectors has been overcome by the use of pseudotyped retroviral vectors which contain the G protein of VSV as the membrane associated protein. Unlike retroviral envelope proteins which bind to a specific cell surface protein receptor to gain entry into a cell, the VSV G protein interacts with a phospholipid component of the plasma membrane (Mastromarino et al., J. Gen. Virol., 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al., Proc. Natl. Acad. Sci. USA, 90:8033 [1993]).

The VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV.

The present invention is not limited to the use of the VSV G protein when a viral G protein is employed as the heterologous membrane-associated protein within a viral particle. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus human immunodeficiency virus, and other lentiviral vectors.

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J., 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

The present invention is not limited to retroviral vectors. Large numbers of suitable vectors are known to those of skill in the art, and are commercially available. Such vectors include, but are not limited to, the following vectors: 1) Bacterial—pQE70, pQE60, pQE 9 (Qiagen), pBS, pD10, phagescript, psiX174, pbluescript SK, pBSKS, pNH8A, pNH16a, pNH18A, pNH46A (Stratagene); ptrc99a, pKK223 3, pKK233 3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some embodiments of the present invention, mammalian expression vectors comprise, along with an expression cassette as described herein, an origin of replication, any necessary ribosome binding sites, polyadenylation sites, splice donor and acceptor sites, transcriptional termination sequences, and 5' flanking non transcribed sequences. In other embodiments, DNA sequences derived from the SV40 splice, and polyadenylation sites may be used to provide the non-transcribed genetic elements.

II. Therapeutic Methods

In some embodiments, the present invention provides systems and methods for genetic manipulation of stem cells (e.g., hematopoietic stem cells or cancer stem cells). In some embodiments, the compositions and methods described herein find use in the treatment of a variety of disorder related to platelet function (e.g., hemophilia and the disorders described in Table 3 below).

There have been several bleeding disorders characterized by molecular genetic defects of platelet membrane, cytoplasmic and granular proteins that usually lead to prolonged bleeding events. While each disorder is rare, maybe occurring in 1:1,000,000 individuals (e.g. Glanzmann Thrombasthenia), taken collectively, an inherited platelet defect occur in 1:20,000 people worldwide as described in Wilcox, D. A. White II, G. C, Gene therapy for platelet disorders: studies with glanzmann's thrombasthenia. Journal of Thrombosis and Haemostasis. 1: 2300-2311, (2003) and Wilcox, D. A., White II, G. C: Gene therapy for platelet disorders. In: Platelets. Second Edition, A. D. Michelson (ed.), Academic Press, San Diego, Chapter 71: 1313-1325, (2007) and Third Edition, Chapter 64: In Press (2012). In addition to inherited platelet defects, hematopoietic stem cell gene therapy aimed at targeting therapeutic agents to the platelet surface, cytoplasm or granules finds use as a strategy to correct other disorders of hemostasis, thrombosis, immune response and cancer.

TABLE 3

| Inherited Disorder | Defect | Function Disrupted |
| --- | --- | --- |
| G-Protein Disorder | $G_{\alpha q}$, $G_{\alpha i1}$ | Activation |
| ADP Receptor Defect | $P2Y_{12}$ | Activation |
| Bernard-Soulier Syndrome | Glycoprotein Ib-IX | Adhesion |
| Collagen Receptor Deficiency | Glycoproteins Ia-IIa | Adhesion |
| Glanzmann Thrombasthenia | Glycoproteins IIb-IIIa | Aggregation |
| Gray Platelet Syndrome | NBEAL2 | α-Granule Formation/Storage |
| QuebecPlatelet Disorder | Urokinase plasminogen activator | α-Granule Storage |
| Scott Syndrome | Phosphatidylserine Translocation | Coagulation |
| May-Hegglin Anomaly Fechtner Syndrome Sebastian Platelet Syndrome Epstein Syndrome | MYH9 | Cytoskeleton/Platelet Formation |
| Wiskott-Aldrich Syndrome | WAS Protein | Cytoskeleton |
| Chediak-Higashi Syndrome | CHS protein | Dense Body Formation/Storage |
| Hermansky-Pudlak Syndrome | HPS1, HPS3-7, AP-3 | Dense Body Formation/Storage |
| Thromboxane Deficiency | Thromboxane $A_2$ | Signal Transduction |

In some embodiments, therapeutic methods are ex vivo methods, in which autologous hematopoietic stem cells are harvested from an animal (e.g., human) in need of treatment, modified using one of the vector described herein, and re-introduced into the original donor. Such autologous methods reduce the risk of autoimmune or rejection responses that can occur with infusion of donor clotting factors and allow one to limit gene transduction to hematopoietic stem cells through ex vivo transduction.

An exemplary method for ex vivo modification of hematopoietic stem cells is described in Aiuti et al. (Science 341:865 (2013; herein incorporated by reference in its entirety). For example, in some embodiments, the method includes the steps of administering cytokines to mobilize peripheral blood stem cells into the peripheral blood; performing apheresis and magnetic bead selection for CD34+ cells; preconditioning using e.g., bulsulfan and/or other agents like fludarabine; and using a viral (e.g., lentiviral) gene transfer vector to modify stem cells before they are re-introduced into the patient.

In some embodiments, hematopoietic stem cells are mobilized using administration of cytokines or other mobilization agents (See e.g., Fu et al., Blood Rev. 2000 December; 14(4):205-18 and U.S. Pat. No. 7,417,026, each of which is herein incorporated by reference in its entirety for a discussion of mobilization protocols), although other suitable protocols may be utilized.

For example, in some embodiments, mobilization cytokines include, but are not limited to, Interleukin-3 (IL-3), granulocyte colony stimulating factor (G-CSF), also known as Amgen's FDA approved drug Neupogen, stem cell factor (SCF), granulocyte macrophage colony-stimulating factor (GM-CSF), and sequential or co-administration of one or more of IL-3, GM-CSF, SCF, and GM-CSF.

Suitable dosage ranges for mobilization agents vary, but in general, the compounds are administered in the range of about 0.1 μg/kg-5 mg/kg of body weight; preferably the range is about 1 μg/kg-300 μg/kg of body weight; more preferably about 10 μg/kg-100 μg/kg of body weight. For a typical 70-kg human subject, thus, the dosage range is from about 0.7 μg-350 mg; preferably about 700 μg-21 mg; most preferably about 700 μg-7 mg. Dosages can be higher when the compounds are administered orally or transdermally as compared to, for example, i.v. administration. The compounds can be administered as a single bolus dose, a dose over time, as in i.v. or transdermal administration, or in multiple dosages.

The amount of active compound to be administered can vary according to the discretion of the skilled artisan. The amount of active compound to be administered to the recipient is within the ranges described above for stem cell mobilization. However, the administration of such amounts will vary according to the standards set forth by clinicians in the field of stem cell enhancement therapy.

Following mobilization, CD34+Peripheral Blood stem cells (PBC) are isolated from the low molecular weight mononuclear cells by immunomagnetic beads using Miltenyi's automacs system (for large animal, dogs, 25-45 kg) and Miltenyi's Clinimacs system (for humans) recently approved for clinical use by the FDA. The CD34+PBC are the genetically modified using the vectors described herein and re-introduced into a subject in need by autologous stem cell transplant. In some embodiments, a single treatment is utilized to provide long-term protection against episodes of bleeding. In some embodiments that treat hemophilia, treatment is performed on a regular basis (e.g., weekly, monthly, yearly, once every 2, 3, 4, 5 or more years, and the like) in order to prevent episodes of bleeding. In some embodiments, treatment is only administered when episodes of abnormal bleeding occur (e.g., following accidents, prior to or following surgery, etc,). In some embodiments, maintenance therapy is administered in combination with extra therapy when episodes of abnormal bleeding occur.

EXPERIMENTAL

The following examples are provided in order to demonstrate and further illustrate certain preferred embodiments and aspects of the present invention and are not to be construed as limiting the scope thereof.

Example 1

Materials and Methods
Cell Lines

Human transformed cell lines were obtained from American Type Culture Collection (Rockville, Md.) and propagated under conditions described for promegakaryocytic (*HEL Megakaryocyte transformed cell line*) (Bray, P. F. et al. J Clin Invest 80, 1812-1817. (1987); Greenberg, S. M., et al., *T-cell lymphoma* (*KT*1), (Okamoto, T., et al. J Biol Chem 261, 4615-4619 (1986)) *B-cell lymphoma* (*Raji*), (Choi, J. H. et al. International immunopharmacology 8, 852-858, 2008.01.037 (2008)) *Erythroleukemia* (*K562*), (Gauwerky, C. & Golde, D. W. Blood 56, 886-891 (1980)) and *Epithelial (HeLa)* (Goldstein, M. N., et al., Annals of the New York Academy of Sciences 89, 474-483 (1960)) cell lines.

Luciferase Reporter Gene Promoter Vectors

ITGA2B Gene Promoter Constructs: Genomic DNA was isolated from the human pro-megakaryocyte cell line, Dami,49 and human ITGA2B gene promoter fragments were amplified by PCR using either sense primer "−1218" (5'-TTACGCGTCGACAGATCTAAATGTGGCTGGTTAC-CCC-3')"−1198" (SEQ ID NO:1) (bold) of ITGA2B or "−889" (5'-TTACGCGTCGACAGATCTGTGCTCAAT-GCTGTGCC-3')"−872" (SEQ ID NO:2) (bold) of ITGA2B, or "−673" (5'-TTACGCGTCGACAGATCTCCTTGCCAC-CTAGACC-3')"−654" (SEQ ID NO:3) (bold) of ITGA2B and anti-sense primer (5'-GGCGTCTTCCATGGTCCT-TCTTCCACAACC-3') (SEQ ID NO:4) encoding nucleotides +99 to +86 of luciferase pGL3-BASIC and nucleotides +30 to +15 (bold) of ITGA2B gene promoter. Correct identity of constructs was confirmed by nucleotide sequence analysis.

pCMVLuc: A BglII and HindIII restriction digest of cytomegalovirus tissue non-specific gene promoter (878 bp) from pRc/CMV (Invitrogen) is ligated into the pGL3-Basic Luciferase vector (Promega, Madison, Wis.). This construct served as the positive control for high level gene expression within all cell-types; thus, assigned an arbitrary level of 100% luciferase activity for each cell line (FIG. 1).

pGL3-BasicLuc: Negative control construct for 0% luciferase activity (FIG. 1) because lacks a gene promoter to drive luciferase gene transcription (Promega).

pCMVnlac: Cell lines were co-transfected with one of the pITGA2BLuc+constructs and pCMVnlac encoding the β-galactosidase marker gene to normalize transgene expression (Wilcox et al., *Proc Natl Acad Sci USA* 1999, 96(17): 9654-9659.

Luciferase Gene Promoter Reporter Assay

Cell lines ($2 \times 10^7$) were co-transfected with either (20) μg) of the ITGA2B gene promoter construct (−1218, −889, −673) (FIG. 1A) or the positive (CMV) or negative (Basic) controls encoding firefly luciferase and pCMVnlac (20 μg) encoding β-galactosidase.49 Briefly, forty-eight hours after co-transfection cells were washed, harvested, and lysates were prepared and frozen to −80° C. using the luciferase assay system (Promega). Luciferase activity was measured with a Turner Designs Model 20 Luminometer. Detection of β-galactosidase activity was performed to normalize transient transgene expression for each cell line with a sensitive ELISA enzymatic assay that measured colormetric change with the substrate for β-galactosidase, chlorophenol red β-D-galactophranoside (CPRG) (Eustice D C, et al., *Biotechniques* 1991, 11(6): 739-740, 742-733). The percent of luciferase activity was determined by comparing the mean value of the Relative Light Units (RLU) of luciferase/CPRG Vmax value for each construct to reveal the transfection efficiency for each cell line. The RLU for pCMVLuc was assigned arbitrarily a value of 100% and all other results were calculated for each vector based upon that value as shown in FIG. 1A.

ITGA2B Promoter Driven Lentiviral Vector for Human BDDFVIII

ITGA2B-(M)WPTS genetic transfer vectors are derived from a HIV type-1 lentiviral vector (D.Trono, University of Geneva, Switzerland).51 p-889ITGA2B-BDDFVIII-WPTS lentiviral vector (FIG. 1B) encodes a −889 to +30 nucleotide fragment of the human ITGA2B promoter and human BDD-FVIII molecule.16 p-673ITGA2B-VWFSPD2-BDDFVIII-WPTS lentiviral vector (FIG. 1C) encodes a fragment of the human ITGA2B gene promoter from nucleotide −673 to +30 followed by a fragment of the human Von Willebrand Factor propeptide (VWFpp encoding 540 amino acid VWF signal peptide (SP; 66 bp) linked to the D2 domain (1,199 bp) and cDNA encoding human BDDFVIII to allow megakaryocyte-specific transcription of a hybrid molecule that uses the SPD2 peptide to traffic human BDDFVIII to platelet α-granules.22 cDNA encoding SP was amplified by PCR with forward Primer (P)1(5'GTTAATCGATATCTCCTTGC-CACCTAGA3') (SEQ ID NO:5), and reverse P2(5'AATCTGGCAGGAATCATGGTCCTTCTTCCA-CAACCT3') (SEQ ID NO:6) and ligated to D2 amplified by PCR using forward P3(5'AGGTTGTGGAAGAAGGAC-CATGATTCCTGCCAGATTTGC3') (SEQ ID NO:7) and reverse P4(5'CGTCTCGGCCCTTTTGCTGCCAT-GAGACAG3') (SEQ ID NO:8). A nested PCR linked ITGA2B promoter and VWFSPD2 with P5(5'ATCGA-TATCTCCTTGCCACCT A3') (SEQ ID NO:9) and P4. p-889ITGA2-BDDFVIII-WPTS served as a template for PCR of cDNA encoding a fragment of BDDFVIII using forward P7(5'CGTCTCAGGGCCACCAGAAGATAC-TACCT3') (SEQ ID NO:10) and reverse P8(5'ACGCGTCT-TCTCTACATACTAGTA3') (SEQ ID NO:11) to synthesize cDNA that ligated directly to VWFD2. All PCR products were cloned into pCR-Blunt II-TOPO (Life Technologies, Grand Island, N.Y.) using unique restriction sites −673ITGA2B-SPD2(ClaI and BsmBI) ligated to 5'hBDD-FVIII (BsmB1 and MluI) with 3'BDDFVIII (MluI and SpeI). All fragments were cloned into pWPTS lentiviral vector and the correct identity confirmed by nucleotide sequence analysis. Recombinant virions were generated from three-plasmid transient co-transfection followed by supernatant collection, 500-fold concentration by centrifugation, and storage at −80° C. until utilized (Fang J, et al., Proc Natl Acad Sci USA 2011, 108(23): 9583-9588). Virion titer was determined by RT-PCR (Lizee G, et al., *Hum Gene Ther* 2003, 14(6): 497-507). Replication-competent virions were confirmed absent from stocks with marker rescue assays (Wilcox et al., *Blood* 2000, 95(12): 3645-3652).

Dogs

Cytokine mobilized CD34+G-PBC gene transfer and autologous transplant studies using FVIII-Deficient dogs affected with hemophilia A (University of North Carolina, Chapel Hill, N.C.) (Lozier J N, et al., *Proc Natl Acad Sci USA* 2002, 99(20): 12991-12996) were conducted and approved by Institutional Animal Care and Use Committees of the University of North Carolina and The Medical College of Wisconsin which are both accredited facilities of the American Association for Accreditation of Laboratory Animal Care.

Canine CD34+G-PBC Isolation, Transduction, Transplantation

19 Adult (1.25, 4.25, and 6.5 year old) FVIII-Deficient male dogs were injected daily with canine recombinant granulocyte colony stimulating factor (crG-CSF; 10 μg/kg/d) and stem cell factor (crSCF; 5 μg/kg/d) (Amgen, Thousand Oaks, Calif.). G-PBC collection was performed on the third day using a COBE Spectra Blood Cell Separator. Mononuclear G-PBC were isolated with Fico-Paque Plus (GE Healthcare, Uppsala, Sweden). CD34+G-PBC were selected with a biotin-conjugated-1H6 Ab (1 mg/ml) (Richard Nash, Fred Hutchinson Research Institute, Seattle, Wash.) and anti-biotin immuno-magnetic beads (1:5 dilution) on an Automacs magnetic cell separator (Miltenyi Biotec Inc., Auburn, Calif.). CD34+G-PBC were transduced with −889ITGA2B-BDDFVIII-WPTS or −673ITGA2B-VWFSPD2-BDDFVIII-WPTS lentiviral vector. Briefly, 4×106 cells/well were seeded in a 6-well plate (Falcon-Becton Dickinson, Franklin Lakes, N.J.) coated with 20 µg/cm2 RetroNectin (Takara Shuzo, Otsu, Shiga, Japan) and incubated with 1.0×10$^4$ ITGA2B-FVIII lentivirions/cell in X-Vivo 10 containing 10% FCS, rhIL-3, rcaIL-6, rcaSCF, rhTPO and rhflk2/flt3 ligand. Approximately 3×106 FVIII-transduced CD34+G-PBC/kg and 2×108 CD34(−)G-PBC were infused into the cephalic vein of each autologous transplant recipient pre-conditioned with a non-myeloablative dose of 5-10 mg/kg Busulfex®. Transient immune suppression administered for ≈90 days after transplant with 10 mg/kg/d cyclosporine (Gengraf®, Abbott Laboratories, North Chicago, Ill.) and 8 mg/kg/d MMF (Table 1) (Fang et al., *Proc Natl Acad Sci USA* 2011, 108(23): 9583-9588).

Blood Collection

Blood was collected at preselected times into a vacutube containing 7.5% EDTA anticoagulant (Fang et al., supra). Blood cells were counted on a Vet ABC hematology analyzer (scil animal care company, Gurnee, Ill.). Platelets were isolated with Fico/Lite™ (Atlanta Biologicals, Norcross, Ga.), washed with PBS and used directly for immunofluorescent flow cytometry or FVIII:C activity analysis. Leukocytes were isolated with Ficoll-Paque Plus® (GE Healthcare) according to the manufactures specifications.

Antibodies

A murine monoclonal 1° Ab to canine CD34 "1H6" (1 mg/ml) was from the Fred Hutchinson Cancer Research Center (Seattle, Wash.).27 A sheep anti-rabbit fibrinogen polyclonal 1° Ab (5 µg/ml) that recognizes canine fibrinogen was purchased from (Enzyme Research). Monoclonal 1° Abs (5-10 µg/ml), MBC 103.3 and 301.3 (R. R. Montgomery, BloodCenter of WI, Milwaukee, Wis.), recognize epitopes on human BDDFVIII.53 2° Abs used were Alexa Fluor® 488 F(ab')2 conjugated to a fragment of donkey anti-sheep IgG (H+L) (1:1,000 dilution) and Alexa Fluor® 568 F(ab')2 fragment of goat anti-mouse IgG (H+L) (1:500 dilution) were from Life Technologies (Grand Island, N.Y.).

Immunofluorescent Confocal Microscopy

Canine platelets were fixed with 3.7% (vol/vol) buffered formalin, permeabilized in 0.5% Triton X-100 (in 20 mmol/L Hepes, 300 mmol/L sucrose, 50 mmol/L NaCl, and 3 mmol/L MgCl2, pH 7.0), and blocked with 2.5% normal goat serum in HBSS. Platelets were incubated with a sheep polyclonal 1° Ab to canine fibrinogen and monoclonal 1° Ab (MBC 103.3 & 301.3) to human FVIII (5 ug/ml) overnight at 4° C.53 The Alexa Fluor® 488-conjugated F(ab')2 fragment of donkey anti-sheep IgG (H+L) was used as a 2° Ab (1:1,000 dilution) to detect fibrinogen and Alexa Fluor® 568-conjugated F(ab')2 fragment of goat anti-mouse IgG (H+L) conjugated 2° Ab (1:500 dilution) was used to detect the presence of FVIII for 30 min at 25° C. Platelets were mounted with Vectashield (Vector Labs, Burlingame, Calif.). Immunofluorescence was detected with a Zeiss LSM 510 Multiphoton Confocal Microscope (Carl Zeiss, Inc. Oberkochen, Germany) (Wilcox D A, et al., *Journal of thrombosis and haemostasis: JTH* 2003, 1(11): 2300-2311). Platelets isolated from FVIII-Deficient dogs were used as negative controls. Nonspecific isotype control Ab served as negative controls. Platelets were imaged by Z sections taken for each field and the entire Z series (12-25 images) combined into a stacked projection. The projections were merged using the Confocal Assistant software program (Bio-Rad). Computer-assigned colors were based on the intensities of bitmap overlaps, with Alexa488-fluorochrome represented by green pixels, Alexa568-fluorochrome represented by red pixels, and co-localization of the two fluorochrome-conjugated antibodies represented by yellow pixels.

Immunofluorescent Flow Cytometry

Canine platelets were isolated from blood and treated with Cytofix™ and PERM/WASH™ reagents (BD Biosciences) for intracellular detection of BDDFVIII. Platelets were incubated with a monoclonal 1° Ab (MBC 103.3 & 301.3) to human FVIII (5 ug/ml) 30 minutes at 4° C. and then incubated with Alexa Fluor® 568-conjugated F(ab')2 fragment of goat anti-mouse IgG (H+L) conjugated 2° Ab (1:500 dilution) for 30 minutes at 4° C. Platelets isolated from FVIII-Deficient dogs were used as negative controls. Non-specific isotype control Ab served as negative controls. Cells were collected and analyzed on an Accuri® C6 Flow Cytometer (Accuri Cytometers, Inc., Ann Arbor Mich.) using the Accuri analysis software.

Immunogold Labeling

Platelets were fixed in 1.25% glutaraldehyde (Fluka A G, Buchs, Switzerland), infused with 2.3M sucrose (Fluka), and frozen with a Reichert KF 80 freezing system (Leica, Vienna, Austria). Sections of ≈80 nm were prepared with the Ultracut E ultramicrotome equipped with a FC 4E cryokit attachment and placed on collodion-coated nickel grids. Grids were incubated for 10 min on PBS with 1% BSA and then placed on (10 µg/ml) drops of the 1° Ab to FVIII (301.3) for 1 h at 25° C. Sections were incubated for 1 h with a goat anti-mouse 2° Ab adsorbed onto 10 nm gold particles (1/100 dilution of AuroProbe EM G10). Controls included the use of an irrelevant IgG of the same species and at the same concentration.

Electron Microscopy

Grids were stained by uranyl acetate and osmium and then embedded in methylcellulose prior to observation with a Jeol JEM-1010 transmission electron microscope (Jeol, Croissy-sur-seine, France) at 80 KV.

Agonist Induced Activation of Platelets

Platelets were isolated from circulating peripheral blood, washed, and activated with physiological agonists of platelet activation. To induce activation, platelets were resuspended in Tyrode's buffer (2.5×106/ml) containing 1 mM CaCl2, 1 mM MgCl2, 25 µM each of adenosine diphosphate (ADP) (Sigma), epinephrine (Bio/Data Corporation, Horsham, Pa.) and canine thrombin receptor activating peptides: PAR1 (SFFLKN-NH2), PAR3 (TRFGAP-NH2) and PAR4 (SF-PGQP-NH2) for 30 minutes at 37° C. as previously described (Fang et al., supra). Separate aliquots were incubated in Tyrode's buffer without agonist as a negative control. The platelets were pelleted by centrifugation and supernatant was aspirated and discarded from agonist treated and negative control samples. The platelet pellet was frozen immediately to −80° C. until tested for FVIII:C activity using the coatest assay.

PCR Detection of Lentiviral Vector in Blood Genomic DNA

Figure 5:
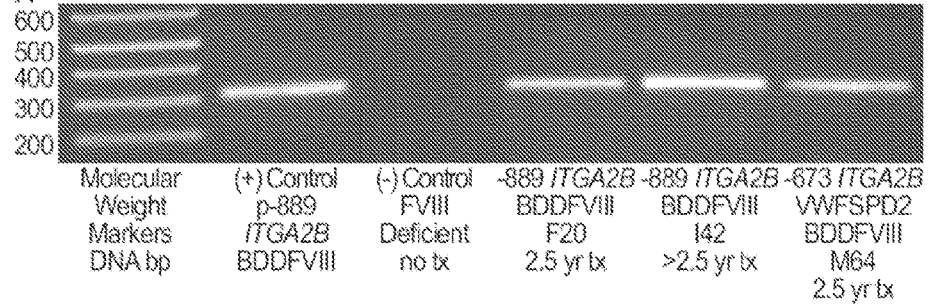
FIG. 5 shows PCR analysis for detection and localization of lentiviral vector within canine genome. (A) long-term detection of BDDFVIII-lentiviral vector within leukocyte genomic DNA. (B) linear amplification-mediated (LAM)-PCR to localize lentiviral vector within canine genome.
Figure 5:
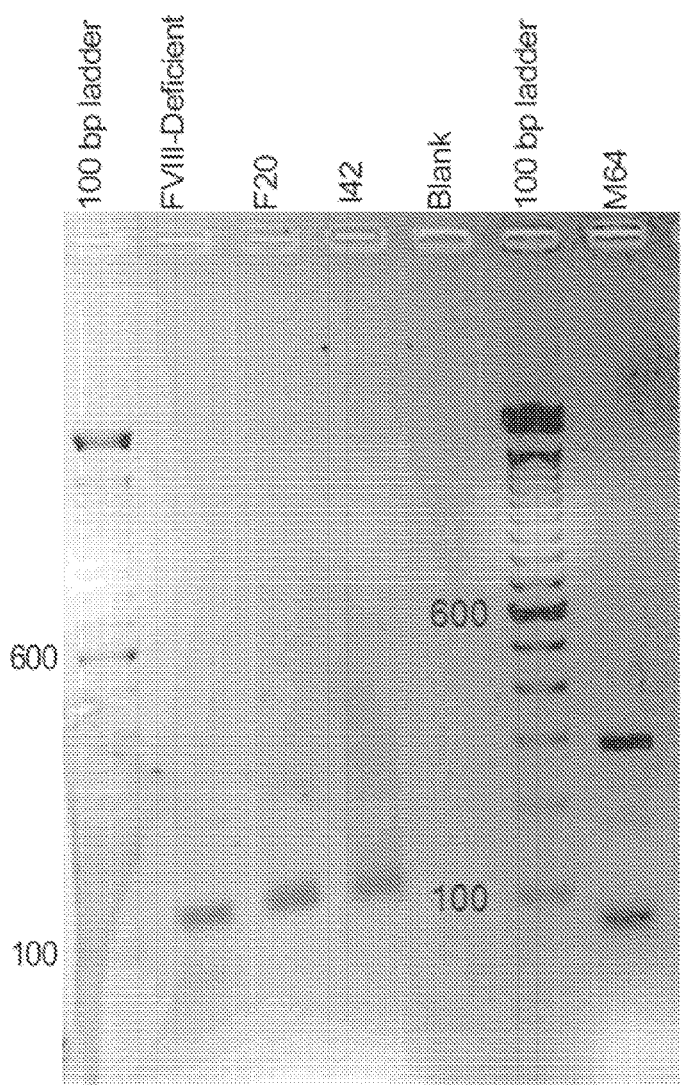

DNA was isolated with a QIAamp® DNA Blood Mini Kit (Qiagen, Md., USA) from canine leukocytes purified with Ficoll-Paque™ Plus (Amersham Pharmacia Biotech AB, Uppsala, Sweden). p-889ITGA2-BDDFVIII-WPTS served as a positive control. PCR analysis was performed with Taq polymerase (Invitrogen, Carlsbad, Calif.) on a PTC200 instrument (MJ Research, Watertown, Mass.) with forward primer P1(5'-ACGCTATGTGGATACGCTG-3') and reverse primer P2(5'-AACACCACGGAATTGTCAG-3') (SEQ ID NO:12) to synthesize a 318 nucleotide primary product encoding the WPRE (FIG. 1B,C). A secondary PCR reaction was performed with nested forward primer P3(5'-TGGA-TACGCTGCTTTAATGC-3') (SEQ ID NO:13) and reverse primer P4(5'-AATTGTCAGTGCCCAACAG-3') (SEQ ID NO:14) encoding a 302 bp product of WPRE (FIG. 5A).

RT-qPCR to Detect Lentiviral Transduction Efficiency

Percent lentiviral gene marking was measured by RT-qPCR using BIO-RAD CFX96 Real-Time System.52 Briefly, 12.5 ul of TaqMan Universal PCR Master Mix (Life technologies), a 900 nM concentration of each primer, and 200 nM probe were combined in 20 µl of water. Then 5 ul of canine genomic DNA was added and PCR utilized 2 min at 500 C, 10 min at 950 C, and then 40 cycles of 15 sec at 950 C and 1 min at 600 C. For each RT-qPCR, a no template control was included as negative control. Each sample was analyzed in triplicate for gene copy number using Primer Express software (version 1.0; Applied Biosystems) and the mean value for transgene copy number/genome was converted to percent peripheral blood cells positive for lentiviral vector (also known as transduction efficiency) and reported in Table 1 Column 8. The lentiviral LTR primers and probe used were: Fwd:5'-AGCTTGCCTTGAGTGCTTCA-3' (SEQ ID NO:15); Rev:5'-TGACTAAAAGGGTCT-GAGGGA-3'(SEQ ID NO:16); probe:6FAM-TGC-CCGTCTGTTGTGTGACTCTG-MGBNFQ (SEQ ID NO:17). The canine ITGB3 gene was used as an endogenous control for gene copy number with Fwd:5'-ATGCATC-CCACTTGCTGGTAT-3'(SEQ ID NO:18); Rev:5'-TGC-CCATCGTTAGGTTGG-3'(SEQ ID NO:19); probe:6FAM-TGCCTGCCAGCCTTCCATCCAG-MGBNFG (SEQ ID NO:20). Copy number was based on TaqMan principle. Ten-fold serial dilution of the plasmid constructs of known concentration containing relevant sequences (Lentiviral vector LTR and canine ITGB3) were used to create standard curves for quantification of samples.

Linear Amplification-Mediated (LAM)-PCR

LAM-PCR was performed to localize the lentiviral vector insertion sites within genomic DNA isolated from peripheral blood leukocytes. Briefly, the junction between integrated proviral LTR and the host genome was selected by 2 rounds of linear PCR [95° C. for 5 min; (95° C. for 1 m, 60° C. for 45 s, 72° C. for 90 s)×50; 72° C. for 10 m] with a vector-specific 5'-biotinylated primer [5'-/biotin/-GAAC-CCACTGCTTAAGCCTCA-3'(SEQ ID NO:26)] and purified using streptavidin-coated magnetic beads [Dynal M-280]. Products were double stranded using Klenow polymerase and random hexanucleotide primers and digested with Tsp5091 at 65° C. for 2 h. Directional double-stranded linker oligos were ligated onto the non-LTR end and the resulting products were amplified by nested PCR [95° C. for 5 min; (95° C. for 1 m, 60° C. for 45 s, 72° C. for 90 s)×35; 72° C. for 10 m] using LTR-specific forward primers [F1: 5'-/biotin/-AGCTTGCCTTGAGTGCTTCA-3'(SEQ ID NO:27); F2: 5'-AGTAGTGTGTGCCCGTCTGT-3'(SEQ ID NO:28)] and linker cassette specific reverse primers [R1: 5'-GACCCGGGAGATCTGAATTC-3'(SEQ ID NO:29); R2: 5'-AGTGGCACAGCAGTTAGG-3'(SEQ ID NO:30)]. Between rounds of nested PCR, products were purified using streptavidin-coated magnetic beads. Products were visualized on 2% TAE agarose gels. For sequencing, products were gel purified and cloned into pCR2.1-TOPO, transformed into *E. coli* Top10, selected on LB-Amp-Xgal plates, and amplified by colony PCR using M13F/R.

Functional Assessment of Integration Sites

Sequence products from LAM-PCR that were verified to contain proviral LTR sequence were masked for known genomic repeats and proviral features. The resulting sequence was aligned to the dog genome (CanFam 2.0, May 2005 assembly) using the Blat (BLAST-like alignment tool) server at UCSC. Sequences mapping to a unique location in the genome at 95% similarity were selected and integration sites were determined as the base in the genomic alignment flanking the proviral LTR sequence. For each site, the closest RefSeq gene was determined and compared to a list of human cancer orthologs.

Detection of Biologically Active Human FVIII (FVIII:C)

Lysates of $1\times10^8$ platelets/ml were tested for FVIII:C using a Chromogenix Coatest® SP4 FVIII kit (DiaPharma, Franklin, Ohio).12 Duplicate samples of supernatant were placed in uncoated wells of a 96-well microtiter plate (25 µl/well) and assay components (phospholipid, Factor IXa, Factor X, and calcium chloride) were added, and incubated for 10 min at 37° C. The chromogenic Factor Xa substrate S-675 was added, and the plate was transferred to a Wallac Victor2 microplate reader preset at 37° C. The Factor Xa-dependent conversion of S-2675 is directly related of the amount of FVIII:C in each well. A standard curve was constructed by plotting known amounts of recombinant human FVIII (Kogenate; Bayer Healthcare Pharmaceuticals, Berkeley, Calif.) diluted in platelet lysate buffer using Vmax at 405 nm. The Vmax of each reaction was converted to units of FVIII:C activity using the kinetic software program, SOFTmax, v.2.34 (Molecular Devices). The FVIII activity was measured by an endpoint reading at 405 nm, a background reading at 490 nm was subtracted from 405 nm. The total maximum FVIII:C/dog was calculated by multiplying the mean FVIII:C U/ml/1×108 platelets×92 ml blood/kg× dog weight (kg)×(2×10$^8$ platelets)/1 ml blood) using measured values recorded in Table 1 and FIG. 6.

Whole Blood Clotting Time (WBCT) Assay

WBCT is a modification of the Lee-White clotting time using two siliconized glass tubes (Becton-Dickinson, Rutherford, N.J.) at 28° C. (Nichols T C, et al., *J Thromb Haemost* 2012, 10(3): 474-476). One ml of whole blood was drawn and 0.5 ml blood was distributed into each tube. A timer was started. After one minute, one tube was tilted every 30 sec, the other left undisturbed. When a clot formed in the tilted tube, the second tube was then tilted every 30 sec until a clot formed. The time for formation of a fully gelled clot in the second tube was recorded as the WBCT. Blood was collected from a hemostatically normal (WBCT 7.5-12.5 min) and the three experimental dogs (F20,I42,M64) before and after G-PBC transplant if animals had not been treated with plasma for at least one month.

Inhibitor Assay to Detect Immune Response to Human FVIII

Canine blood plasma (F20, I42 and M64) was screened for inhibitors with an activated partial thromboplastin time (aPTT) mixing assay that detects inhibitory antibodies to either coagulation factor VIII or IX as previously described (Langdell R D, et al., *J Lab Clin Med* 1953, 41(4): 637-647; Sahud M A. *Semin Thromb Hemost* 2000, 26(2): 195-203; Matrai J, et al., *Hepatology* 2011, 53(5): 1696-1707). Briefly, test plasmas are incubated in a 1:1 mix with normal plasma for 2 h at 37° C. and then the incubated mixture is analyzed using standard aPTT reagents. Plasma from hemophilia A dogs with known Bethesda Inhibitor (BIU) titers that cross-react with and inhibit human FVIII (positive control) and plasma from dogs without inhibitors (negative control) were assayed concurrently for comparison.

Results

Platelet-Targeted Lentiviral Vector Design and Strategy

A luciferase reporter assay revealed that fragments of the full-length human ITGA2B gene promoter permitted comparable platelet-specific gene transcription (FIG. 1A). Three different ITGA2B promoter fragments (−1218, −889 and −673) directed similar levels of luciferase activity within a pro-megakaryocytic cell line. In contrast, ITGA2B promoter driven luciferase activity remained undetectable in the other blood cell lineages and an epithelial cell line. Each ITGA2B promoter encodes Ets and GATA factors permitting a high level of megakaryocyte gene transcription and a repressor region that inhibits expression within other lineages (Prandini M H, et al., Blood 1996, 88(6): 2062-2070).20 As a result, two lentiviral gene transfer vectors were tested for optimal hematopoietic stem cell transduction efficiency and the ability to improve hemostatic function with platelet-derived BDDFVIII in hemophilia A dogs to develop a strategy for human gene therapy. Two dogs received an infusion of G-PBC transduced with a lentiviral vector encoding a fragment beginning at −889 nucleotide of the human ITGA2B promoter shown capable of directing megakaryocyte-specific transcription of BDDFVIII (FIG. 1B).21 Although FVIII is absent from platelets under normal conditions, this approach proved successful for storing viable BDDFVIII in platelet progeny derived from tissue cultured human CD34+G-PBC,12 and lentiviral vector-transduced bone marrow transplanted into hemophilia A mice (Shi et al., Journal of Thrombosis and Haemostasis 2007, 5(2): 352-361). One dog received an infusion of G-PBC transduced with a novel lentiviral vector encoding the shortest fragment of the ITGA2B promoter (−673) designed to induce megakaryocyte-specific expression of a hybrid molecule of BDDFVIII fused to the von Willebrand Factor (VWF) propeptide signal peptide and D2 domain (SPD2) to facilitate trafficking of BDDFVIII into the α-granule compartment (FIG. 1C) (Haberichter S L, et al., Arterioscler Thromb Vasc Biol 2002, 22(6): 921-926; Haberichter S L, et al., Blood 2003, 101(4): 1384-1391). VWF is a normal α-granule constituent in human platelets (albeit absent in canine platelets) (Nichols T C, et al., Blood 1993, 81(10): 2644-2651) that serves as a carrier protein of FVIII in human and canine plasma (Kaufman R J, et al. Molecular & Cellular Biology 1989, 9(3): 1233-1242).

Strategy for Hematopoietic Stem Cell Gene Therapy

To design a clinically relevant protocol, canine hematopoietic stem cells were mobilized from the bone marrow into the peripheral blood with canine cytokines (cG-CSF & cSCF) and G-PBC apheresis was performed without adverse incident identical to previous studies using GT dogs (Fang et al., supra). Mononuclear lymphocytes were isolated with Ficoll-Paque Plus from the apheresis product and then canine CD34 antigen positive (CD34+) cells were purified by immunomagnetic selection (McSweeney P A, et al., Blood 1998, 91(6): 1977-1986). Table 1 summarizes the conditions for autologous transplant of three hemophilia A dogs transfused with approximately $3\times10^6$ FVIII-transduced CD34+G-PBC/kg of body weight where each target cell was transduced with approximately $1\times10^4$ total viral particles/CD34+G-PBC without the use of ex vivo or in vivo selection for transduced cells (Columns 4,5). A non-myeloablative pre-transplant conditioning regimen was employed to create a niche in the bone marrow for the newly transplanted cells to engraft (Table 1, Column 2). The intensity of the conditioning regimen is determined by the level at which the dose becomes toxic to the organs. Earlier studies performed with normal canine models have demonstrated that stable allogeneic mixed donor/host hematopoietic chimerism can be safely established by the administration of a sublethal dose of busulfan (a drug preferentially toxic to hematopoietic stem cells) for pre-transplant conditioning. A recent report also demonstrated successful use of busulfan at 10 mg/kg for hematopoietic stem cell gene transfer to correct canine leukocyte adhesion deficiency (Bauer T R, Jr., et al., Nat Med 2008, 14(1): 93-97), followed by transient immunosuppression with mycophenolate mofetil (MMF) and cyclosporine (CSP) after major histocompatibility complex identical marrow transplantation (Enssle J, et al., Hum Gene Ther 2010, 21(4): 397-403). However, this level of pre-transplant conditioning regimen proved inappropriate for animals with hemophilia A, since the first dog (F20) transplanted in the current study required daily supplements with canine (c) FVIII in the form of canine plasma products and recombinant cFVIII for three months after G-PBC transplant. Epsilon-aminocaproic acid (EACA) was also infused after G-PBC transplant until human BDDFVIII reached a significant level in platelets. EACA is an effective synthetic inhibitor of the plasmin-plasminogen system and controls subarachnoid hemorrhage, genitourinary bleeding from many causes and dental surgery in hemophiliacs (Griffin J D, et al., Semin Thromb Hemost 1978, 5(1): 27-40). For comparison, the number of serious bleeding episodes that required treatment with cFVIII supplement has been recorded 1 year before and 2.5 years after G-PBC transplant for each dog (Table 1, Columns 10, 11) (Niemeyer G P, et al., Experimental Hematology 2003, 31(12): 1357-1362). As a result of the observation of frequent bleeding events with F20, a milder conditioning regimen consisting of a lower dose of busulfan was given to the next two transplant recipients (I42, 5 mg/kg; M64, 7 mg/kg). In conclusion, all three dogs received transient immune suppression (Fang et al., supra) and daily supplements of cFVIII and EACA for three months after G-PBC transplant as a standard transplant regimen until readily detectable human BDDFVIII levels were observed in platelets and hemocult tests indicated the absence of GI bleeding (Fang et al., supra). Ultimately, it was observed that I42 and M64 did not require further FVIII supplements as no severe bleeding episodes occurred for 2.5 years after transplant (Table 1, Column 11).

Biological Studies of Platelet FVIII

Figure 2:
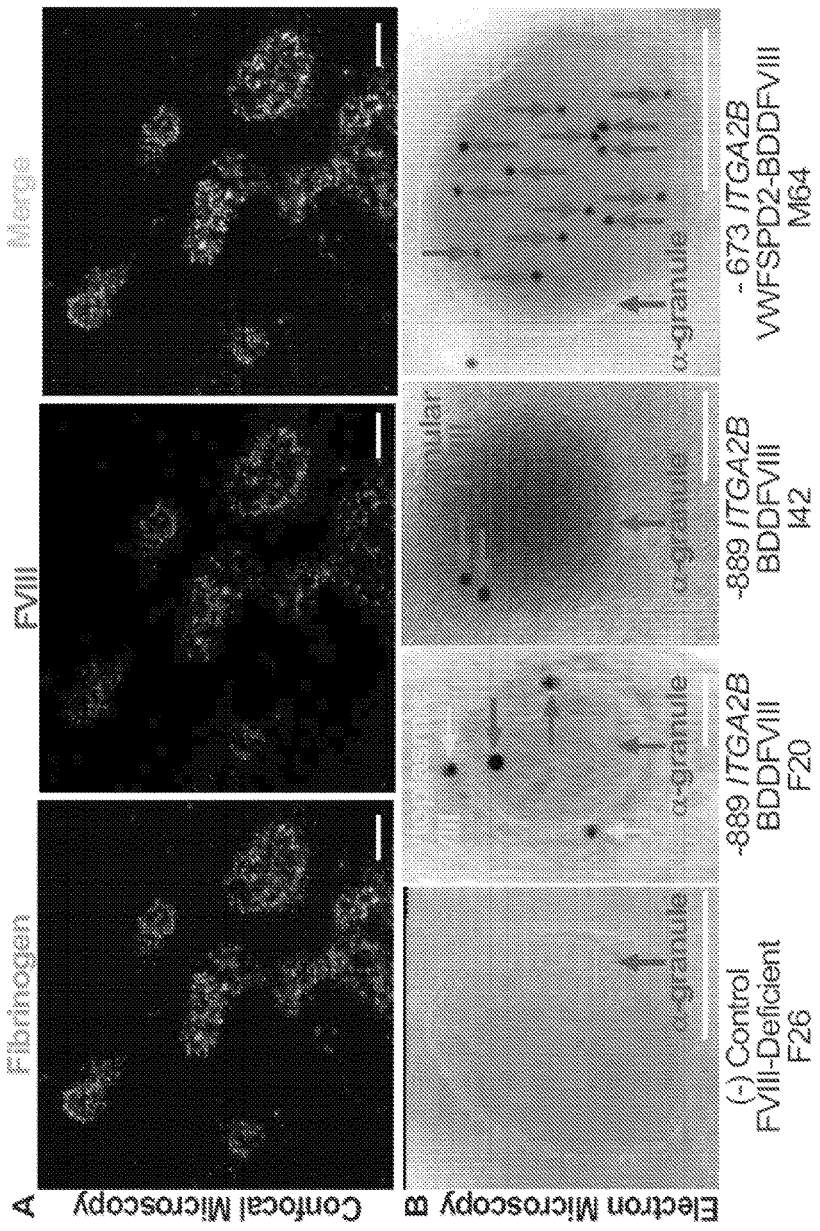
FIG. 2 shows synthesis and trafficking of BDDFVIII into canine platelet α-granules (A) confocal microscopy showing co-localization of BDDFVIII and Fg within platelets. (B) electron microscopy localized human BDDFVIII directly in α-granules.

Immuno-confocal microscopy was performed to determine if BDDFVIII was being synthesized and stored in platelets following G-PBC transplant. Shown in FIG. 2A are images of the results of microscopic analysis of platelets isolated from one dog (I42) that received an autologous transplant of lentiviral vector transduced G-PBC, which represents the outcome of analysis of all three dogs (F20, I42, M64). There was a punctate staining pattern for a specific marker of platelet α-granules, fibrinogen (Fg) (Left Panel). Human BDDFVIII was also detected in a punctate pattern within platelets (Middle Panel). Note that BDDFVIII staining co-localized frequently within Fg as evident by the appearance of a yellow staining when the left (Fg) and middle panel (BDDFVIII) were overlaid indicating that both proteins could be stored together within platelet α-granules (Right Panel) (Wilcox et al., *J Thromb Haemost* 2003, 1(12): 2477-2489).

Immuno-electron microscopy was performed to determine if exogenous BDDFVIII was being transported specifically to platelet α-granules. Immunogold analysis was performed on ultrathin sections of platelets with a 1° Ab to FVIII and a 2° Ab adsorbed on 10 nm gold particles (FIG. 2B). The α-granules appeared normal in size and shape within platelets of FVIII-Deficient dogs as well as FVIII transplant recipients. BDDFVIII is absent in platelet α-granules from a FVIII-Deficient negative control (Left Panel). In contrast, BDDFVIII was detected within α-granules and cytoplasm of platelets isolated from all three dogs (F20, I42, M64). This result is consistent with observations reported for ectopic expression of BDDFVIII within platelets of VWF (-/-) transgenic mice affected with von Willibrand disease (Yarovoi H, et al., *Blood* 2005, 105(12): 4674-4676). -673/ITGA2B-VWFSPD2-BDDFVIII transduced platelets from M64 stored the greatest level of BDDFVIII within the α-granule (Right Panel). In addition, BDDFVIII was detected rarely within membrane systems in the platelet cytoplasm indicating that the VWFSPD2 indeed had an increased efficiency to traffic BDDFVIII directly into the α-granule compartment.

Figure 3:
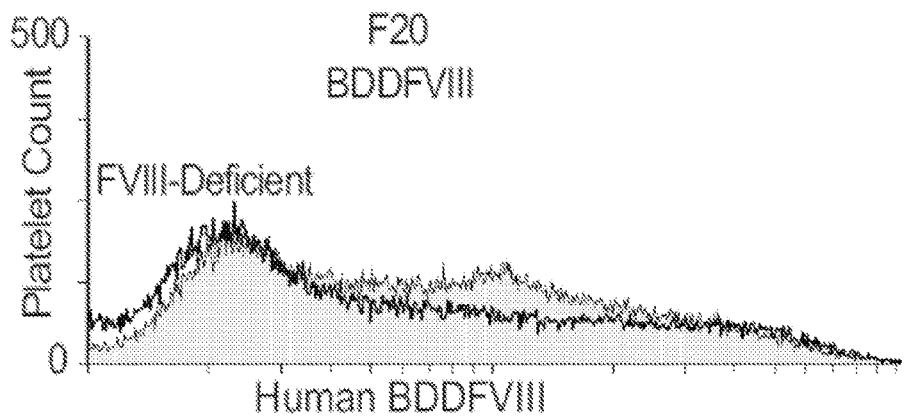
FIG. 3 shows quantitative analysis of platelet FVIII.
Figure 3:
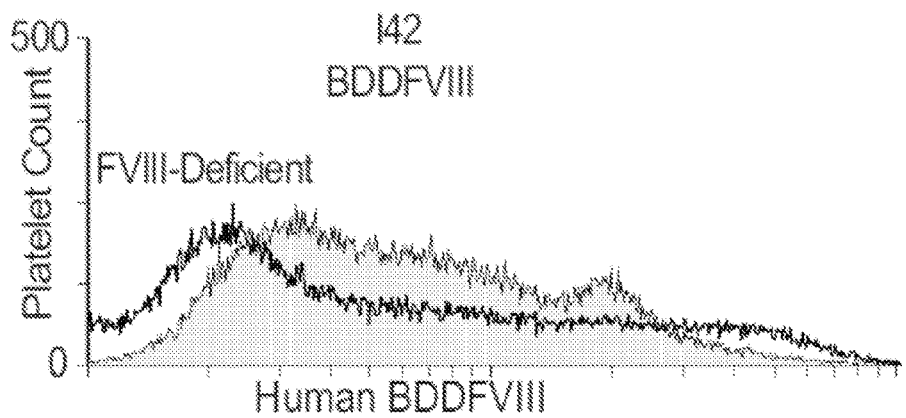
Figure 3:
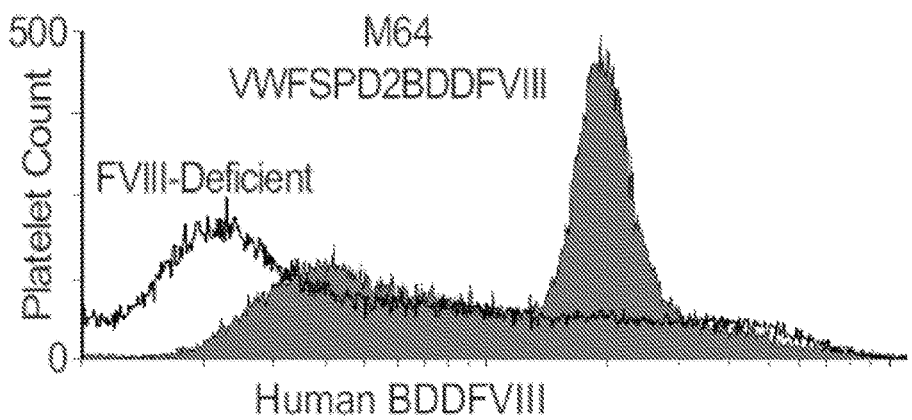

Immunofluorescent flow cytometric analysis of platelets confirmed that M64 stored the greatest level of FVIII per platelet because M64 platelets displayed the highest mean fluorescent intensity for detection of FVIII followed by I42 and F20 compared to FVIII-Deficient negative control platelets (FIG. 3). These results indicate that the VWFSPD2 targeting construct imparts an advantage for storing BDDFVIII within platelets. Subsequently, use of the smallest -673ITGA2B gene promoter allows the lentiviral vector to accommodate the largest therapeutic insert (in this case, the VWFSPD2-BDDFVIII); and therefore, may be more useful for gene transfer rather than the -1218 or -889 ITGA2B promoters.

Figure 4:
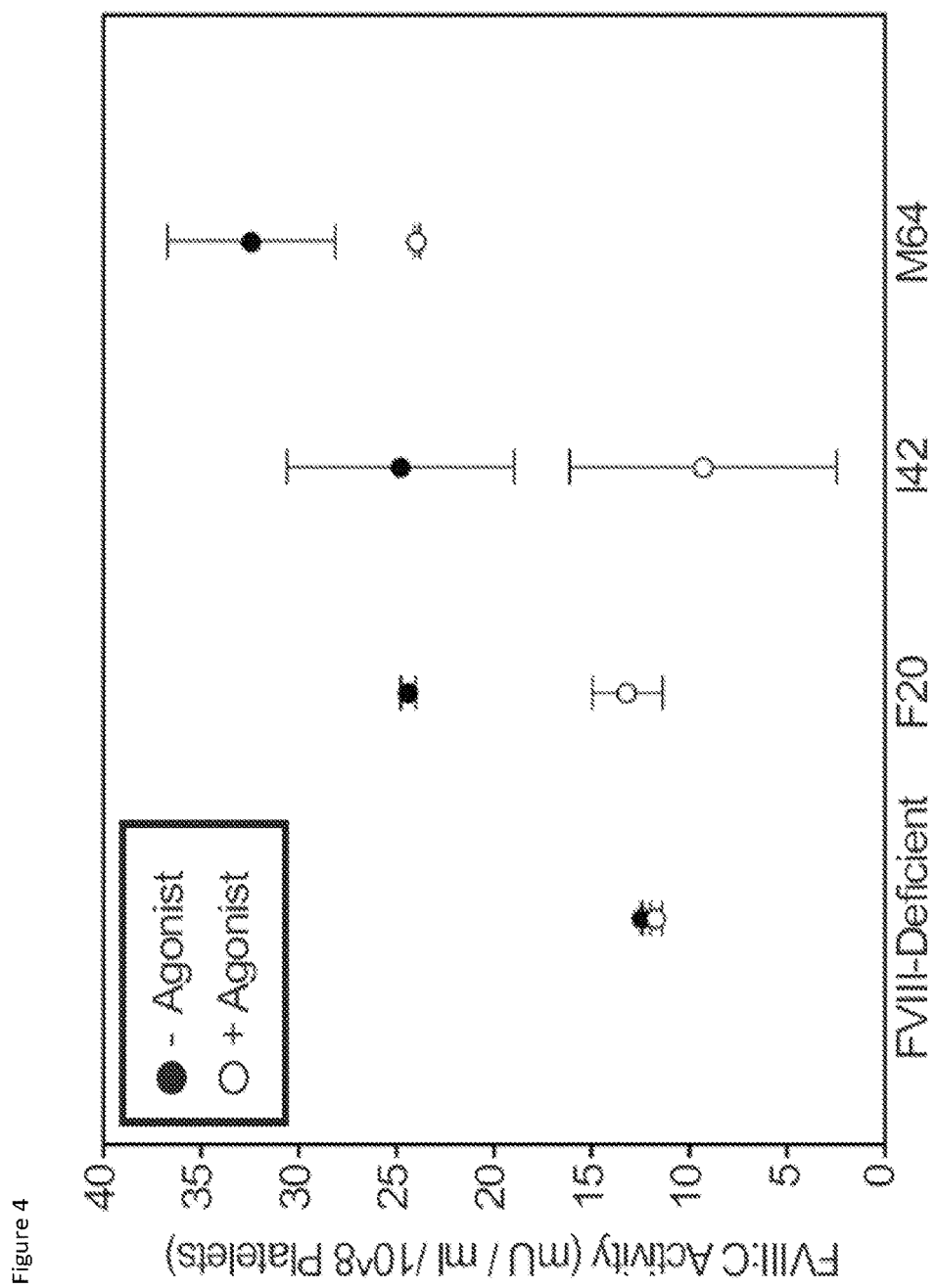
FIG. 4 shows activated platelets induced to secrete FVIII: C.

A Chromogenix Coatest® SP4 FVIII assay was perform to determine if activated platelets could secrete a biologically active form of BDDFVIII (FVIII:C) as previously shown for activated human megakaryocytes in tissue culture (Wilcox et al., *Thromb Haemost* 2003, 1(12): 2477-2489.12 In FIG. 4 platelet lysates from a FVIII-Deficient dog show that the level of BDDFVIII:C background activity is virtually unchanged for untreated (Black, -Agonist) and activated platelets (White, +Agonist). In contrast, FVIII:C activity was detected readily in the lysate of quiescent, untreated platelets from F20, I42 and M64. Furthermore, BDDFVIII:C levels were decreased in lysates of platelets stimulated by a mixture of physiological agonists of platelet activation: ADP, epinephrine, and canine PAR 1,3,4 in all three experimental dogs. In summary, dogs that received BDDFVIII-transduced G-PBC show an appreciable decrease in FVIII:C activity only after platelet activation indicating that platelets from experimental animals can be induced to secrete FVIII within the vasculature.

Genomic Analysis of the Lentiviral Vector

The lentiviral vector WPRE element was detected by PCR of genomic DNA isolated from leukocytes collected from F20, I42, and M64 for at least 2.5 years after transplant (FIG. 5A). Real time quantitative PCR (RT-qPCR) analysis of genomic DNA isolated from peripheral blood leukocytes revealed that the transduction efficiency for each lentiviral vector was 1% (F20), 4% (I42) and 2% (M64) (Table 1, Column 8). The detection of lentiviral vector by genomic analysis in the absence of the appearance of insertional oncogenesis is consistent with the overall good health of all of the dogs with frequent evaluation of peripheral blood counts and peripheral blood smears documenting normal morphology and numbers of circulating hematopoietic cells. Linear Amplification-Mediated (LAM)-PCR was also performed to determine the integration pattern of lentiviral vector within the genome of the experimental dogs. FIG. 5B shows that lentiviral vector was not present within the genome of a FVIII-Deficient control while multiple bands appear to be present in the genomic DNA of transplanted dogs (F20, I42 and M64). A distinct insertion site was detected specifically in chromosome 4 for F20 and chromosome 35 for M64. The results demonstrate that insertion of the lentiviral vector could be detected within I42 genomic DNA, although a site of insertion could not be localized to a precise region of the current canine genome map (Sutter N B, Ostrander E A. Dog star rising: the canine genetic system. *Nat Rev Genet* 2004, 5(12): 900-910). In summary, the results indicate that insertional mutagenesis had not occurred when this study was concluded (≈2.5 years after transplant). This is consistent with another report that found lentiviral vectors usually insert into benign areas of the genome in animals and humans (Biffi A, et al., *Blood* 2011, 117(20): 5332-5339).

Efficacy of Platelet-Targeted Gene Therapy for Hemophilia A

It was observed previously that human hematopoietic cells could serve as a primary tissue source for the synthesis of a functional form of human BDDFVIII (FVIII:C) within tissue-cultured human megakaryocytes (Shi Q, et al., *Molecular Genetics and Metabolism* 2003, 79(1): 25-33.), in peripheral blood platelets isolated from mice xeno-transplanted with BDDFVIII-transduced human G-PBC,12 and in a murine model for hemophilia A that received a transplant of BDDFVIII-transduced bone marrow (Shi Q, et al. *Journal of Thrombosis and Haemostasis* 2007, 5(2): 352-361). The current study (FIG. 6) shows that FVIII:C activity (≈5-15 mU/ml/108 platelets) can be detected by chromogenic analysis for at least 2.5 years after autologous G-PBC transplant in each dog with the highest levels appearing approximately one year after transplant and typically leveling off to ≈5-10 mU/ml/$10^8$ platelets (F20, I42, M6). Samples from FVIII-Deficient dogs served as negative controls for each time point (black line).

Figure 6:
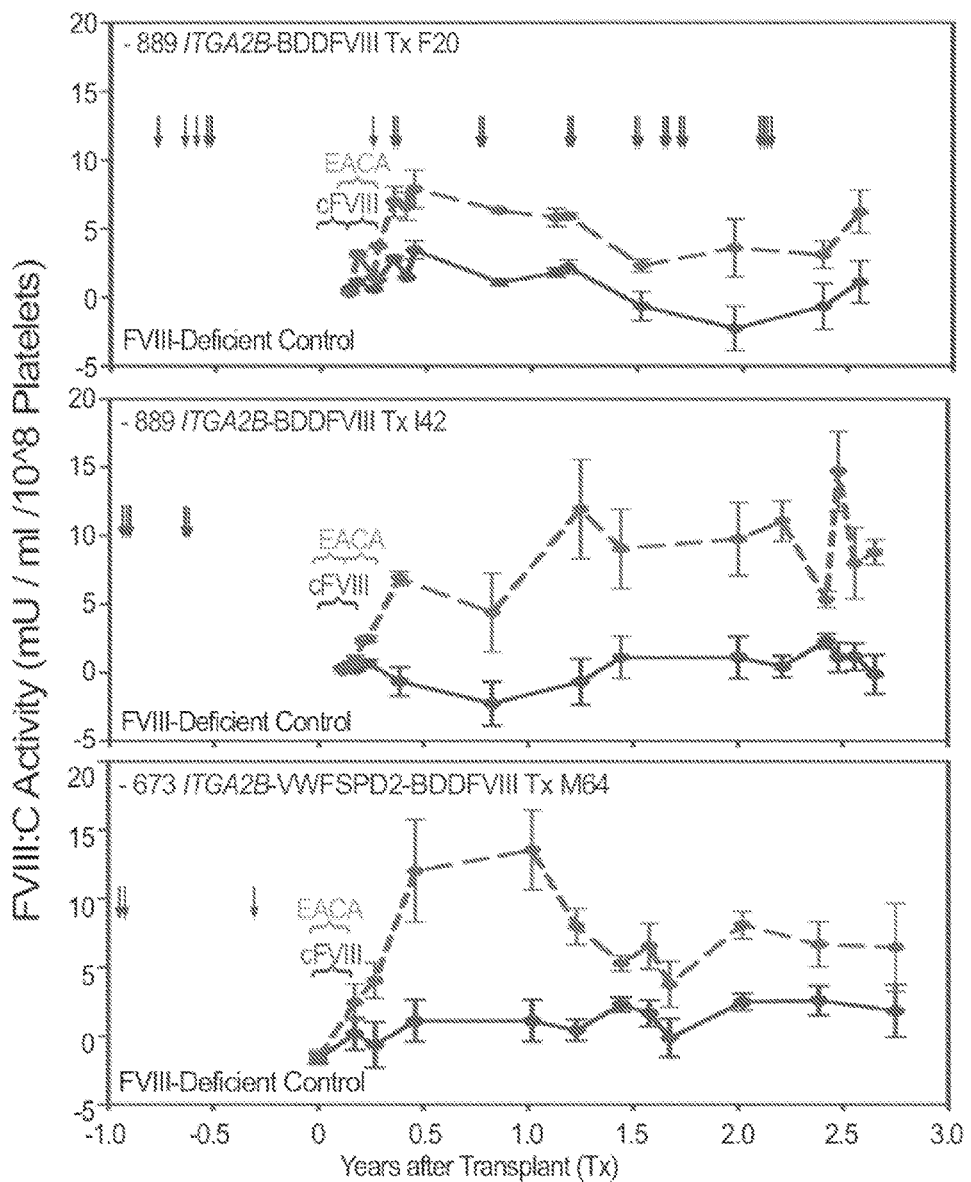
FIG. 6 shows correction of the canine Hemophilia A phenotype with platelet BDDFVIII.

To determine the total level FVIII:C activity present within each animal at any given time it is noted that there is ≈$2\times10^8$ platelets/1.0 ml blood and there is ≈92 ml blood/kg in dogs. Using values recorded in Table 1 for weight and transduction efficiency and the mean FVIII:C level of each dog calculated from data points shown in FIG. 6, it is estimated that there is approximately 0.230 U (F20), 1.325 U (I42) and 0.676 U (M64) FVIII:C/dog stored within all of the circulating platelets. To put these values in perspective, the term 1 U FVIII:C/ml defines 100% FVIII activity in the reference plasma from a normal (20 kg) dog; therefore, a normal (20 kg) animal has ≈800 total units of FVIII in its plasma volume at any given time. The results in FIG. 6 show that multiple severe bleeding episodes occurred in each animal one year prior to G-PBC that required a transfusion with cFVIII supplements. Note, to prevent bleeding due to the gene therapy protocol, each dog received daily supplements of cFVIII beginning on day one of the G-PBC transplant protocol. EACA was also administered to the transplanted dogs until blood was absent from their stool, which remarkably coincided with platelet FVIII:C levels reaching ≈5 mU/ml/$10^8$ platelets. F20 (Top Panel) displayed the lowest overall platelet FVIII:C levels of ≤5 mU/ml/$10^8$ platelets and also experienced severe intermittent bleeding episodes throughout the experimental follow-up of 2.5 years after transplant that required administration of additional supplements in the form of transfusions of normal canine plasma or cFVIII. This result indicates that 5 mU/ml/$10^8$ platelet FVIII:C appears to be a threshold level of transgene expression that must be overcome in canine hemophilia A to achieve adequate correction of the bleeding phenotype. Transplant dog I42 (Middle Panel) maintained the highest steady state of FVIII:C of approximately 9 mU/ml/$10^8$ platelets and did not experience severe bleeding requiring administration of cFVIII supplements ultimately demonstrating correction of the hemophilia A phenotype for at least 2.5 years after transplant. M64 (Bottom Panel) reached 5 mU FVIII:C/ml/$10^8$ platelets earlier than the other transplant dogs with the synthesis of a hybrid SPD2FVIII molecule that obtained a mean FVIII:C activity level of 8 mU/ml/$10^8$ platelets. This result demonstrates that the use of either the −889ITGA2B gene promoter or the −673ITGA2B gene promoter coupled with the VWFSPD2 trafficking peptide can be used effectively to target BDDFVIII to platelets leading to correction of the canine hemophilia A phenotype.

The time required for whole blood to clot in a test tube was measured for each dog using traditional version of the Lee-White whole blood clotting time (WBCT) assay (Nichols T C, et al., *J Thromb Haemost* 2012, 10(3): 474-476). Hemostatically normal dogs have a mean WBCT of 10.5 minutes±SD 1.4 minutes. The baseline WBCT for the FVIII-Deficient dogs was 44.5 (F20), 40.5 (I42) and >60 (M64) minutes before G-PBC transplant. After G-PBC transplant the average WBCT decreased to 39.5 (F20, n=5), 38.4 (I42, n=5) and 41.9 (M64, n=4) minutes. This result shows a very modest decrease in WBCT, which could be considered well within the normal variation of WBCT for FVIII-Deficient dogs. Interestingly, this result supports the inability to detect FVIII:C within the plasma of the experimental dogs (which is an essential component for success of the WBCT). Thus, this outcome indicates that measurement of WBCT ex vivo is not a suitable assay to predict the efficacy for platelet FVIII to improve hemostasis in vivo because (unlike plasma FVIII) the results indicate that platelet-derived FVIII must be secreted from activated platelets following stimulation with physiological platelet agonists at the site of vascular injury to improve hemostasis within FVIII-deficient dogs as shown in FIG. 4 and FIG. 6.

To determine if the G-PBC transplant recipients developed a humoral antibody response to the newly expressed human BDDFVIII, canine blood plasma from (F20, I42 and M64) was screened for inhibitors with an activated partial thromboplastin time (aPTT) mixing assay which detects inhibitory antibodies to either coagulation factor VIII or IX. Plasma from hemophilia A dogs with known Bethesda Inhibitor (BIU) titers that cross-react with and inhibit human FVIII was used as a positive control and plasma from dogs without inhibitors was assayed concurrently as a negative control for comparative analysis. The results indicate that F20, I42, and M64 did not develop inhibitors (Table 1: Column 12). This result is consistent with our inability to detect the presence of FVIII:C in the plasma. This outcome is identical with the failure of hemophilia A mice to develop inhibitory antibodies to the human platelet BDDFVIII and our the inability to detect FVIII:C in the plasma following transplant of lentiviral vector-transduced murine bone marrow (Shi Q, et al., Journal of Thrombosis and Haemostasis 2007, 5(2): 352-361). This further supports targeting transgene synthesis of BDDFVIII to platelets as a treatment for humans with pre-existing antibodies to FVIII (Shi Q, et al., J Clin Invest 2006, 116(7): 1974-1982; Kuether et al., *J Thromb Haemost* 2012).

TABLE 1

Conditions for Autologous Transplant of ITGA2B-BDDFVIII Transduced CD34+ G-PBC into FVIII-Deficient Dogs

| Dog | Pre-Tx Conditioning Busulfan (mg/kg) | Lentivirus Vector | Total Viral Particles (×$10^4$)/Cell | Tx CD34(+) PBC/kg Infused | Tx CD34(−) PBC/kg Infused | Weight (kg) |
|---|---|---|---|---|---|---|
| ♂ F20 | 10 | −889 ITGA2B-BDDFVIII | 0.8 | 4.0 × $10^6$ | 2.0 × $10^6$ | 25.20 |
| ♂ I42 | 5 | −889 ITGA2B-BDDFVIII | 1.3 | 1.25 × $10^6$ | 2.0 × $10^6$ | 20.00 |
| ♂ M64 | 7 | −673 ITGA2B-VWFSPD2-BDDFVIII | 0.7 | 4.58 × $10^6$ | 2.6 × $10^6$ | 22.90 |

| Dog | Post Tx Transduction Efficiency (%)* | Days Post Tx Immune Suppression | Pre Tx Serious Bleeding/yr | Post Tx Serious Bleeding/yr | Post Tx Inhibitor Detection | Tx Age Years | Follow-up Years |
|---|---|---|---|---|---|---|---|
| ♂ F20 | 1.00 | MMF31/CSP70 | 5.00 | 7.00 | 0/2 | 6.5 | 2.6 |
| ♂ I42 | 4.00 | MMF45/CSP91 | 5.00 | 0.00 | 0/2 | 4.25 | 2.75 |
| ♂ M64 | 2.00 | MMF91/CSP91 | 3.00 | 0.00 | 0/2 | 1.25 | 2.75 |

*Percent (%) peripheral blood cells positive for lentiviral vector by RT-PCR
*Mycophenolete Mofetil is MMF
*Cyclosporine is CSP All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

SEQUENCE LISTING

<160> NUMBER OF SEQ ID NOS: 35

<210> SEQ ID NO 1
<211> LENGTH: 37
<212> TYPE: DNA
<213> ORGANISM: Artificial Sequence
<220> FEATURE:
<223> OTHER INFORMATION: Synthetic

<400> SEQUENCE: 1
ttacgcgtcg acagatctaa atgtggctgg ttacccc                37

<210> SEQ ID NO 2
<211> LENGTH: 35
<212> TYPE: DNA
<213> ORGANISM: Artificial Sequence
<220> FEATURE:
<223> OTHER INFORMATION: Synthetic

<400> SEQUENCE: 2
ttacgcgtcg acagatctgt gctcaatgct gtgcc                  35

<210> SEQ ID NO 3
<211> LENGTH: 34
<212> TYPE: DNA
<213> ORGANISM: Artificial Sequence
<220> FEATURE:
<223> OTHER INFORMATION: Synthetic

<400> SEQUENCE: 3
ttacgcgtcg acagatctcc ttgccaccta gacc                   34

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4
ggcgtcttcc atggtccttc ttccacaacc                        30

<210> SEQ ID NO 5
<211> LENGTH: 28
<212> TYPE: DNA
<213> ORGANISM: Artificial Sequence
<220> FEATURE:
<223> OTHER INFORMATION: Synthetic

<400> SEQUENCE: 5
gttaatcgat atctccttgc cacctaga                          28

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
aatctggcag gaatcatggt ccttcttcca caacct                 36

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
aggttgtgga agaaggacca tgattcctgc cagatttgc          39

<210> SEQ ID NO 8
<211> LENGTH: 30
<212> TYPE: DNA
<213> ORGANISM: Artificial Sequence
<220> FEATURE:
<223> OTHER INFORMATION: Synthetic

<400> SEQUENCE: 8
cgtctcggcc cttttgctgc catgagacag          30

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
atcgatatct ccttgccacc ta          22

<210> SEQ ID NO 10
<211> LENGTH: 29
<212> TYPE: DNA
<213> ORGANISM: Artificial Sequence
<220> FEATURE:
<223> OTHER INFORMATION: Synthetic

<400> SEQUENCE: 10
cgtctcaggg ccaccagaag atactacct          29

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
acgcgtcttc tctacatact agta          24

<210> SEQ ID NO 12
<211> LENGTH: 19
<212> TYPE: DNA
<213> ORGANISM: Artificial Sequence
<220> FEATURE:
<223> OTHER INFORMATION: Synthetic

<400> SEQUENCE: 12
aacaccacgg aattgtcag          19

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
tggatacgct gctttaatgc          20

```
<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
aattgtcagt gcccaacag                                                    19

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
agcttgcctt gagtgcttca                                                   20

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
tgactaaaag ggtctgaggg a                                                 21

<210> SEQ ID NO 17
<211> LENGTH: 23
<212> TYPE: DNA
<213> ORGANISM: Artificial Sequence
<220> FEATURE:
<223> OTHER INFORMATION: Synthetic

<400> SEQUENCE: 17
tgcccgtctg ttgtgtgact ctg                                               23

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
atgcatccca cttgctggta t                                                 21

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
tgcccatcgt taggttgg                                                     18

<210> SEQ ID NO 20
<211> LENGTH: 22
<212> TYPE: DNA
<213> ORGANISM: Artificial Sequence
<220> FEATURE:
<223> OTHER INFORMATION: Synthetic
```

<400> SEQUENCE: 20

| tgcctgccag ccttccatcc ag | | | | | 22 |
|---|---|---|---|---|---|

<210> SEQ ID NO 21
<211> LENGTH: 1274
<212> TYPE: DNA
<213> ORGANISM: Artificial Sequence
<220> FEATURE:
<223> OTHER INFORMATION: Synthetic

<400> SEQUENCE: 21

| ttacgcgtcg acagatctaa atgtggctat ggttacccct agcggacctc ttaaatcttc | 60 |
|---|---|
| ctgagaacct gctttttgg gaaggcatga gtgccagtaa gacttggcac tcctcctctt | 120 |
| ccgcttaccg agagaaaatg actttgcctt tctgctcaaa actcatccct tcactttgtc | 180 |
| accctatgtt tgcatcttcc atccttagtg tgtgtttcca tccatccagt ctttcagcaa | 240 |
| tacacgtact acacattgga ctcttgggta gtctctaggg ctgtagcaag gagccttgct | 300 |
| cccaagggac tcatttacac aatcctgtga acggaccaag agtaaacagt gtgctcaatg | 360 |
| ctgtgcctac gtgtgttagc ccacgcggcc agcctgagga gtcagggaag gctcccctag | 420 |
| gcaaagcccc caaccagaat caagtcttaa tggttaaaga gctccatcac ccaaaaagga | 480 |
| ttgagggcct accttcaact gaacagctaa tgcataatct cagaaactgt gagtcaaaat | 540 |
| tccctggaat aactccactt tatccccaat ctccttgcca cctagaccaa ggtccattca | 600 |
| ccaccctgtc cccagcactg actgcactgc tgtggccaca ctaaagcttg gctcaagacg | 660 |
| gaggaggagt gaggaagctg ctgcaccaat atggctggtt gaggccgccc aaggtcctag | 720 |
| aaggaggaag tgggtaaatg ccatatccaa aaagatacag aagcctcagg ttttatcggg | 780 |
| ggcagcagct tccttctcct tccccgacct gtggccaagt cacaaagcac acagctgta | 840 |
| cagccagatg ggggaaggga ggagattaga actgtaggct agagtagaca agtatggacc | 900 |
| agttcacaat cacgctatcc caagcagaaa gtgatggtgg cttggactag cacggtggta | 960 |
| gtagagatgg ggtaaagatt caagagacat cattgatagg cagaaccaat aggacatggt | 1020 |
| aataaactat tctcaggaaa ggggaggagt catggctttc agccatgagc atccaccctc | 1080 |
| tgggtggcct cacccacttc ctggcaattc tagccaccat gagtccaggg gctatagccc | 1140 |
| tttgctctgc ccgttgctca gcaagttact tggggttcca gtttgataag aaaagacttc | 1200 |
| ctgtggagga atctgaaggg aaggaggagg agctggccca ttcctgcctg ggaggttgtg | 1260 |
| gaagaaggac catg | 1274 |

<210> SEQ ID NO 22
<211> LENGTH: 942
<212> TYPE: DNA
<213> ORGANISM: Artificial Sequence
<220> FEATURE:
<223> OTHER INFORMATION: Synthetic

<400> SEQUENCE: 22

| ttacgcgtcg acagatctgt gctcaatgct gtgcctacgt gtgttagccc acgcggccag | 60 |
|---|---|
| cctgaggagt cagggaaggc tcccctaggc aaagccccca accagaatca agtcttaatg | 120 |
| gttaaagagc tccatcaccc aaaaaggatt gagggcctac cttcaactga acagctaatg | 180 |
| cataatctca gaaactgtga gtcaaaattc cctggaataa ctcacttta tccccaatct | 240 |
| ccttgccacc tagaccaagg tccattcacc ccctgtccc cagcactgac tgcactgctg | 300 |

| | |
|---|---|
| tggccacact aaagcttggc tcaagacgga ggaggagtga ggaagctgct gcaccaatat | 360 |
| ggctggttga ggccgcccaa ggtcctagaa ggaggaagtg ggtaaatgcc atatccaaaa | 420 |
| agatacagaa gcctcaggtt ttatcggggg cagcagcttc cttctccttc cccgacctgt | 480 |
| ggccaagtca caaagcacca cagctgtaca gccagatggg ggaagggagg agattagaac | 540 |
| tgtaggctag agtagacaag tatggaccag ttcacaatca cgctatccca agcagaaagt | 600 |
| gatggtggct tggactagca cggtggtagt agagatgggg taaagattca agagacatca | 660 |
| ttgataggca gaaccaatag gacatggtaa taaactattc tcaggaaagg ggaggagtca | 720 |
| tggctttcag ccatgagcat ccaccctctg gtggcctca cccacttcct ggcaattcta | 780 |
| gccaccatga gtccagggc tatagccctt tgctctgccc gttgctcagc aagttacttg | 840 |
| gggttccagt ttgataagaa aagacttcct gtggaggaat ctgaagggaa ggaggaggag | 900 |
| ctggcccatt cctgcctggg aggttgtgga agaaggacca tg | 942 |

<210> SEQ ID NO 23
<211> LENGTH: 720
<212> TYPE: DNA
<213> ORGANISM: Artificial Sequence
<220> FEATURE:
<223> OTHER INFORMATION: Synthetic

<400> SEQUENCE: 23

| | |
|---|---|
| ttacgcgtcg acagatctcc ttgccaccta gaccaaggtc cattcaccac cctgtcccca | 60 |
| gcactgactg cactgctgtg gccacactaa agcttggctc aagacggagg aggagtgagg | 120 |
| aagctgctgc accaatatgg ctggttgagg ccgcccaagg tcctagaagg aggaagtggg | 180 |
| taaatgccat atccaaaaag atacagaagc tcaggttttt atcggggca gcagcttcct | 240 |
| tctccttccc cgacctgtgg ccaagtcaca agcaccaca gctgtacagc cagatggggg | 300 |
| aagggaggag attagaactg taggctagag tagacaagta tggaccagtt cacaatcacg | 360 |
| ctatcccaag cagaaagtga tggtggcttg gactagcacg gtggtagtag agatggggta | 420 |
| aagattcaag agacatcatt gataggcaga accaatagga catggtaata aactattctc | 480 |
| aggaaagggg aggagtcatg gctttcagcc atgagcatcc accctctggg tggcctcacc | 540 |
| cacttcctgg caattctagc caccatgagt ccaggggcta tagccctttg ctctgcccgt | 600 |
| tgctcagcaa gttactgggg gttccagttt gataagaaaa gacttcctgt ggaggaatct | 660 |
| gaagggaagg aggaggagct ggcccattcc tgcctgggag gttgtggaag aaggaccatg | 720 |

<210> SEQ ID NO 24
<211> LENGTH: 1920
<212> TYPE: DNA
<213> ORGANISM: Artificial Sequence
<220> FEATURE:
<223> OTHER INFORMATION: Synthetic

<400> SEQUENCE: 24

| | |
|---|---|
| atcgatatct ccttgccacc tagaccaagg tccattcacc ccctgtccc cagcactgac | 60 |
| tgcactgctg tggccacact aaagcttggc tcaagacgga ggaggagtga ggaagctgct | 120 |
| gcaccaatat ggctggttga ggccgcccaa ggtcctagaa ggaggaagtg ggtaaatgcc | 180 |
| atatccaaaa agatacagaa gcctcaggtt ttatcggggg cagcagcttc cttctccttc | 240 |
| cccgacctgt ggccaagtca caaagcacca cagctgtaca gccagatggg ggaagggagg | 300 |
| agattagaac tgtaggctag agtagacaag tatggaccag ttcacaatca cgctatccca | 360 |
| agcagaaagt gatggtggct tggactagca cggtggtagt agagatgggg taaagattca | 420 |

| | |
|---|---|
| agagacatca ttgataggca gaaccaatag gacatggtaa taaactattc tcaggaaagg | 480 |
| ggaggagtca tggctttcag ccatgagcat ccaccctctg ggtggcctca cccacttcct | 540 |
| ggcaattcta gccaccatga gtccaggggc tatagccctt tgctctgccc gttgctcagc | 600 |
| aagttacttg gggttccagt ttgataagaa aagacttcct gtggaggaat ctgaagggaa | 660 |
| ggaggaggag ctggcccatt cctgcctggg aggttgtgga agaaggacca tgattcctgc | 720 |
| cagatttgcc ggggtgctgc ttgctctggc cctcattttg ccaggaccc tttgcgagtg | 780 |
| ccttgtcaca ggtcaatcac acttcaagag ctttgacaac agatacttca ccttcagtgg | 840 |
| gatctgccta tacctgctgg cccgggattg ccaggaccac tccttctcca ttgtcattga | 900 |
| gactgtccag tgtgctgatg accgcgacgc tgtgtgcacc cgctccgtca ccgtccggct | 960 |
| gcctggcctg cacaacagcc ttgtgaaact gaagcatggg gcaggagttg ccatggatgg | 1020 |
| ccaggacgtc cagctccccc tcctgaaagg tgacctccgc atccagcata cagtgacggc | 1080 |
| ctccgtgcgc ctcagctacg ggaggacctg cagatggac tgggatggcc gcggggggct | 1140 |
| gctggtgaag ctgtccccg tctatgccgg gaagacctgc ggcctgtgtg ggaattacaa | 1200 |
| tggcaaccag ggcgacgact ccttacccc ctctgggctg gcggagcccc gggtggagga | 1260 |
| cttcgggaac gcctggaagc tgcacgggga ctgccaggac ctgcagaagc agcacagcga | 1320 |
| tccctgcgcc ctcaacccgc gcatgaccag gttctccgag gaggcgtgcg cggtcctgac | 1380 |
| gtccccaca ttcgaggcct gccatcgtgc cgtcagcccg ctgcctacc tgcggaactg | 1440 |
| ccgctacgac gtgtgctcct gctcggacgg ccgcgagtgc ctgtgcggcg ccctggccag | 1500 |
| ctatgccgcg gcctgcgcgg ggagaggcgt gcgcgtcgcg tggcgcgagc caggccgctg | 1560 |
| tgagctgaac tgcccgaaaag gccaggtgta cctgcagtgc gggaccccct gcaacctgac | 1620 |
| ctgccgctct ctctcttacc cggatgagga atgcaatgag gcctgcctgg agggctgctt | 1680 |
| ctgcccccca gggctctaca tggatgagag ggggactgc gtgcccaagg cccagtgccc | 1740 |
| ctgttactat gacggtgaga tcttccagcc agaagacatc ttctcagacc atcacaccat | 1800 |
| gtgctactgt gaggatggct tcatgcactg taccatgagt ggagtccccg gaagcttgct | 1860 |
| gcctgacgct gtcctcagca gtcccctgtc tcatggcagc aaaagggcca ccagaagata | 1920 |

<210> SEQ ID NO 25
<211> LENGTH: 15052
<212> TYPE: DNA
<213> ORGANISM: Artificial Sequence
<220> FEATURE:
<223> OTHER INFORMATION: Synthetic

<400> SEQUENCE: 25

| | |
|---|---|
| ttggaagggc taattcactc ccaaagaaga caagatatcc ttgatctgtg gatctaccac | 60 |
| acacaaggct acttccctga ttagcagaac tacacaccag gccaggggt cagatatcca | 120 |
| ctgacctttg gatggtgcta caagctagta ccagttgagc cagataaggt agaagaggcc | 180 |
| aataaaggag agaacaccag cttgttacac cctgtgagcc tgcatgggat ggatgacccg | 240 |
| gagagagaag tgttagagtg gaggtttgac agccgcctag catttcatca cgtggcccga | 300 |
| gagctgcatc cggagtactt caagaactgc tgatatcgag cttgctacaa gggactttcc | 360 |
| gctggggact ttccaggag gcgtggcctg ggcgggactg ggagtggcg agccctcaga | 420 |
| tcctgcatat aagcagctgc tttttgcctg tactgggtct ctctggttag accagatctg | 480 |
| agcctgggag ctctctggct aactagggaa cccactgctt aagcctcaat aaagcttgcc | 540 |

```
ttgagtgctt caagtagtgt gtgcccgtct gttgtgtgac tctggtaact agagatccct    600
cagacccttt tagtcagtgt ggaaaatctc tagcagtggc gcccgaacag ggacttgaaa    660
gcgaaaggga accagagga gctctctcga cgcaggactc ggcttgctga agcgcgcacg    720
gcaagaggcg aggggcggcg actggtgagt acgccaaaaa ttttgactag cggaggctag    780
aaggagagag atgggtgcga gagcgtcagt attaagcggg ggagaattag atcgcgatgg    840
gaaaaaattc ggttaaggcc agggggaaag aaaaaatata aattaaaaca tatagtatgg    900
gcaagcaggg agctagaacg attcgcagtt aatcctggcc tgttagaaac atcagaaggc    960
tgtagacaaa tactgggaca gctacaacca tcccttcaga caggatcaga agaacttaga   1020
tcattatata atacagtagc aaccctctat tgtgtgcatc aaaggataga gataaaagac   1080
accaaggaag ctttagacaa gatagaggaa gagcaaaaca aaagtaagac caccgcacag   1140
caagcggccg gccgctgatc ttcagacctg gaggaggaga tatgagggac aattggagaa   1200
gtgaattata taaatataaa gtagtaaaaa ttgaaccatt aggagtagca cccaccaagg   1260
caaagagaag agtggtgcag agagaaaaaa gagcagtggg aataggagct ttgttccttg   1320
ggttcttggg agcagcagga agcactatgg gcgcagcgtc aatgacgctg acggtacagg   1380
ccagacaatt attgtctggt atagtgcagc agcagaacaa tttgctgagg ctattgagg   1440 cgcaacagca tctgttgcaa ctcacagtct ggggcatcaa gcagctccag gcaagaatcc   1500
tggctgtgga aagatacctaa aggatcaac agctcctggg gatttggggt tgctctggaa   1560
aactcatttg caccactgct gtgccttgga atgctagttg gagtaataaa tctctggaac   1620
agatttggaa tcacacgacc tggatggagt gggacagaga aattaacaat tacacaagct   1680
taatacactc cttaattgaa gaatcgcaaa accagcaaga aaagaatgaa caagaattat   1740
tggaattaga taaatgggca gtttgtgga attggtttaa cataacaaat tggctgtggt   1800
atataaaatt attcataatg atagtaggag gcttggtagg tttaagaata gttttttgctg   1860 tactttctat agtgaataga gttaggcagg gatattcacc attatcgttt cagacccacc   1920
tcccaacccc gaggggaccc gacaggcccg aaggaataga agaagaaggt ggagagagag   1980
acagagacag atccattcga ttagtgaacg gatctcgacg gtatcggtta acttttaaaa   2040
gaaaaggggg gattgggggg tacagtgcag gggaaagaat agtagacata atagcaacag   2100
acatacaaac taaagaatta caaaaacaaa ttacaaaaat tcaaaatttt atcgatcacg   2160
agactagcct cgagaagctt gatcgatggc tccggtgccc gtcagtgggc agagcgcaca   2220
tcgcccacag tccccgagaa gttgggggga gggtcggca attgaaccgg tgcctagaga   2280
aggtggcgcg gggtaaactg ggaaagtgat gtcgtgtact ggctccgcct tttccgag    2340 ggtggggag aaccgtatat aagtgcagta gtcgccgtga acgttctttt tcgcaacggg    2400
tttgccgcca gaacacaggt gtcgtgacgc ggatccaggc ctaagcttac gatatctcct   2460
tgccacctag accaaggtcc attcaccacc ctgtccccag cactgactgc actgctgtgg   2520
ccacactaaa gcttggctca agacggagga ggagtgagga agctgctgca ccaatatggc   2580
tggttgaggc cgcccaaggt cctagaagga ggaagtgggt aaatgccata tccaaaaaga   2640
tacagaagcc tcaggtttta tcggggcag cagcttcctt ctccttcccc gacctgtggc    2700
caagtcacaa agcaccacag ctgtacagcc agatggggga aggaggaga ttagaactgt    2760 aggctagagt agacaagtat ggaccagttc acaatcacgc tatcccaagc agaaagtgat   2820
ggtggcttgg actagcacgg tggtagtaga gatggggtaa agattcaaga gacatcattg   2880
ataggcagaa ccaataggac atggtaataa actattctca ggaaagggga ggagtcatgg   2940
```

```
ctttcagcca tgagcatcca ccctctgggt ggcctcaccc acttcctggc aattctagcc   3000
accatgagtc cagggctat agccctttgc tctgcccgtt gctcagcaag ttacttgggg    3060
ttccagtttg ataagaaaag acttcctgtg gaggaatctg aagggaagga ggaggagctg   3120
gcccattcct gcctgggagg ttgtggaaga aggaccatga ttcctgccag atttgccggg   3180
gtgctgcttg ctctggccct cattttgcca ggacccttt gcgagtgcct tgtcacaggt    3240
caatcacact tcaagagctt tgacaacaga tacttcacct tcagtgggat ctgccagtac   3300
ctgctggccc gggattgcca ggaccactcc ttctccattg tcattgagac tgtccagtgt   3360
gctgatgacc gcgacgctgt gtgcacccgc tccgtcaccg tccggctgcc tggcctgcac   3420
aacagccttg tgaaactgaa gcatggggca ggagttgcca tggatggcca ggacgtccag   3480 ctcccctcc tgaaaggtga cctccgcatc cagcgtacag tgacggcctc cgtgcgcctc    3540
agctacgggg aggacctgca gatggactgg gatggccgcg ggaggctgct ggtgaagctg   3600
tcccccgtct atgccgggaa gacctgcggc ctgtgtggga attacaatgg caaccagggc   3660
gacgacttcc ttacccctc tgggctggcg gagccccggg tggaggactt cgggaacgcc    3720
tggaagctgc acgggactg ccaggacctg cagaagcagc acagcgatcc ctgcgccctc    3780
aacccgcgca tgaccaggtt ctccgaggag gcgtgcgcgg tcctgacgtc ccccacattc   3840
gaggcctgcc atcgtgccgt cagcccgctg ccctacctgc ggaactgccg ctacgacgtg   3900
tgctcctgct cggacggccg cgagtgcctg tgcggcgccc tggccagcta tgccgcggcc   3960
tgcgcgggga gcgcgtgcg cgtcgcgtgg cgcgagccag gccgctgtga gctgaactgc   4020
ccgaaaggcc aggtgtacct gcagtgcggg acccctgca acctgacctg ccgctctctc    4080
tcttacccgg atgaggaatg caatgaggcc tgcctggagg ctgcttctg ccccccaggg    4140 ctctacatgg atgagagggg ggactgcgtg cccaaggccc agtgccctg ttactatgac    4200 ggtgagatct tccagccaga agacatcttc tcagaccatc acaccatgtg ctactgtgag   4260
gatggcttca tgcactgtac catgagtgga gtccccggaa gcttgctgcc tgacgctgtc   4320
ctcagcagtc ccctgtctca tggcagcaaa agggccacca aagatacta cctgggtgca    4380 gtggaactgt catgggacta tatgcaaagt gatctcggtg agctgcctgt ggacgcaaga   4440
tttcctccta gagtgccaaa atcttttcca ttcaacacct cagtcgtgta caaaaagact   4500
ctgtttgtag aattcacgga tcacctttc aacatcgcta agccaaggcc acctggatg     4560 ggtctgctag gtcctaccat ccaggctgag gtttatgata cagtggtcat tacacttaag   4620
aacatggctt cccatcctgt cagtcttcat gctgttggtg tatcctactg gaaagcttct   4680
gagggagctg aatatgatga tcagaccagt caagggagag aagaagatga taaagtcttc   4740
cctggtggaa gccatacata tgtctggcag gtcctgaaag agaatggtcc aatggcctct   4800
gacccactgt gccttaccta ctcatatctt tctcatgtgg acctggtaaa agacttgaat   4860
tcaggcctca ttggagccct actagtatgt agagaaggga gtctggccaa ggaaaagaca   4920
cagaccttgc acaaatttat actacttttt gctgtatttg atgaagggaa aagttggcac   4980
tcagaaacaa agaactcctt gatgcaggat agggatgctg catctgctcg ggcctggcct   5040
aaaatgcaca cagtcaatgg ttatgtaaac aggtctctgc caggtctgat ggatgccac    5100 aggaaatcag tctattggca tgtgattgga atgggcacca ctcctgaagt gcactcaata   5160
ttcctcgaag gtcacacatt tcttgtgagg aaccatcgcc aggcgtcctt ggaaatctcg   5220
ccaataactt tccttactgc tcaaacactc ttgatggacc ttggacagtt tctactgttt   5280
```

```
tgtcatatct cttcccacca acatgatggc atggaagctt atgtcaaagt agacagctgt    5340
ccagaggaac cccaactacg aatgaaaaat aatgaagaag cggaagacta tgatgatgat    5400
cttactgatt ctgaaatgga tgtggtcagg tttgatgatg acaactctcc ttcctttatc    5460
caaattcgct cagttgccaa gaagcatcct aaaacttggg tacattacat tgctgctgaa    5520
gaggaggact gggactatgc tcccttagtc ctcgcccccg atgacagaag ttataaaagt    5580
caatatttga acaatggccc tcagcggatt ggtaggaagt acaaaaaagt ccgatttatg    5640
gcatacacag atgaaacctt taagactcgt gaagctattc agcatgaatc aggaatcttg    5700
ggacctttac tttatgggga agttggagac acactgttga ttatatttaa gaatcaagca    5760
agcagaccat ataacatcta ccctcacgga atcactgatg tccgtccttt gtattcaagg    5820
agattaccaa aaggtgtaaa acatttgaag gattttccaa ttctgccagg agaaatattc    5880
aaatataaat ggacagtgac tgtagaagat gggccaacta atcagatccc tcggtgcctg    5940
acccgctatt actctagttt cgttaatatg gagagagatc tagcttcagg actcattggc    6000
cctctcctca tctgctacaa agaatctgta gatcaaagag gaaaccagat aatgtcagac    6060
aagaggaatg tcatcctgtt ttctgtattt gatgagaacc gaagctggta cctcacagag    6120
aatatacaac gctttctccc caatccagct ggagtgcagc ttgaggatcc agagttccaa    6180
gcctccaaca tcatgcacag catcaatggc tatgtttttg atagtttgca gttgtcagtt    6240
tgtttgcatg aggtggcata ctggtacatt ctaagcattg gagcacagac tgacttcctt    6300
tctgtcttct tctctggata taccttcaaa cacaaaatgg tctatgaaga cacactcacc    6360
ctattcccat tctcaggaga aactgtcttc atgtcgatgg aaaacccagg tctatggatt    6420
ctggggtgcc acaactcaga ctttcggaac agaggcatga ccgccttact gaaggtttct    6480
agttgtgaca gaacactggt gattattac gaggacagtt atgaagatat ttcagcatac    6540
ttgctgagta aaaacaatgc cattgaacca agagaaataa ctcgtactac tcttcagtca    6600
gatcaagagg aaattgacta tgatgatacc atatcagttg aaatgaagaa ggaagatttt    6660
gacatttatg atgaggatga aaatcagagc ccccgcagct ttcaaaagaa aacacgacac    6720
tattttattg ctgcagtgga gaggctctgg gattatggga tgagtagctc cccacatgtt    6780
ctaagaaaca gggctcagag tggcagtgtc cctcagttca agaaagttgt tttccaggaa    6840
tttactgatg gctcctttac tcagcccttt accgtggag aactaaatga acatttggga    6900
ctcctggggc catatataag agcagaagtt gaagataata tcatggtaac tttcagaaat    6960
caggcctctc gtccctattc cttctattct agccttattt cttatgagga agatcagagg    7020
caaggagcag aacctagaaa aaactttgtc aagcctaatg aaaccaaaac ttacttttgg    7080
aaagtgcaac atcatatggc acccactaaa gatgagtttg actgcaaagc ctgggcttat    7140
ttctctgatg ttgacctgga aaaagatgtg cactcaggcc tgattggacc ccttctggtc    7200
tgccacacta acacactgaa ccctgctcat gggagacaag tgacagtaca ggaatttgct    7260 ctgttttca ccatctttga tgagaccaaa agctggtact tcactgaaaa tatggaaaga    7320
aactgcaggg ctccctgcaa tatccagatg gaagatccca cttttaaaga aattatcgc    7380 ttccatgcaa tcaatggcta cataatggat acactacctg gcttagtaat ggctcaggat    7440
caaaggattc gatggtatct gctcagcatg ggcagcaatg aaaacatcca ttctattcat    7500
ttcagtggac atgtgttcac tgtacgaaaa aaagaggagt ataaaatggc actgtacaat    7560
ctctatccag gtgttttga cagtggaaa atgttaccat ccaaagctgg aatttggcgg    7620
gtggaatgcc ttattggcga gcatctacat gctgggatga gcacacttttt tctggtgtac    7680
```

```
agcaataagt gtcagactcc cctgggaatg gcttctggac acattagaga ttttcagatt   7740
acagcttcag gacaatatgg acagtgggcc ccaaagctgg ccagacttca ttattccgga   7800
tcaatcaatg cctggagcac caaggagccc ttttcttgga tcaaggtgga tctgttggca   7860
ccaatgatta ttcacggcat caagacccag ggtgcccgtc agaagttctc cagcctctac   7920
atctctcagt ttatcatcat gtatagtctt gatgggaaga agtggcagac ttatcgagga   7980
aattccactg gaaccttaat ggtcttcttt ggcaatgtgg attcatctgg gataaaacac   8040
aatattttta accctccaat tattgctcga tacatccgtt tgcacccaac tcattatagc   8100
attcgcagca ctcttcgcat ggagttgatg ggctgtgatt taaatagttg cagcatgcca   8160
ttgggaatgg agagtaaagc aatatcagat gcacagatta ctgcttcatc ctactttacc   8220
aatatgtttg ccacctggtc tccttcaaaa gctcgacttc acctccaagg gaggagtaat   8280
gcctggagac ctcaggtgaa taatccaaaa gagtggctgc aagtggactt ccagaagaca   8340
atgaaagtca caggagtaac tactcaggga gtaaaatctc tgcttaccag catgtatgtg   8400
aaggagttcc tcatctccag cagtcaagat ggccatcagt ggactctctt ttttcagaat   8460
ggcaaagtaa aggttttttca gggaaatcaa gactccttca cacctgtggt gaactctcta   8520
gacccaccgt tactgactcg ctaccttcga attcaccccc agagttgggt gcaccagatt   8580
gccctgagga tggaggttct gggctgcgag gcacaggacc tctactgagg gtggccactg   8640
cagcacctgc cactgccgtc acctctccct cctcagctcc agggcagtgt ccctccctgg   8700
cttgccttct acctttgtgc taaatcctag cagacactgc cttgaagcct cctgaattaa   8760
ctatcatcag tcctgcattt cttttggtggg gggccaggag ggtgcatcca atttaactta   8820
actcttacct attttctgca gggggatcct ctactagagt cgacctcgag ggaattccga   8880
taatcaacct ctggattaca aaatttgtga agattgact ggtattctta actatgttgc   8940
tccttttacg ctatgtggat acgctgcttt aatgcctttg tatcatgcta ttgcttcccg   9000
tatggctttc attttctcct ccttgtataa atcctggttg ctgtctcttt atgaggagtt   9060
gtggcccgtt gtcaggcaac gtggcgtggt gtgcactgtg tttgctgacg caacccccac   9120
tggttggggc attgccacca cctgtcagct ccttttccggg actttcgctt tccccctccc   9180
tattgccacg gcggaactca tcgccgcctg ccttgcccgc tgctggacag gggctcggct   9240
gttgggcact gacaattccg tggtgttgtc ggggaagctg acgtcctttc catggctgct   9300
cgcctgtgtt gccacctgga ttctgcgcgg gacgtccttc tgctacgtcc cttcggccct   9360
caatccagcg gaccttcctt cccgcggcct gctgccggct ctgcggcctc ttccgcgtct   9420
tcgccttcgc cctcagacga gtcggatctc cctttgggcc gcctccccgc atcgggaatt   9480
cgagctcggt acctttaaga ccaatgactt acaaggcagc tgtagatctt agccacttt   9540
taaaagaaaa ggggggactg aagggctaa ttcactccca acgaagacaa gatgggatca   9600
attcaccatg gaataacttc gtatagcat acattatacg aagttatgct gcttttttgct   9660
tgtactgggt ctctctggtt agaccagatc tgagcctggg agctctctgg ctaactaggg   9720
aacccactgc ttaagcctca ataaagcttg ccttgagtgc ttcaagtagt gtgtgcccgt   9780
ctgttgtgtg actctggtaa ctagagatcc ctcagaccct tttagtcagt gtggaaaatc   9840
tctagcagca tctagaatta attccgtgta ttctatagtg tcacctaaat cgtatgtgta   9900
tgatacataa ggttatgtat taattgtagc cgcgttctaa cgacaatatg tacaagccta   9960
attgtgtagc atctggctta ctgaagcaga cctatcatc tctctcgtaa actgccgtca   10020
```

```
gagtcggttt ggttggacga accttctgag tttctggtaa cgccgtcccg cacccggaaa    10080
tggtcagcga accaatcagc agggtcatcg ctagccagat cctctacgcc ggacgcatcg    10140
tggccggcat caccggcgcc acaggtgcgg ttgctggcgc ctatatcgcc gacatcaccg    10200
atggggaaga tcgggctcgc cacttcgggc tcatgagcgc ttgtttcggc gtgggtatgg    10260
tggcaggccc cgtggccggg ggactgttgg gcgccatctc cttgcatgca ccattccttg    10320
cggcggcggt gctcaacggc ctcaacctac tactgggctg cttcctaatg caggagtcgc    10380
ataagggaga gcgtcgaatg gtgcactctc agtacaatct gctctgatgc cgcatagtta    10440
agccagcccc gacacccgcc aacaccgcct gacgcgccct gacgggcttg tctgctcccg    10500
gcatccgctt acagacaagc tgtgaccgtc tccgggagct gcatgtgtca gaggttttca    10560
ccgtcatcac cgaaacgcgc gagacgaaag ggcctcgtga tacgcctatt tttataggtt    10620
aatgtcatga taataatggt ttcttagacg tcaggtggca cttttcgggg aaatgtgcgc    10680
ggaaccccta tttgtttatt tttctaaata cattcaaata tgtatccgct catgagacaa    10740
taaccctgat aaatgcttca ataatattga aaaggaagag tatgagtat tcaacatttc     10800 cgtgtcgccc ttattccctt ttttgcggca ttttgccttc ctgttttgc tcacccagaa     10860 acgctggtga agtaaaaga tgctgaagat cagttgggtg cacgagtggg ttacatcgaa     10920
ctggatctca acagcggtaa gatccttgag agttttcgcc ccgaagaacg ttttccaatg    10980
atgagcactt ttaaagttct gctatgtggc gcggtattat cccgtattga cgccgggcaa    11040
gagcaactcg gtcgccgcat acactattct cagaatgact tggttgagta ctcaccagtc    11100
acagaaaagc atcttacgga tggcatgaca gtaagagaat tatgcagtgc tgccataacc    11160
atgagtgata acactgcggc caacttactt ctgacaacga tcggaggacc gaaggagcta    11220
accgcttttt tgcacaacat gggggatcat gtaactcgcc ttgatcgttg ggaaccggag    11280
ctgaatgaag ccataccaaa cgacgagcgt gacaccacga tgcctgtagc aatggcaaca    11340
acgttgcgca aactattaac tggcgaacta cttactctag cttcccggca acaattaata    11400
gactggatgg aggcggataa agttgcagga ccacttctgc gctcggccct tccggctggc    11460
tggtttattg ctgataaatc tggagccggt gagcgtgggt ctcgcggtat cattgcagca    11520
ctggggccag atggtaagcc ctcccgtatc gtagttatct acacgacggg gagtcaggca    11580 actatgatg aacgaaatag acagatcgct gagataggtg cctcactgat taagcattgg    11640
taactgtcag accaagttta ctcatatata ctttagattg atttaaaact tcatttttaa    11700
tttaaaagga tctaggtgaa gatcctttt gataatctca tgaccaaaat cccttaacgt    11760
gagttttcgt tccactgagc gtcagacccc gtagaaaaga tcaaaggatc ttcttgagat    11820 ccttttttc tgcgcgtaat ctgctgcttg caaacaaaaa aaccaccgct accagcggtg    11880
gtttgtttgc cggatcaaga gctaccaact cttttccga aggtaactgg cttcagcaga    11940
gcgcagatac caaatactgt ccttctagtg tagccgtagt taggccacca cttcaagaac    12000
tctgtagcac cgcctacata cctcgctctg ctaatcctgt taccagtggc tgctgccagt    12060
ggcgataagt cgtgtcttac cgggttggac tcaagacgat agttaccgga taaggcgcag    12120
cggtcgggct gaacgggggg ttcgtgcaca cagcccagct tggagcgaac gacctacacc    12180
gaactgagat acctacagcg tgagcattga gaaagcgcca cgcttcccga agggagaaag    12240
gcggacaggt atccggtaag cggcagggtc ggaacaggag agcgcacgag ggagcttcca    12300
gggggaaacg cctggtatct ttatagtcct gtcgggtttc gccacctctg acttgagcgt    12360
cgatttttgt gatgctcgtc aggggggcgg agcctatgga aaaacgccag caacgcggcc    12420
```

```
ttttacggt tcctggcctt ttgctggcct tttgctcaca tgttctttcc tgcgttatcc      12480
cctgattctg tggataaccg tattaccgcc tttgagtgag ctgataccgc tcgccgcagc      12540
cgaacgaccg agcgcagcga gtcagtgagc gaggaagcgg aagagcgccc aatacgcaaa      12600
ccgcctctcc ccgcgcgttg gccgattcat taatgcagct gtggaatgtg tgtcagttag      12660
ggtgtggaaa gtccccaggc tccccagcag gcagaagtat gcaaagcatg catctcaatt      12720
agtcagcaac caggtgtgga aagtccccag gctccccagc aggcagaagt atgcaaagca      12780
tgcatctcaa ttagtcagca accatagtcc cgcccctaac tccgcccatc cgcccctaa       12840 ctccgcccag ttccgcccat tctccgcccc atggctgact aatttttttt atttatgcag      12900
aggccgaggc cgcctcggcc tctgagctat tccagaagta gtgaggaggc ttttttggag      12960
gcctaggctt ttgcaaaaag cttgacacag acaggcttt gcgagatatg tttgagaata      13020
ccactttatc ccgcgtcagg gagaggcagt gcgtaaaaag acgcggactc atgtgaaata      13080 ctggtttta gtcgccaga tctctataat ctcgcgcaac ctattttccc ctcgaacact       13140
ttttaagccg tagataaaca ggctgggaca cttcacatga gcgaaaaata catcgtcacc      13200
tgggacatgt tgcagatcca tgcacgtaaa ctcgcaagcc gactgatgcc ttctgaacaa      13260
tggaaaggca ttattgccgt aagccgtggc ggtctgtacc gggtgcgtta ctggcgcgtg      13320
aactgggtat tcgtcatgtc gataccgttt gtatttccag ctacgatcac gacaaccagc      13380
gcgagcttaa agtgctgaaa cgcgcagaag gcgatggcga aggcttcatc gttattgatg      13440
acctggtgga taccggtggt actgcggttg cgattcgtga atgtatcca aaagcgcact      13500 ttgtcaccat cttcgcaaaa ccggctggtc gtccgctggt tgatgactat gttgttgata      13560
tcccgcaaga tacctggatt gaacagccgt gggatatggg cgtcgtattc gtcccgccaa      13620
tctccggtcg ctaatctttt caacgcctgg cactgccggg cgttgttctt tttaacttca      13680
ggcgggttac aatagtttcc agtaagtatt ctggaggctg catccatgac acaggcaaac      13740
ctgagcgaaa ccctgttcaa ccccgctttt aaacatcctg aaacctcgac gctagtccgc      13800
cgctttaatc acggcgcaca accgcctgtg cagtcggccc ttgatggtaa accatccct       13860 cactggtatc gcatgattaa ccgtctgatg tggatctggc gcggcattga cccacgcgaa      13920
atcctcgacg tccaggcacg tattgtgatg agcgatgccg aacgtaccga cgatgattta      13980
tacgatacgg tgattggcta ccgtggcggc aactggattt atgagtgggc cccggatctt      14040
tgtgaaggaa ccttacttct gtggtgtgac ataattggac aaactaccta cagagattta      14100
aagctctaag gtaaatataa aatttttaag tgtataatgt gttaaactac tgattctaat      14160
tgtttgtgta ttttagattc caacctatgg aactgatgaa tgggagcagt ggtggaatgc      14220
ctttaatgag gaaaacctgt tttgctcaga agaaatgcca tctagtgatg atgaggctac      14280
tgctgactct caacattcta ctcctccaaa aagaagaga aaggtagaag accccaagga      14340 cttccttca gaattgctaa gttttttgag tcatgctgtg tttagtaata gaactcttgc       14400
ttgctttgct atttacacca caaggaaaa agctgcactg ctatacaaga aaattatgga      14460
aaaatattct gtaaccttta taagtaggca taacagttat aatcataaca tactgttttt      14520
tcttactcca cacaggcata gagtgtctgc tattaataac tatgctcaaa aattgtgtac      14580
ctttagcttt ttaatttgta aaggggttaa taaggaatat ttgatgtata gtgccttgac      14640
tagagatcat aatcagccat accacatttg tagaggtttt acttgcttta aaaaacctcc      14700
cacacctccc cctgaacctg aaacataaaa tgaatgcaat tgttgttgtt aacttgttta      14760
```

```
ttgcagctta taatggttac aaataaagca atagcatcac aaatttcaca aataaagcat    14820
ttttttcact gcattctagt tgtggtttgt ccaaactcat caatgtatct tatcatgtct    14880
ggatcaactg gataactcaa gctaaccaaa atcatcccaa acttcccacc ccatacccta    14940
ttaccactgc caattaccta gtggtttcat ttactctaaa cctgtgattc ctctgaatta    15000
ttttcatttt aaagaaattg tatttgttaa atatgtacta caaacttagt ag            15052
```

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
gaacccactg cttaagcctc a                                              21

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
agcttgcctt gagtgcttca                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
agtagtgtgt gcccgtctgt                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
gacccgggag atctgaattc                                                20

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
agtggcacag cagttagg                                                  18

<210> SEQ ID NO 31
<211> LENGTH: 19
<212> TYPE: DNA
<213> ORGANISM: Artificial Sequence
<220> FEATURE:
<223> OTHER INFORMATION: Synthetic

<400> SEQUENCE: 31
acgctatgtg gatacgctg                                                19

<210> SEQ ID NO 32
<211> LENGTH: 1920
<212> TYPE: DNA
<213> ORGANISM: Artificial Sequence
<220> FEATURE:
<223> OTHER INFORMATION: Synthetic

<400> SEQUENCE: 32

| | | |
|---|---|---|
| tatcttctgg tggcccttttt gctgccatga dacagggac tgctgaggac agcgtcaggc | 60 |
| agcaagcttc cggggactcc actcatggta cagtgcatga agccatcctc acagtagcac | 120 |
| atggtgtgat ggtctgagaa gatgtcttct ggctggaaga tctcaccgtc atagtaacag | 180 |
| gggcactggg ccttgggcac gcagtccccc ctctcatcca tgtagagccc tgggggcag | 240 |
| aagcagccct ccaggcaggc ctcattgcat tcctcatccg ggtaagagag agagcggcag | 300 |
| gtcaggttgc aggggtccc gcactgcagg tacacctggc ctttcgggca gttcagctca | 360 |
| cagcggcctg gctcgcgcca cgcgacgcgc acgcctctcc ccgcgcaggc cgcggcatag | 420 |
| ctggccaggg cgccgcacag gcactcgcgg ccgtccgagc aggagcacac gtcgtagcgg | 480 |
| cagttccgca ggtagggcag cgggctgacg gcacgatggc aggcctcgaa tgtgggggac | 540 |
| gtcaggaccg cgcacgcctc ctcggagaac ctggtcatgc gcgggttgag ggcgcaggga | 600 |
| tcgctgtgct gcttctgcag gtcctggcag tccccgtgca gcttccaggc gttcccgaag | 660 |
| tcctccaccc ggggctccgc cagcccagag ggggtaagga agtcgtcgcc ctggttgcca | 720 |
| ttgtaattcc cacacaggcc gcaggtcttc ccggcataga cggggacag cttcaccagc | 780 |
| agcctcccgc ggccatccca gtccatctgc aggtcctccc cgtagctgag gcgcacggag | 840 |
| gccgtcactg tatgctggat gcggaggtca cctttcagga gggggagctg gacgtcctgg | 900 |
| ccatccatgg caactcctgc cccatgcttc agtttcacaa ggctgttgtg caggccaggc | 960 |
| agccggacgg tgacggagcg ggtgcacaca gcgtcgcggt catcagcaca ctggacagtc | 1020 |
| tcaatgacaa tggagaagga gtggtcctgg caatcccggg ccagcaggta ctggcagatc | 1080 |
| ccactgaagg tgaagtatct gttgtcaaag ctcttgaagt gtgattgacc tgtgacaagg | 1140 |
| cactcgcaaa gggtccctgg caaaatgagg gccagagcaa gcagcacccc ggcaaatctg | 1200 |
| gcaggaatca tggtccttct tccacaacct cccaggcagg aatgggccag ctcctcctcc | 1260 |
| ttcccttcag attcctccac aggaagtctt ttcttatcaa actggaaccc caagtaactt | 1320 |
| gctgagcaac gggcagagca aagggctata gcccctggac tcatggtggc tagaattgcc | 1380 |
| aggaagtggg tgaggccacc cagagggtgg atgctcatgg ctgaaagcca tgactcctcc | 1440 |
| cctttcctga gaatagttta ttaccatgtc ctattggttc tgcctatcaa tgatgtctct | 1500 |
| tgaatctttta ccccatctct actaccaccg tgctagtcca agccaccatc actttctgct | 1560 |
| tgggatagcg tgattgtgaa ctggtccata cttgtctact ctagcctaca gttctaatct | 1620 |
| cctcccttcc cccatctggc tgtacagctg tggtgctttg tgacttggcc acaggtcggg | 1680 |
| gaaggagaag gaagctgctg cccccgataa aacctgaggc ttctgtatct ttttggatat | 1740 |
| ggcatttacc cacttcctcc ttctaggacc ttgggcggcc tcaaccagcc atattggtgc | 1800 |
| agcagcttcc tcactcctcc tccgtcttga gccaagcttt agtgtggcca cagcagtgca | 1860 |
| gtcagtgctg gggacagggt ggtgaatgga ccttggtcta ggtggcaagg agatatcgat | 1920 |

<210> SEQ ID NO 33

```
<211> LENGTH: 6
<212> TYPE: PRT
<213> ORGANISM: Artificial Sequence
<220> FEATURE:
<223> OTHER INFORMATION: Synthetic

<400> SEQUENCE: 33

Ser Phe Phe Leu Lys Asn
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic

<400> SEQUENCE: 34

Thr Arg Phe Gly Ala Pro
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic

<400> SEQUENCE: 35

Ser Phe Pro Gly Gln Pro
1               5
```

We claim:

1. A method, comprising:
   contacting a stem cell with an expression vector comprising: a) an expression cassette comprising a fragment of a human integrin αIIb gene (ITGA2B) promoter, wherein said human ITGA2B promoter consists of nucleotides 2453-3156 of SEQ ID NO:25; and an exogenous gene of interest operably linked to said promoter; and b) a targeting factor that targets expression of said gene of interest to a specific location with a cell; to generate a modified stem cell under conditions such that said exogenous gene of interest is expressed in said modified stem cell.

2. The method of claim 1, wherein said stem cell is a hematopoietic stem cell.

3. The method of claim 1, wherein said targeting factor is a fragment of the human Von Willebrand Factor propeptide (VWFpp) operably linked to a D2 domain of VWFpp.

4. The method of claim 1, wherein said exogenous gene of interest is Factor VIII.

5. The method of claim 1, wherein said exogenous gene of interest is IL-24.

6. The method of claim 1, wherein said exogenous gene of interest is integrin αIIb gene or integrin β3 gene.

7. A method, comprising:
   contacting a stem cell with an expression vector comprising: a) an expression cassette comprising a fragment of a human integrin αIIb gene (ITGA2B) promoter, wherein said human ITGA2B promoter consists of nucleotides 18-1271 of SEQ ID NO: 21; and an exogenous gene of interest operably linked to said promoter; and b) a targeting factor that targets expression of said gene of interest to a specific location with a cell; to generate a modified stem cell under conditions such that said exogenous gene of interest is expressed in said modified stem cell.

* * * * *